(12) United States Patent
Ross et al.

(10) Patent No.: US 10,905,822 B2
(45) Date of Patent: Feb. 2, 2021

(54) FLUID DELIVERY APPARATUS HAVING A GAS EXTRACTION DEVICE AND METHOD OF USE

(71) Applicant: SORRENTO THERAPEUTICS, INC., San Diego, CA (US)

(72) Inventors: Russell F. Ross, Jacksonville Beach, FL (US); Andrew T. Baker, Norcross, GA (US); Luke Hagan, Seattle, WA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/738,390

(22) Filed: Jan. 9, 2020

(65) Prior Publication Data
US 2020/0289746 A1 Sep. 17, 2020

Related U.S. Application Data

(63) Continuation of application No. 16/469,035, filed as application No. PCT/US2017/064604 on Dec. 5, 2017, now Pat. No. 10,569,010.
(Continued)

(51) Int. Cl.
*B01D 19/00* (2006.01)
*A61M 5/142* (2006.01)
(Continued)

(52) U.S. Cl.
CPC ... *A61M 5/14244* (2013.01); *A61F 13/00068* (2013.01); *A61M 5/1454* (2013.01);
(Continued)

(58) Field of Classification Search
CPC . B01D 19/00; A61M 5/14244; A61M 5/1454; A61F 13/00068
See application file for complete search history.

(56) References Cited

U.S. PATENT DOCUMENTS 3,822,601 A * 7/1974 Borom ................... B63C 11/32
73/865.1
4,734,092 A 3/1988 Millerd
(Continued)

FOREIGN PATENT DOCUMENTS

EP 0113562 A1 7/1984
EP 1743667 A2 1/2007
(Continued)

OTHER PUBLICATIONS

Extended European Search Report for Application No. 17881984.3; dated Jun. 17, 2020; 9 pages.
(Continued)

*Primary Examiner* — Robert A Hopkins
(74) *Attorney, Agent, or Firm* — Armstrong Teasdale LLP

(57) ABSTRACT

A gas extraction device for a fluid delivery apparatus includes a first layer and a vent membrane coupled to the first layer. The vent membrane enables a gas to pass through the vent membrane and prevents a fluid from passing through the vent membrane. The gas extraction device also includes a second layer coupled to the vent membrane opposite the first layer. The second layer has a first channel formed therethrough. In addition, the gas extraction device includes an impermeable membrane coupled to the second layer opposite the vent membrane. The first channel is configured to receive a fluid having a gas dispersed therein. The fluid is pressurized to move the fluid through the first channel against the vent membrane and to move the gas through the vent membrane.

20 Claims, 47 Drawing Sheets

Related U.S. Application Data

(60) Provisional application No. 62/435,104, filed on Dec. 16, 2016.

(51) Int. Cl.
*A61F 13/00* (2006.01)
*A61M 5/145* (2006.01)
*A61M 31/00* (2006.01)
*A61M 37/00* (2006.01)
*A61M 5/38* (2006.01)
*A61M 5/158* (2006.01)

(52) U.S. Cl.
CPC ........ *A61M 31/00* (2013.01); *A61M 37/0015* (2013.01); *B01D 19/0031* (2013.01); *A61M 5/385* (2013.01); *A61M 2005/1585* (2013.01); *A61M 2037/0023* (2013.01); *A61M 2209/088* (2013.01)

(56) References Cited

U.S. PATENT DOCUMENTS

| | | |
|---|---|---|
| 5,224,928 A | 7/1993 | Sibalis et al. |
| 5,314,405 A | 5/1994 | Kriesel et al. |
| 6,299,673 B1 | 10/2001 | Field et al. |
| 6,508,859 B1 | 1/2003 | Zia et al. |
| 6,770,434 B2 | 8/2004 | Shvets et al. |
| 7,437,914 B2 | 10/2008 | Harding et al. |
| 7,686,029 B2 | 3/2010 | Nakao |
| 7,854,732 B2 | 12/2010 | Massengale et al. |
| 8,192,534 B2 | 6/2012 | Hekmat et al. |
| 8,317,168 B2 | 11/2012 | Murakami |
| 8,652,095 B2 | 2/2014 | Stroem et al. |
| 8,889,085 B2 | 11/2014 | Lee et al. |
| 8,895,292 B2 | 11/2014 | Soderlund et al. |
| 9,061,277 B2 | 6/2015 | Jung et al. |
| 2002/0022855 A1 | 2/2002 | Bobroff et al. |
| 2004/0025693 A1 | 2/2004 | Bedingfield et al. |
| 2004/0204687 A1 | 10/2004 | Mogensen et al. |
| 2005/0096856 A1 | 5/2005 | Trautman |
| 2006/0090645 A1 | 5/2006 | Kent |
| 2007/0293826 A1 | 12/2007 | Wall et al. |
| 2008/0317632 A1 | 12/2008 | Shimasaki et al. |
| 2009/0292335 A1 | 11/2009 | Leonov |
| 2010/0234805 A1 | 9/2010 | Kaufmann et al. |
| 2011/0172601 A1 | 7/2011 | Beebe et al. |
| 2011/0172609 A1 | 7/2011 | Moga et al. |
| 2011/0276028 A1 | 11/2011 | Singh et al. |
| 2011/0319279 A1 | 12/2011 | Montagu et al. |
| 2012/0130207 A1 | 5/2012 | O'Dea et al. |
| 2012/0143136 A1 | 6/2012 | Constantineau et al. |
| 2012/0310182 A1 | 12/2012 | Fielder et al. |
| 2013/0211289 A1 | 8/2013 | Moga et al. |
| 2013/0345638 A1 | 12/2013 | Heidenreich et al. |
| 2015/0209783 A1 | 7/2015 | Ingber et al. |
| 2015/0352547 A1 | 12/2015 | Breinlinger et al. |
| 2015/0359965 A1 | 12/2015 | O'Connor et al. |
| 2016/0038434 A1 | 2/2016 | Schaller et al. |
| 2016/0193412 A1 | 7/2016 | Cereda et al. |

FOREIGN PATENT DOCUMENTS

| | | |
|---|---|---|
| ES | 2266803 T3 | 3/2007 |
| WO | 0205889 A1 | 1/2002 |
| WO | 2013070715 A1 | 5/2013 |
| WO | 2014116998 A2 | 7/2014 |
| WO | 2015015170 A1 | 2/2015 |
| WO | 2015168210 A1 | 11/2015 |
| WO | 2016023637 A1 | 2/2016 |

OTHER PUBLICATIONS

International Search Report for International Application No. PCT/US2017/064604, dated Mar. 15, 2018, 4 pages.
Written Opinion of the International Searching Authority for International Application No. PCT/US2017/064604, dated Mar. 15, 2018, 9 pages.
International Preliminary Report on Patentability for International Application No. PCT/US2017/064604, dated Mar. 25, 2019, 6 pages.
Seemann, R. et al. 2005. Welling morphologies at microstructured surfaces. PNAS, vol. 102, No. 6, pp. 1848-1852.
EPO Extended Search Report for EP Application 17882071.8 dated Jul. 31, 2020; 9 pp.
EPO Extended Search Report for EP Application 17881748.2 dated Jul. 17, 2020; 8 pp.
EPO Extended Search Report for EP Patent Application 17880143.7 dated Nov. 5, 2020; 7 pp.

\* cited by examiner

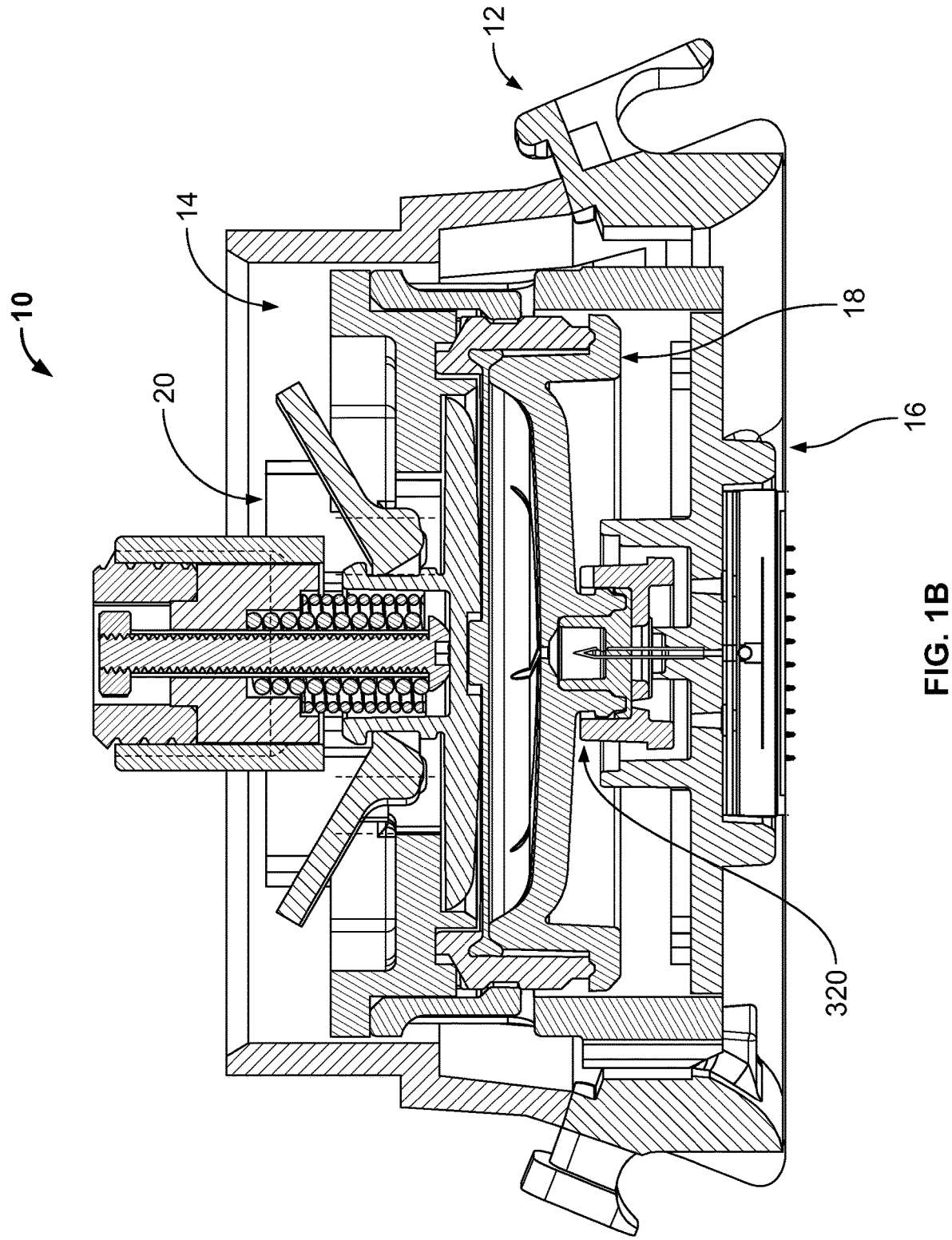

FLUID DELIVERY APPARATUS HAVING A GAS EXTRACTION DEVICE AND METHOD OF USE

CROSS-REFERENCE TO RELATED APPLICATIONS

This application is a continuation application of U.S. patent application Ser. No. 16/469,035 filed Jun. 12, 2019, which is a National Stage entry of PCT/US2017/064604, filed Dec. 5, 2017, which claims the benefit of priority to U.S. Provisional Patent Application No. 62/435,104, filed Dec. 16, 2016, the contents of each are hereby expressly incorporated by reference in their entirety.

FIELD OF THE DISCLOSURE

The present disclosure relates generally to a fluid delivery apparatus, and more particularly to a microfluidic device having a gas extraction device for removing gas bubbles from the fluid.

BACKGROUND OF THE DISCLOSURE

Numerous apparatus have been developed for transdermal delivery of medicines using microneedle assemblies. Microneedle assemblies facilitate reducing an amount of pain felt by a patient as compared to larger conventional needles. Moreover, conventional subcutaneous (and often intra-muscular) delivery of medicines using a needle operates to deliver a large quantity of the medicine at one time, thereby creating a spike in the bioavailability of the medicine. While this is not a significant problem for some medicines, many medicines benefit from having a steady state concentration in the patient's blood stream. Transdermal delivery apparatus are capable of administering drugs at a substantially constant rate over an extended period of time.

However, delivery of medicine using transdermal delivery apparatuses poses several challenges. For example, with at least some known transdermal delivery apparatuses, the placement of the device with respect to a user's skin and the amount of force used to attach the device to the skin can vary, thereby affecting the ability of the microneedles to properly penetrate the user's skin. In addition, the medicine may have air bubbles dispersed therethrough, which can also affect the delivery of the medicine through each microneedle of the microneedle assembly. Moreover, the quantity of the medicine delivered through each microneedle of the microneedle assembly may not be constant or equal due to variances in the pressure supplied to the medicine.

BRIEF DESCRIPTION

In one aspect, a gas extraction device for a fluid delivery apparatus is provided. The gas extraction device includes a first layer and a vent membrane coupled to the first layer. The vent membrane is configured to enable a gas to pass through the vent membrane and prevent a fluid from passing through the vent membrane. The gas extraction device also includes a second layer coupled to the vent membrane opposite the first layer. The second layer includes a first channel formed therethrough. Moreover, the gas extraction device includes an impermeable membrane coupled to the second layer opposite the vent membrane. The first channel is configured to receive a fluid having a gas dispersed therein. The fluid is pressurized to move the fluid through the first channel against the vent membrane and to move the gas through the vent membrane.

In another aspect, a fluid delivery apparatus is provided. The fluid delivery apparatus includes a cartridge assembly containing a fluid and a plenum assembly coupled to the cartridge assembly. The plenum assembly includes a cannula and a lower mounting surface. In addition, the fluid delivery apparatus includes a gas extraction device coupled to the lower mounting surface. The gas extraction device has a first adhesive layer coupled to the mounting surface. The first adhesive layer includes an aperture axially aligned with the cannula and configured to receive the fluid therethrough. The gas extraction device also includes a vent membrane coupled to the first adhesive layer. The vent membrane is configured to enable gas to pass through the vent membrane and prevent the fluid from passing through the vent membrane. Furthermore, the gas extraction device includes an impermeable membrane coupled to the vent membrane. The impermeable membrane and the vent membrane define a first channel therebetween. The first channel is configured to receive the fluid, and the fluid is pressurized to move the fluid through the first channel against the vent membrane and to move the gas through the vent membrane.

In yet another aspect, a method of removing gas from a liquid is provided. The method includes coupling a liquid reservoir to a gas extraction device. The gas extraction device has a vent membrane configured to enable gas to pass through the vent membrane and prevent a fluid from passing through the vent membrane, a first adhesive layer coupled to the vent membrane and having a first channel formed therethrough, and an impermeable membrane coupled to the first adhesive layer opposite the vent membrane. The method also includes channeling the liquid through the first channel in the first adhesive layer. The channeling of the liquid causes the liquid to contact the vent membrane. Contacting the vent membrane causes the gas to move through the vent membrane.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 1B is a sectional view of the fluid delivery apparatus in a pre-activated configuration;

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all additional features known by those of ordinary skill in the art to be required for the practice of the embodiments disclosed herein.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, positional terms such as upward, downward, upper, lower, top, bottom, and the like are used only for convenience to indicate relative positional relationships.

As used herein, for the purposes of description and claims, the term "fluid" applies only to liquids, and should not be taken to include gaseous products.

Figure 1A:
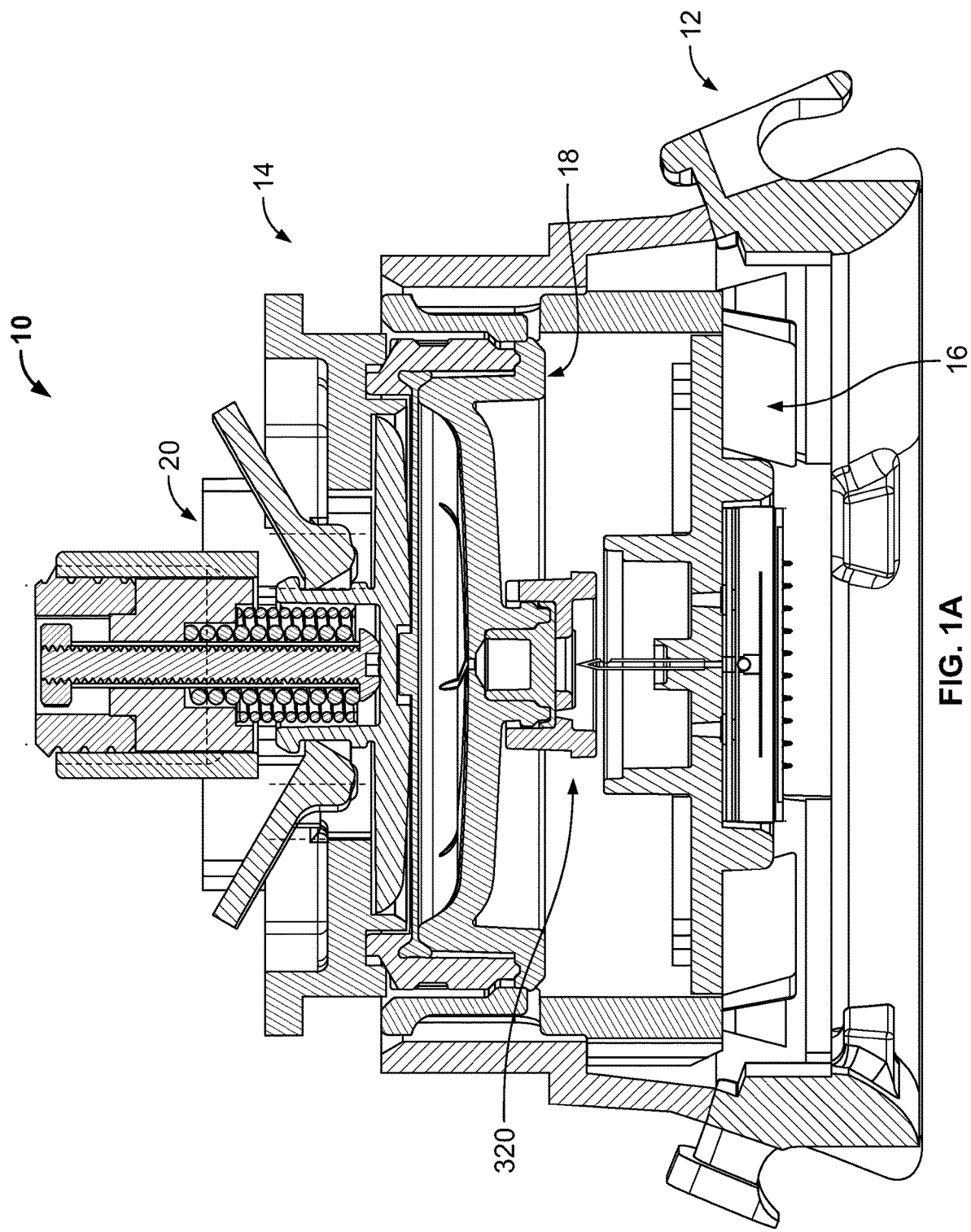
FIG. 1A is a sectional view of an exemplary fluid delivery apparatus in a pre-use configuration.
Figure 2:
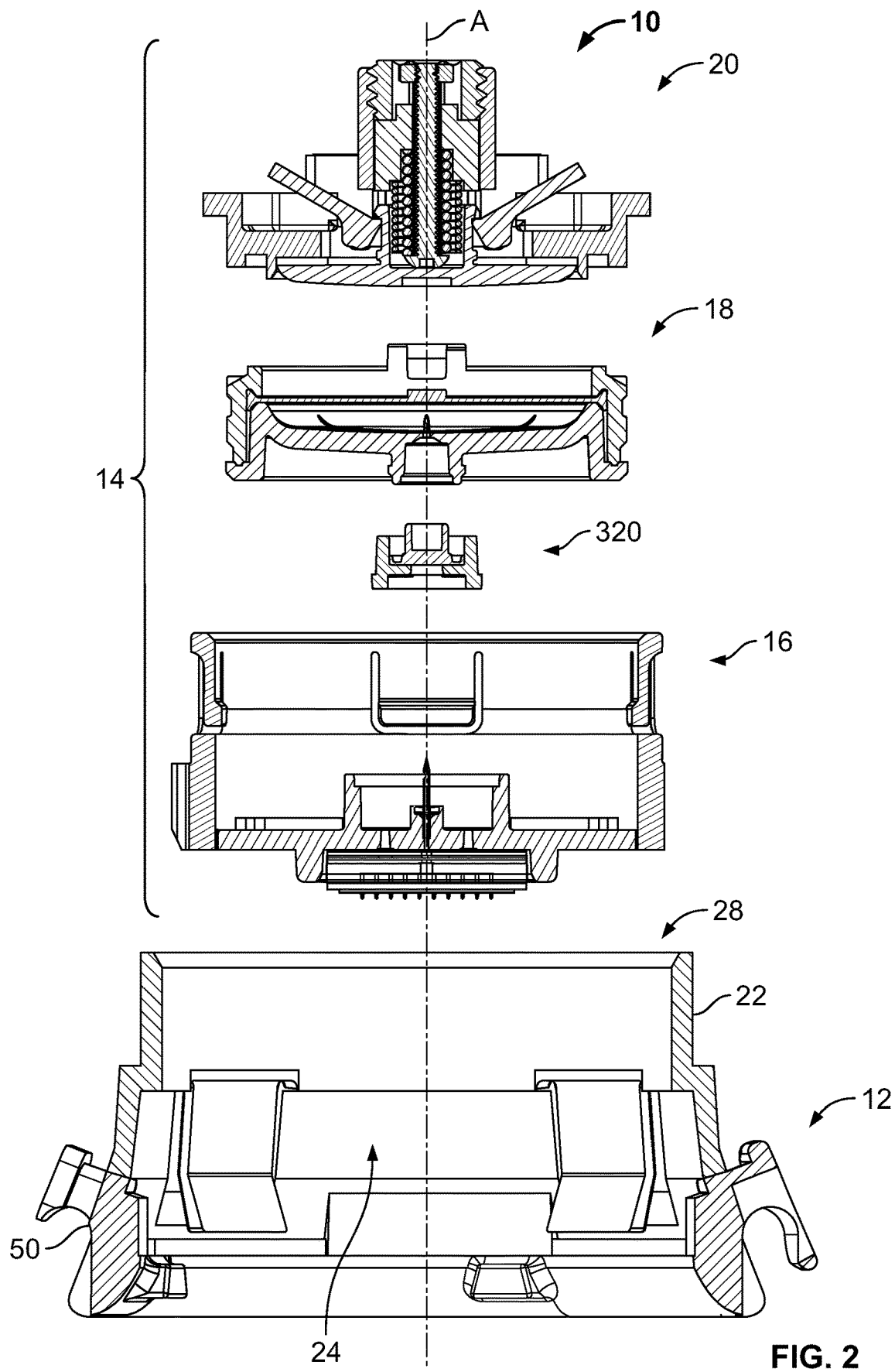
FIG. 2 is an exploded, sectional view of fluid delivery apparatus.

FIG. 1A is a sectional view of an exemplary fluid delivery apparatus (e.g., a drug delivery apparatus), indicated generally by 10, in a pre-use configuration. FIG. 1B is a sectional view of the fluid delivery apparatus 10 in a pre-activated configuration. FIG. 2 is an exploded, sectional view of fluid delivery apparatus 10. In the exemplary embodiment, the fluid delivery apparatus 10 includes a plurality of subassembly components coupled together to form the fluid delivery apparatus 10, including a collet assembly 12 and a fluid distribution assembly 14. The collet assembly 12 and the fluid distribution assembly 14 are indicated generally by their respective reference numbers. As shown in FIG. 2, the fluid distribution assembly 14 includes a plurality of additional subassembly components, including a plenum assembly 16, a cartridge assembly 18, a cap assembly 320, and a mechanical controller assembly 20. Each of the collet assembly 12, the fluid distribution assembly 14, the plenum assembly 16, the cartridge assembly 18, the cap assembly 320, and the mechanical controller assembly 20 is indicated generally in the accompanying drawings by their reference numbers. The collet assembly 12 forms the body or housing of the fluid delivery apparatus 10 and is slidably coupled to the fluid distribution assembly 14. To form the fluid distribution assembly 14, the cap assembly 320 is coupled to the cartridge assembly 18, and the cartridge assembly 18 is slidably coupled to the plenum assembly 16. In addition, the mechanical controller assembly 20, as explained in more detail below, is coupled to the cartridge assembly 18.

Figure 3:
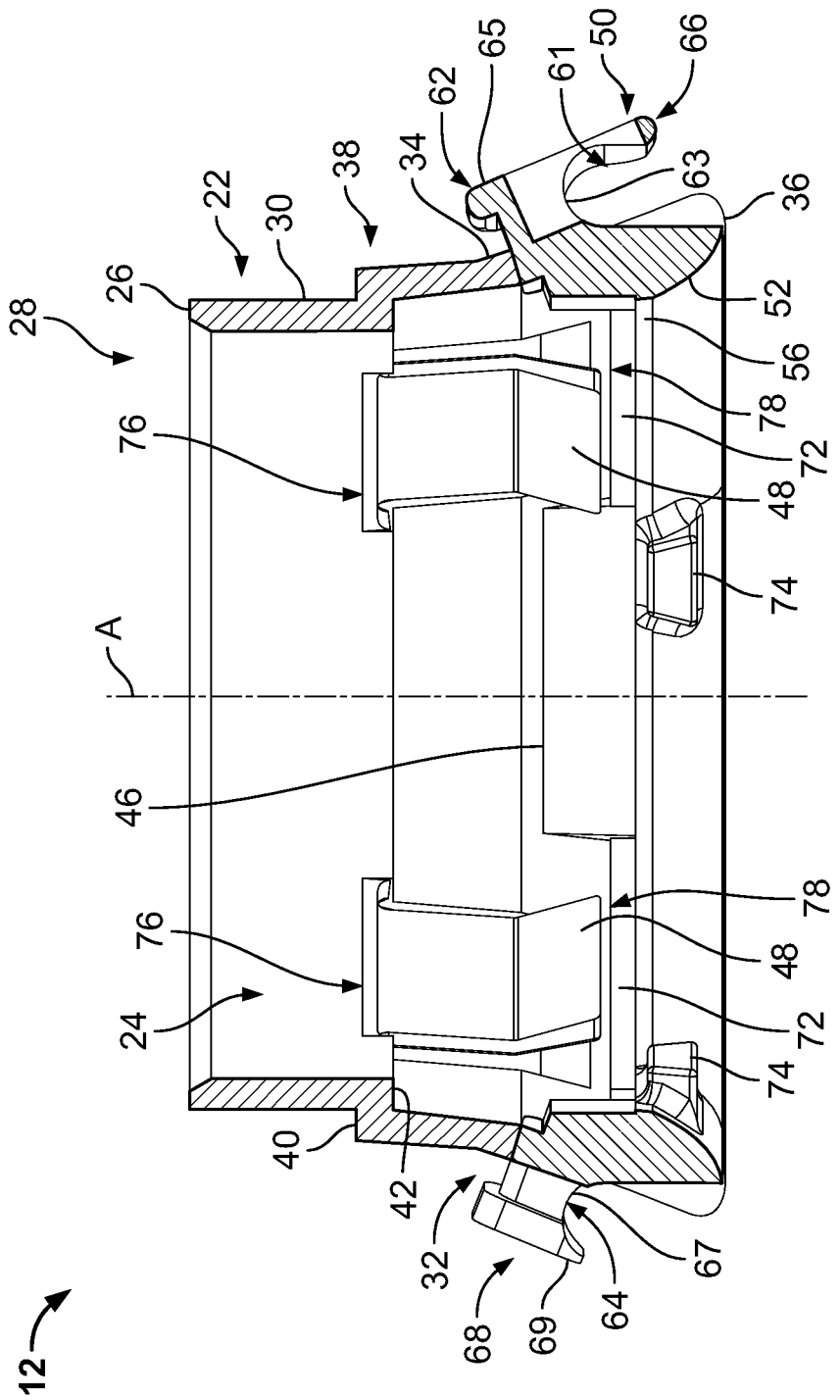
FIG. 3 is a sectional view of a collet assembly of the fluid delivery apparatus.
Figure 4:
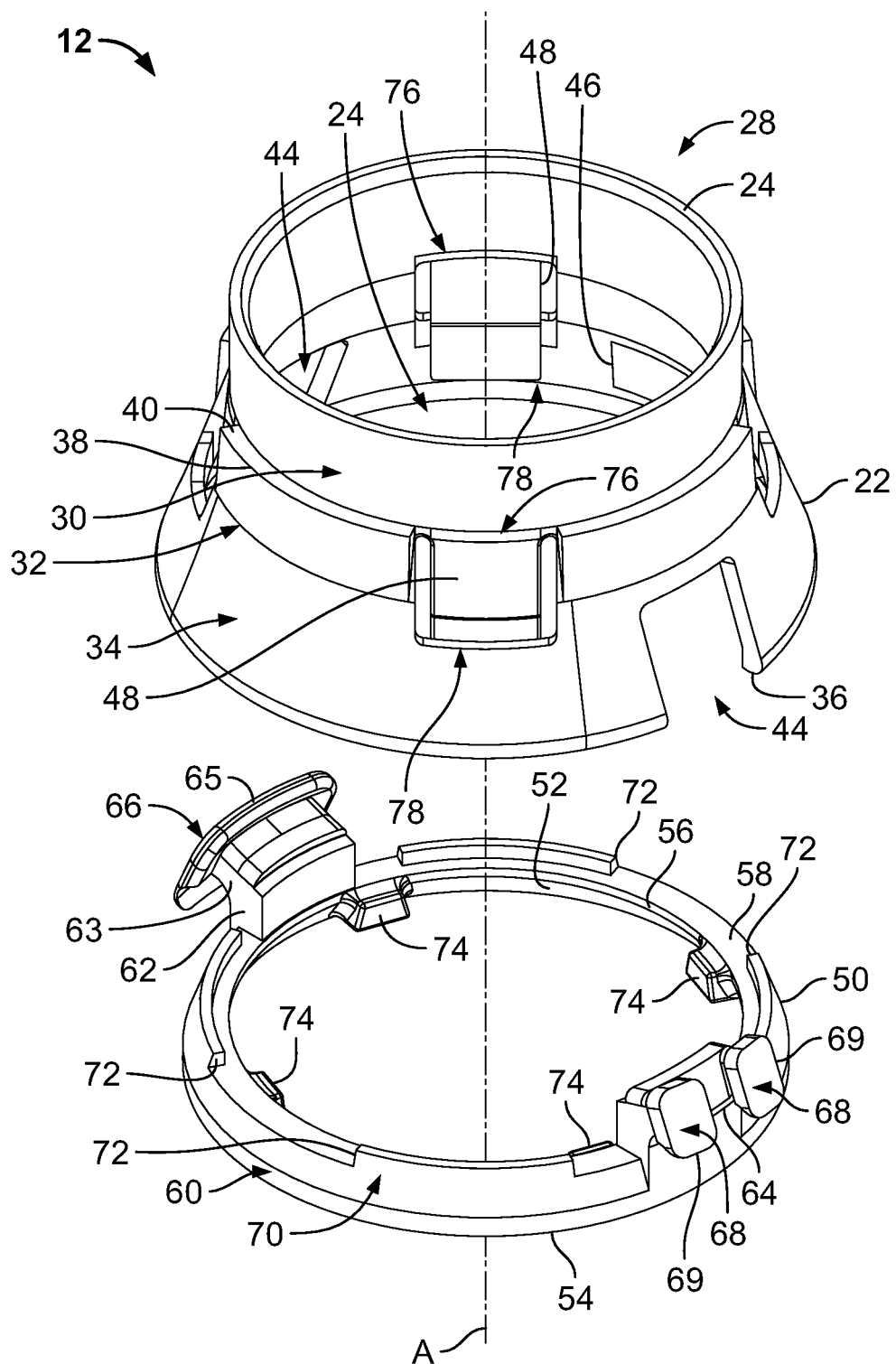
FIG. 4 is an exploded, perspective view of the collet assembly shown in FIG. 3.

FIG. 3 is a sectional view and FIG. 4 is an exploded, perspective of the collet assembly 12 of the fluid delivery apparatus 10. Referring to FIGS. 2-4, in the exemplary embodiment, the collet assembly 12 includes a collet 22 coupled to a collet lock 50. In the exemplary embodiment, the collet 22 is formed in a generally frustoconical shape, having a hollow interior space 24 defined therein. The collet 22 is formed generally symmetrically about a central axis "A." An upper rim 26 of the collet 22 defines an opening 28 to the interior space 24. A cylindrical upper wall 30 extends generally vertically downward from the upper rim 26 towards a central portion 32 of the collet 22. A lower wall 34 extends downward at an outward angle from the central portion 32 toward a base 36 (or lower edge) of the collet 22. The upper wall 30, central portion 32, and the lower wall 34 collectively define the interior space 24. A step 38 extends around the upper wall 30, defining an outer horizontal surface 40 (or ledge) configured to engage an attachment band 430 (shown in FIG. 36), as is described further herein. The step 38 also defines an inner horizontal surface 42 (or step) configured to engage with the plenum assembly 16 to facilitate properly positioning the plenum assembly 16 above a user's skin surface prior to use of the fluid delivery apparatus 10.

As illustrated in FIG. 4, the collet 22 includes a pair of notches, indicated generally at 44, opposite each other and formed through the lower wall 34. In the exemplary embodiment, the notches 44 are generally rectangular in shape and configured to receive a portion of the collet lock 50. In addition, the collet 22 includes one or more stops 46 configured to facilitate positioning of the collet lock 50 when coupled to the collet 22. For example, and without limitation, the one or more stops 46 are formed as inward extending projections formed on lower wall 34. The stops 46 can have form or shape that enables the stops 46 to function as described herein.

As illustrated in FIGS. 3 and 4, the collet 22 includes a plurality of flexible tabs 48 formed integrally with the upper wall 30. In addition, the plurality of flexible tabs 48 are positioned about and equidistant from the central axis "A." In particular, the plurality of flexible tabs 48 extend from a first end 76 to an opposite free second end 78. In the exemplary embodiment, the free second end 78 angles radially inward and is configured to engage with the plenum assembly 16 to facilitate properly positioning the plenum assembly 16 at the user's skin surface during use of the fluid delivery apparatus 10.

As illustrated in FIGS. 3 and 4, in the exemplary embodiment, the collet lock 50 is generally ring-shaped, having a convex inner surface 52 extending from a lower outer edge 54 of the collet lock 50 to a generally cylindrical inner wall 56. The inner wall 56 extends upward to an upper surface 58. The collet lock 50 includes a generally cylindrical outer wall 60 that is concentric with inner wall 56 and extends upward from the lower outer edge 54. In addition, the collet lock 50 includes latching members 62, 64, opposite each other and extending upward from the upper surface 58. The latching members 62, 64 are configured to couple to the notches 44 of the collet 22. The latch member 62 includes a first coupling member 66 that extends outward from latch member 62. In particular, the first coupling member 66 includes a neck portion 63 that extends at an upward angle substantially perpendicular to the lower wall 34 of the collet 22. In addition, the first coupling member 66 includes a head portion 65 that extends generally parallel to the lower wall 34 beyond a periphery of the neck portion 63. Furthermore, the first coupling member 66 includes a window or aperture 61 extending through the head portion 65. The window 61 is configured to present an indication to the user of the fluid delivery apparatus 10 of a tightness of the attachment band 430, as is further described herein.

Similarly, the latching member 64 includes an adjacent pair of second coupling members 68 that extend outward from latching member 64. In the exemplary embodiment, the coupling members 68 each include a neck portion 67 that extends at an upward angle substantially perpendicular to the lower wall 34 of the collet 22. In addition, the second coupling members 68 include a head portion 69 that extends generally parallel to the lower wall 34 beyond a periphery of the neck portion 67. The first coupling member 66 and the pair of second coupling members 68 are configured to engage the attachment band 430, as is described further herein.

In the exemplary embodiment, the outer wall 60 of the collet lock 50 includes an upper outer surface 70 that inclines inward at an angle substantially parallel to the lower wall 34 to facilitate face-to-face engagement therewith. In addition, the upper surface 58 includes a plurality of stop members 72 that extend upward and are configured to engage the one or more stops 46 of the collet 22 to facilitate properly positioning of the collet lock 50 when coupled to the collet 22. Extending radially inward from the convex inner surface 52 is a plurality of tabs 74 configured to engage with the plenum assembly 16 to facilitate properly positioning the plenum assembly 16 at the user's skin surface during use of the fluid delivery apparatus 10.

In the exemplary embodiment, the collet 22 is coupled to the collet lock 50 to form a unitary assembly (shown in FIG. 3). In particular, the upper surface 70 and the latching members 62, 64 of the collet lock 50 engage the lower wall 34 and the notches 44 of the collet 22 via a permanent coupling method, for example, and without limitation, via an adhesive bond, a weld joint (e.g., spin welding, ultrasonic welding, laser welding, or heat staking), and the like. Alternatively, the collet 22 and the collet lock 50 may be coupled together using any connection technique that enables the formation of the collet assembly 12.

Figure 5:
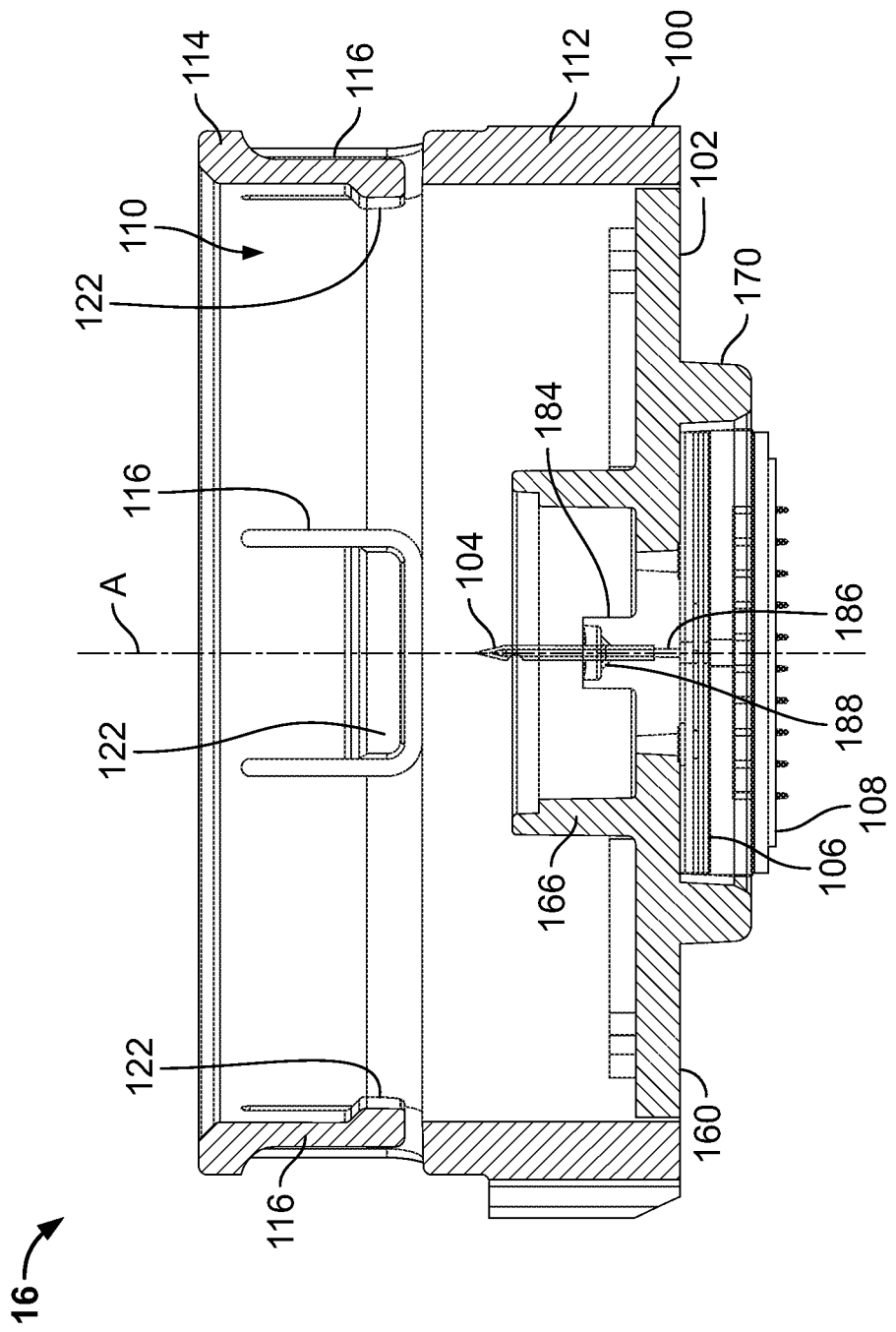
FIG. 5 is a sectional view of a plenum assembly of the fluid delivery apparatus.
Figure 6:
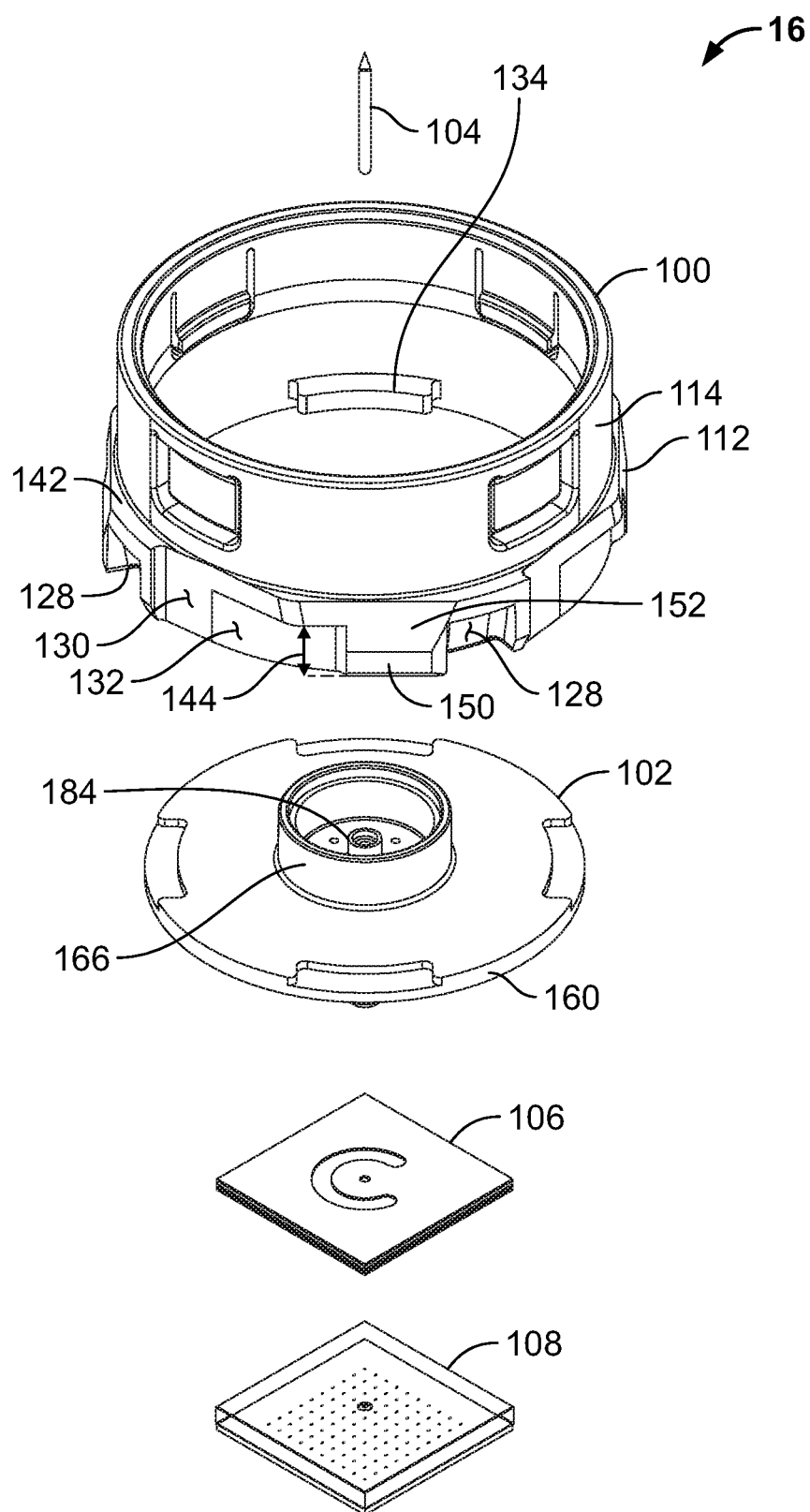
FIG. 6 is an exploded, perspective view of the plenum assembly.

FIG. 5 is a sectional view of the plenum assembly 16 of the fluid delivery apparatus 10. FIG. 6 is an exploded, perspective view of the plenum assembly 16. In the exemplary embodiment, the plenum assembly 16 includes a sleeve component 100, a plenum component 102, a cannula 104, a plenum cap assembly 106 (broadly, "a gas extraction device"), and a microneedle array assembly 108 coupled together to form the unitary plenum assembly 16. In particular, the sleeve component 100 is coupled to the plenum component 102 to define a cavity 110 therein. In the exemplary embodiment, the sleeve component 100 is coupled to the plenum component 102 for example, and without limitation, via an adhesive bond, a weld joint (e.g., spin welding, ultrasonic welding, laser welding, or heat staking), and the like. Alternatively, the sleeve component 100 and the plenum component 102 may be coupled together using any connection technique that enables the formation of the plenum assembly 16.

Figure 7:
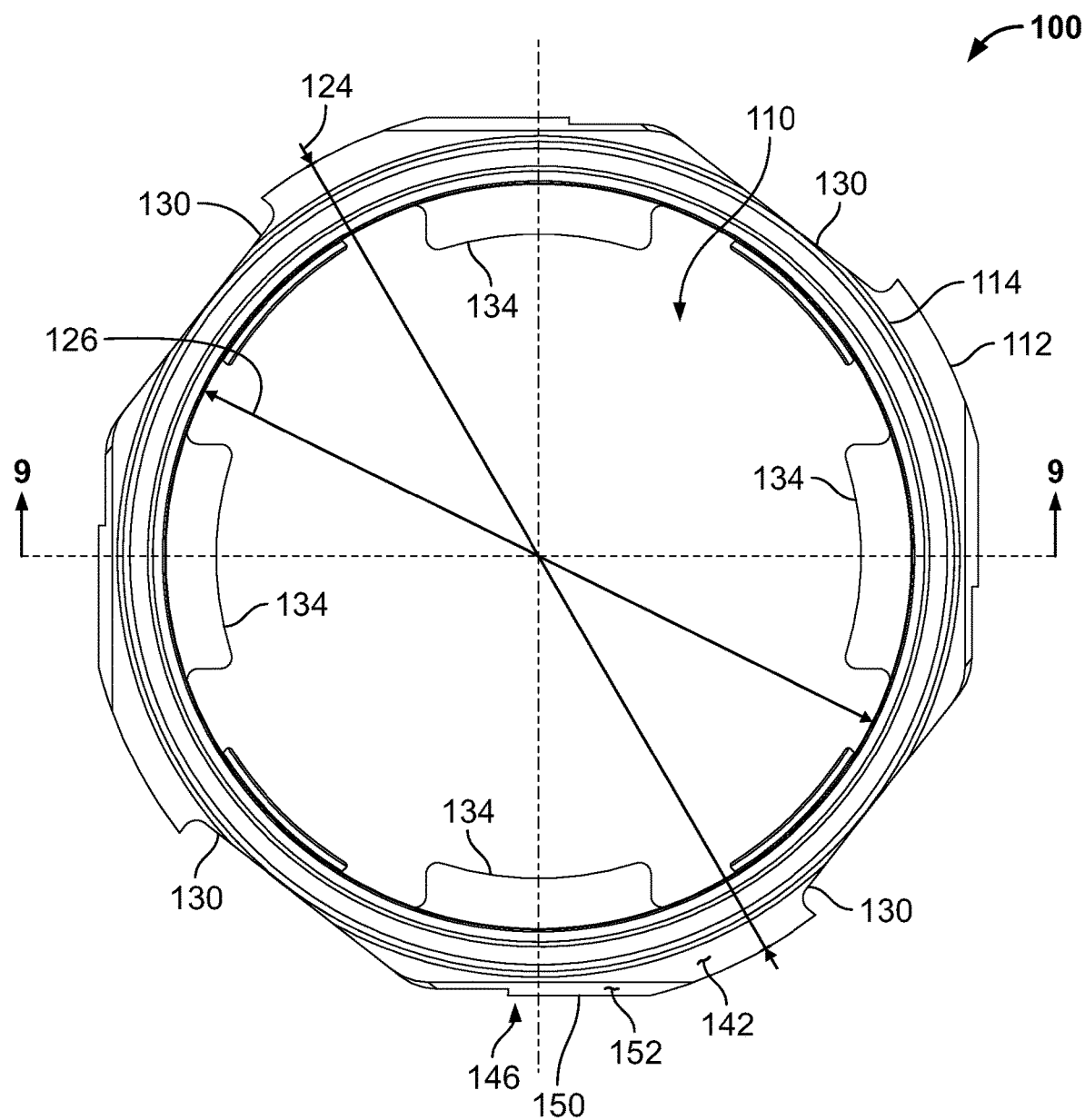
FIG. 7 is a top view of a sleeve component of the plenum assembly.
Figure 8:
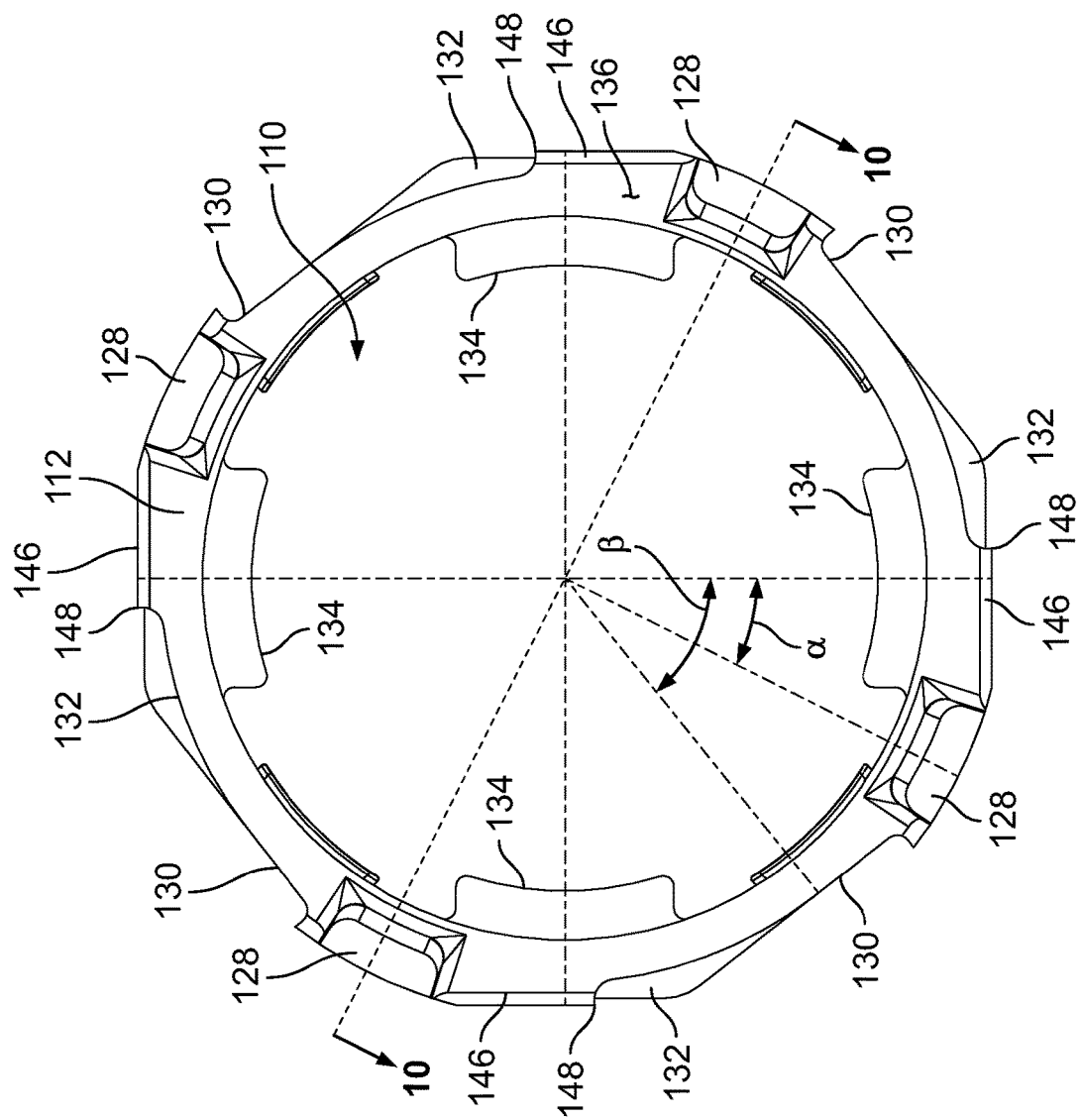
FIG. 8 is a bottom view of the sleeve component.
Figure 9:
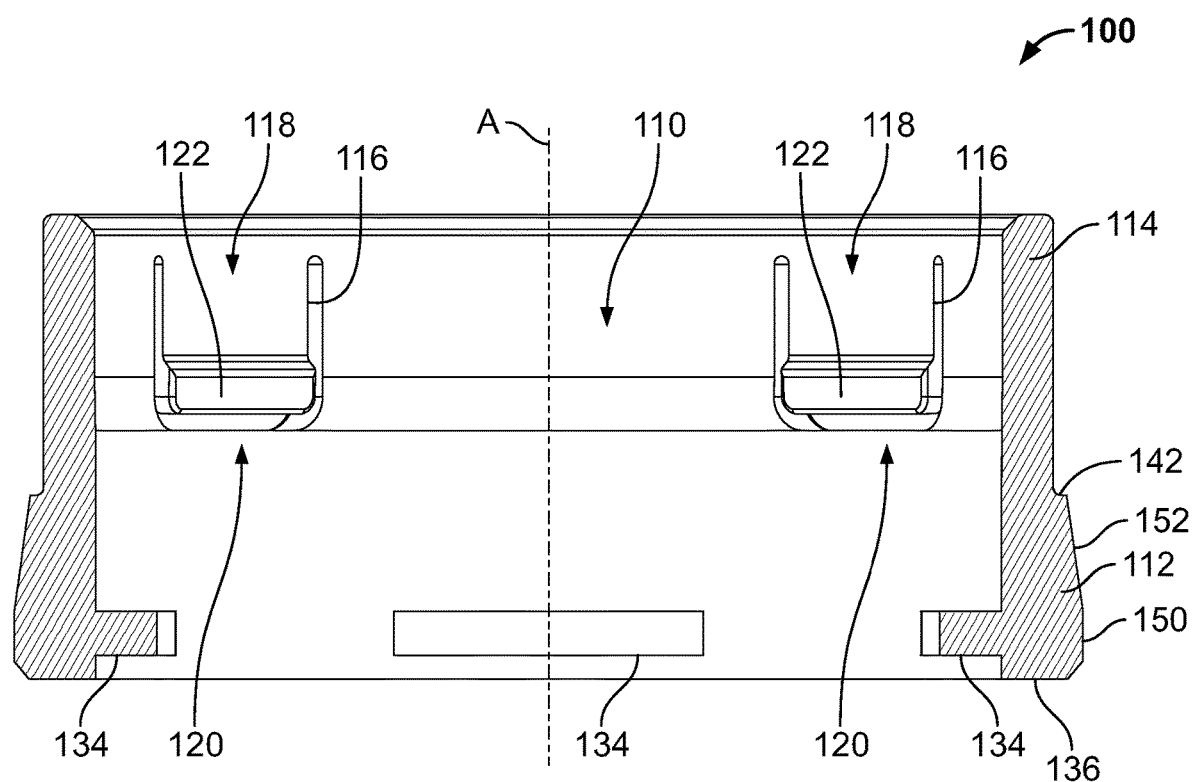
FIG. 9 is a section view of the sleeve component taken about line 9-9 shown in FIG. 7.
Figure 10:
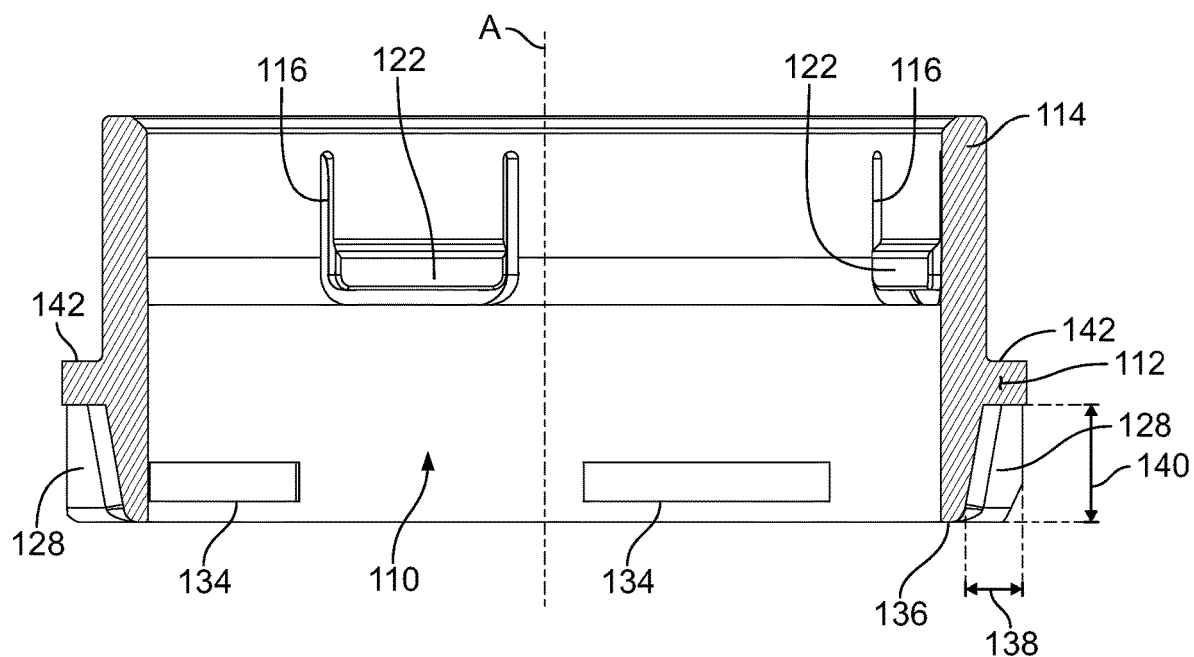
FIG. 10 is a section view of the sleeve component taken about line 10-10 shown in FIG. 8.

FIG. 7 is a top view of the sleeve component 100, FIG. 8 is a bottom view of the sleeve component 100, FIG. 9 is a section view of the sleeve component 100 taken about line 9-9 shown in FIG. 7, and FIG. 10 is a section view of the sleeve component 100 taken about line 10-10 shown in FIG. 8. As illustrated in FIGS. 5-10, in the exemplary embodiment, the sleeve component 100 includes a lower annular wall portion 112 and an upper annular wall portion 114. The upper annular wall portion 114 includes a plurality of flexible tabs 116 that extend substantially axially about the central axis "A" of the sleeve component 100 and are formed integrally with the upper wall portion 114. The plurality of flexible tabs 116 are positioned equidistant about the central axis "A" with respect to each other. While four flexible tabs 116 are shown in the figures, it is noted that in other embodiments the sleeve component 100 has any number of the flexible tabs 116 that enable the sleeve component 100 to function as described herein. In the exemplary embodiment, each flexible tab 116 extends from a first end 118 to an opposite free second end 120. The free second end 120 includes a radially inward extending protrusion 122 that is positioned to engage the cartridge assembly 18 to facilitate properly positioning the cartridge assembly 18 in the pre-use and pre-activated configurations.

As illustrated in FIG. 7, the lower wall portion 112 has an outer diameter 124 and an inner diameter 126, between which a plurality of recesses 128, 130, 132 are defined. While four sets of recesses 128, 130, 132, positioned equidistant about the central axis "A," are shown in the figures, it is noted that in other embodiments the sleeve component 100 has any number of sets of recesses 128, 130, 132 that enables the sleeve component 100 to function as described herein. The lower wall portion 112 also includes a plurality of inwardly extending flange members 134 positioned equidistant about central axis "A." Four flange members 134 are shown in the figures, however, it is noted that in other embodiments, the sleeve component 100 has any number of flange members 134 that enables the sleeve component 100 to function as described herein. In the exemplary embodiment, the flange members 134 are configured to engage and couple to corresponding recesses 190 formed in the plenum component 102.

In the exemplary embodiment, a respective recess 128 (or pocket) is formed as a generally rectangular-shaped recess in the lower wall portion 112, extending from the outer diameter 124 a predefined radial distance 138 into the lower wall portion 112. As illustrated in FIG. 8, the recess 128 is offset circumferentially from the center of a respective flange member 134 at an angle α. As best illustrated in FIG. 10, the recess 128 extends upwardly from a bottom surface 136 of the sleeve component 100 a predetermined distance 140, and is configured to receive a respective tab 74 of the collet lock 50 therein.

Furthermore, in the exemplary embodiment, a respective recess 130 is formed as a flat surface formed in the lower wall portion 112, wherein the recess 130 extends from the bottom surface 136 to a top surface 142 (or ledge) of the lower wall portion 112 and is substantially perpendicular to a radial line extending from the central axis "A." As illustrated in FIG. 8, the recess 130 is formed substantially perpendicular to a radial line defined at an angle β from the center of a respective flange member 134. In the exemplary embodiment, the recess 130 is configured to enable a respective tab 74 of the collet lock 50 to pass in an axial direction without interference with the sleeve component 100 during assembly of the plenum assembly 16 with the collet assembly 12.

Moreover, in the exemplary embodiment, a respective recess 132 is formed as an arcuate recess that extends tangentially from the recess 130 in a circumferential direction and with a continuous radius with respect to the central axis "A." In particular, the recess 132 extends circumferentially an arcuate distance that allows a respective tab 74 of the collet lock 50 to be received therein, while simultaneously allowing a respective flexible tab 48 of the collet 22 to align with, and be received by, the recess 130 during assembly of the plenum assembly 16 with the collet assembly 12. As illustrated in FIG. 6, the recess 132 extends upwardly from the bottom surface 136 a predetermined height 144.

The lower wall portion 112 also includes a plurality of protrusions or stops 146 defined in part by recesses 128, 130, 132. In the exemplary embodiment, each of the stops 146 extends between a circumferential end portion 148 of the recess 132 and an adjacent recess 128 (shown in FIG. 8). The stops 146 are configured to prevent rotation of the plenum assembly 16 when the tabs 74 of the collet lock 50 are located in the recesses 128 or at the circumferential end portions 148 of the recesses 132. Each of the stops 146 includes an outer surface 150 that extends generally axially and is substantially perpendicular to a radial line extending from the central axis "A." In addition, each of the stops 146 includes an inclined surface 152 that extends upwardly from the outer surface 150 to the top surface 142 of the lower wall portion 112. The stops 146 are configured to engage the flexible tabs 48 of the collet 22 to facilitate preventing rotation of the plenum assembly 16 with respect to the collet assembly 12 after assembly of the fluid delivery apparatus 10. As illustrated in FIG. 6, a portion of the surface of the recess 130 extends circumferentially over the recess 132 and couples to the inclined surface 152, thereby functioning as a ramp configured to engage the flexible tabs 48 of the collet 22 during assembly of the plenum assembly 16 to the collet assembly 12.

Figure 11:
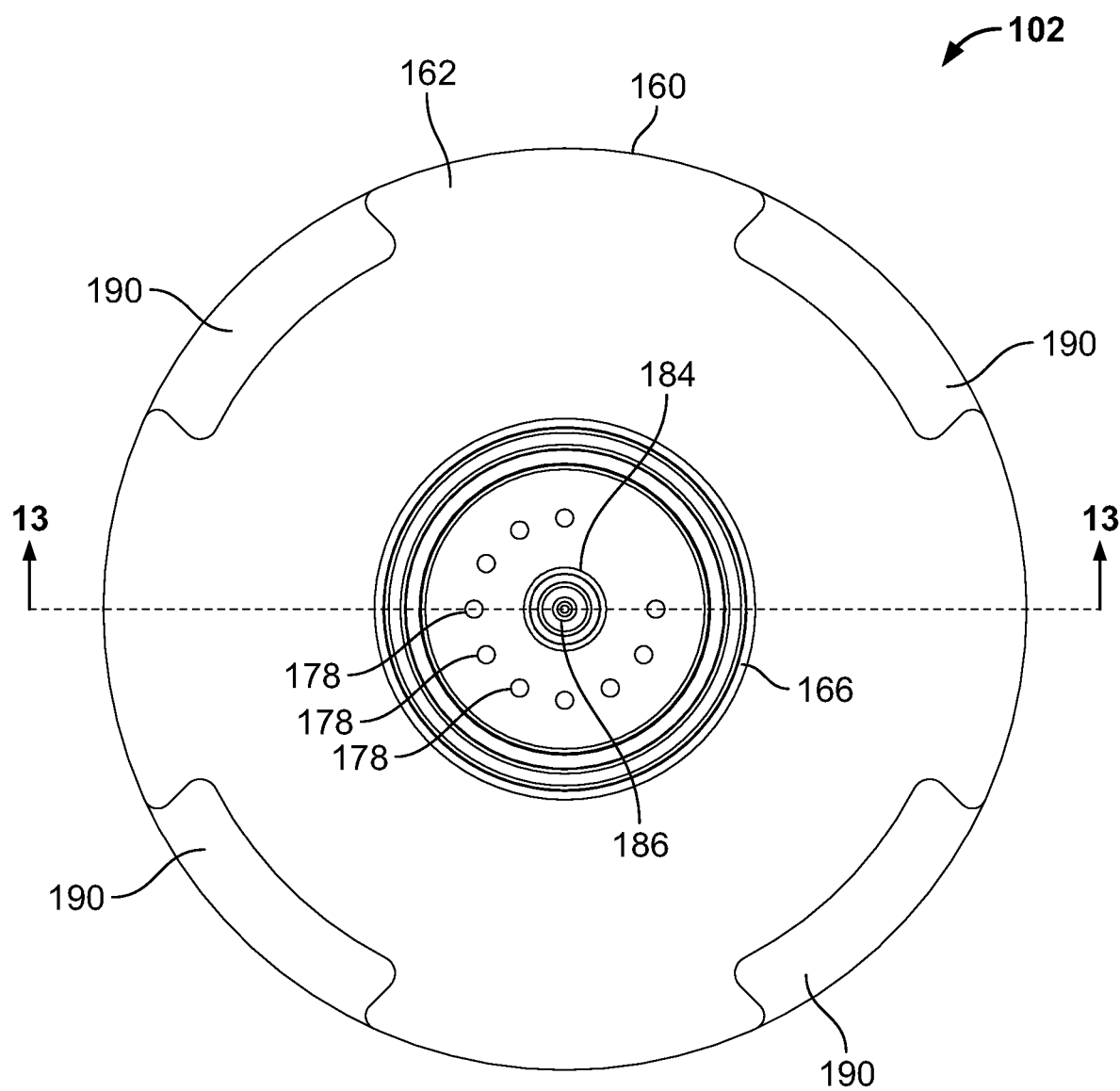
FIG. 11 is a top view of a plenum component of the plenum assembly.
Figure 12:
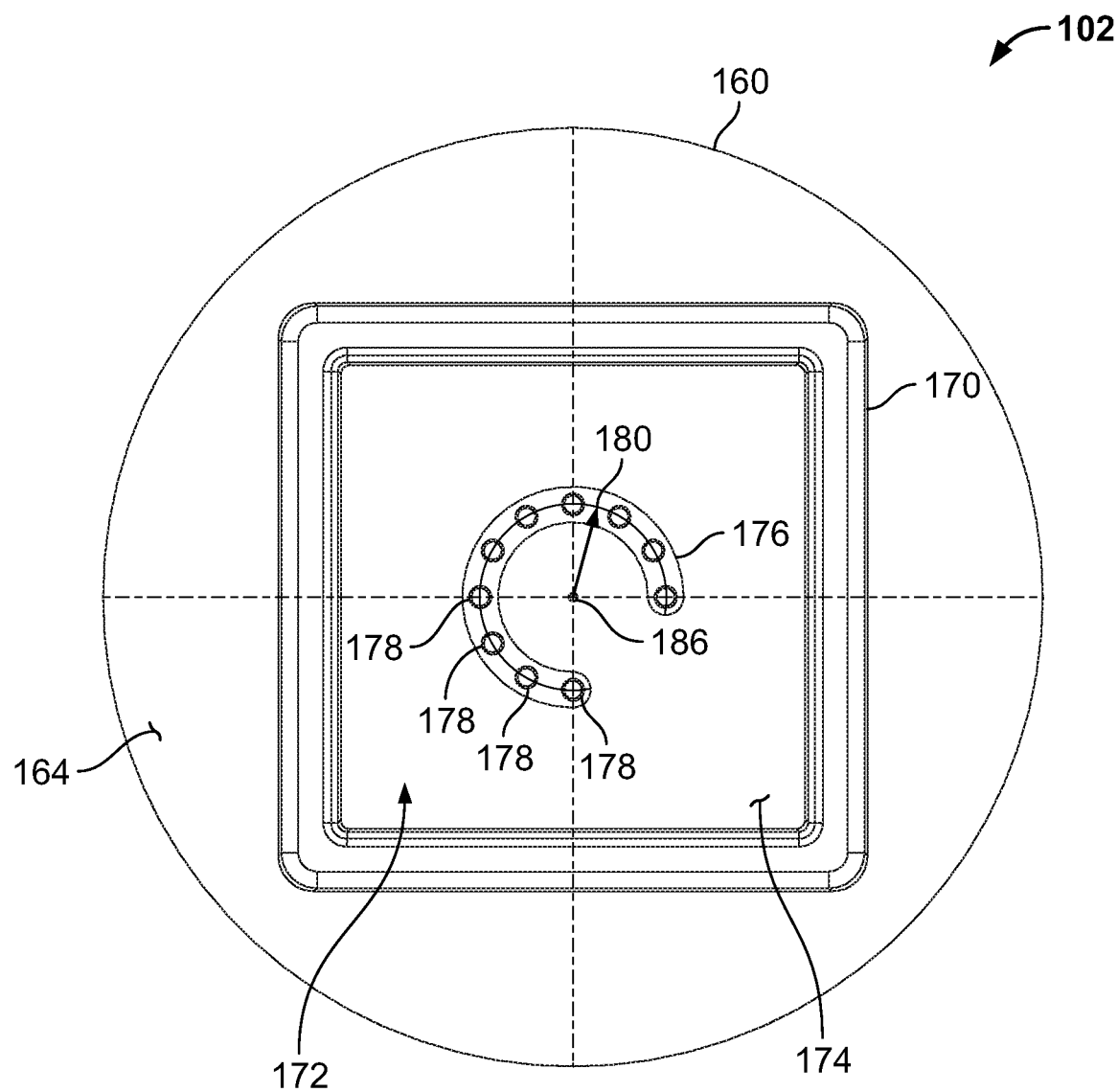
FIG. 12 is a bottom view of the plenum component.
Figure 13:
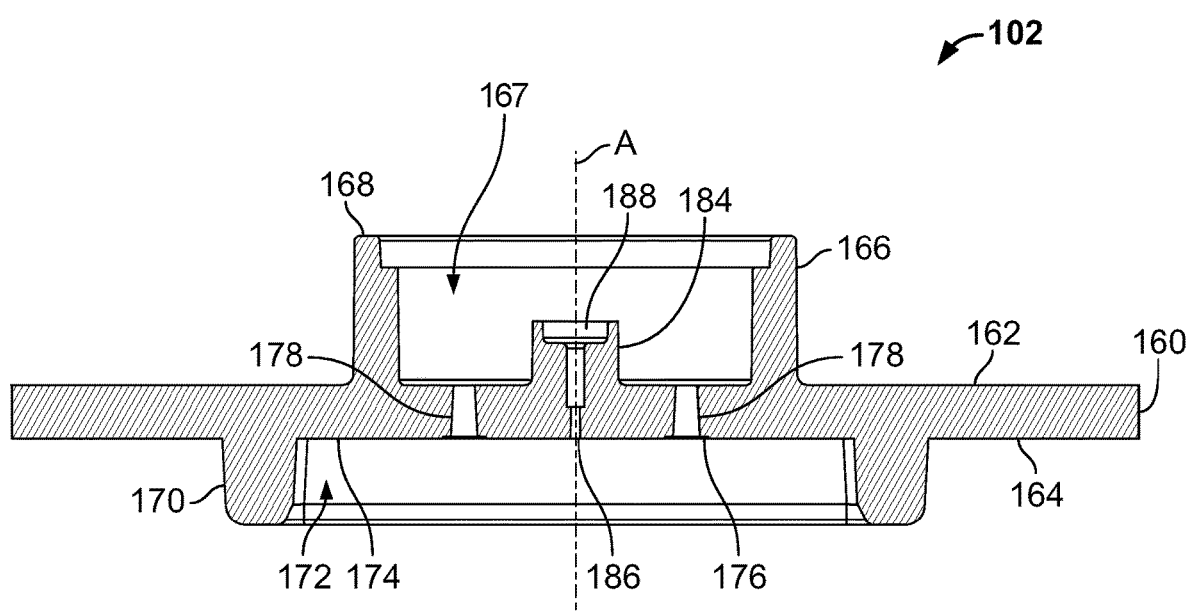
FIG. 13 is a section view of the plenum component taken about line 13-13 shown in FIG. 11.

FIG. 11 is a top view of the plenum component 102, FIG. 12 is a bottom view of the plenum component 102, and FIG. 13 is a section view of the plenum component 102 taken about line 13-13 shown in FIG. 11. Referring to FIGS. 5, 6, and 11-13, in the exemplary embodiment, the plenum component 102 includes a generally planar annular disk body portion 160 that extends horizontally across the lower wall portion 112 of the sleeve component 100 adjacent the bottom surface 136 to define the cavity 110. The body includes an upper surface 162 (FIG. 11) and an opposite lower surface 164 (FIG. 12). The upper surface 162 of the plenum component 102 has an upwardly extending annular central wall 166 positioned proximate a central portion of the body portion 160 and defining a chamber 167. The annular central wall 166 includes an upper rim 168 that is configured to couple to the cartridge assembly 18. The lower surface 164 of the plenum component 102 includes a rectangular frame portion 170 that extends downwardly from the body portion 160. The frame portion 170 defines a mounting space 172 for coupling the plenum cap assembly 106 and the microneedle array assembly 108 to a mounting surface 174 located within the mounting space 172.

The plenum component 102 includes an arcuate channel 176 having a plurality of axially extending apertures 178 defined therein. In particular, as best illustrated in FIG. 12, the arcuate channel 176 is defined in the mounting surface 174 within the mounting space 172. The arcuate channel 176 has a predetermined width that is centered about a center radius 180. The center radius 180 is concentric with the central axis "A" of the plenum component 102. In the exemplary embodiment, the arcuate channel 176 extends circumferentially about 270°. In other embodiments, the arcuate channel 176 can extend any circumferential angle that enables the plenum component 102 to function as described herein. In the exemplary embodiment, the axially extending apertures 178 are uniformly disposed in the arcuate channel 176. Each aperture 178 is centered on the center radius 180 and extends through the body portion 160 from the lower surface 164 to the upper surface 162. In the exemplary embodiment, the plenum component 102 includes ten axially extending apertures 178. Alternatively, in other suitable embodiments, the plenum component 102 can include any number of axially extending apertures 178 that enables the plenum component 102 to function as described herein.

In the exemplary embodiment, as best shown in FIG. 5, the cannula 104 is coupled to a mount 184 that extends upwardly from the upper surface 162 of the plenum component 102. In particular, the cannula 104 is coupled in fluid communication to a fluid passage 186 that extends through the plenum component 102, coaxial with the central axis "A." The cannula 104 is coupled to the plenum component 102 via an interference fit with the mount 184 and an adhesive disposed in a cavity 188 defined in the mount 184. As used herein, the phrase "interference fit" means a value of tightness between the cannula 104 and the mount 184, i.e., an amount of radial clearance between the components. A negative amount of clearance is commonly referred to as a press fit, where the magnitude of interference determines whether the fit is a light interference fit or interference fit. A small amount of positive clearance is referred to as a loose or sliding fit. Alternatively, the cannula 104 may be coupled to the mount 184 using any suitable fastening technique that enables the plenum component 102 to function as described herein. In the exemplary embodiment, an upper portion the cannula 104 is sharply pointed and extends upwardly away from the plenum component 102, such that the cannula 104 can pierce a portion of the cartridge assembly 18, as is described herein.

Referring to FIG. 11, the plenum component 102 includes a plurality of recesses 190 defined in the upper surface 162 and positioned equidistant about the central axis "A." The recesses 190 are sized and shaped to correspond to the flange members 134 of the sleeve component 100, as described above. Specifically, in the exemplary embodiment, the plenum component 102 includes four recesses 190 shown in the figures, however, it is noted that in other embodiments, the plenum component 102 has any number of recesses 190 that enables the plenum component 102 to function as described herein. As described herein, the sleeve component 100 is coupled to the plenum component 102 for example, and without limitation, via an adhesive bond, a weld joint (e.g., spin welding, ultrasonic welding, laser welding, or heat staking), and the like. In particular, the flange members 134 of the sleeve component 100 are coupled to the recesses 190 of the plenum component 102 to form a unitary assembly.

Figure 14:
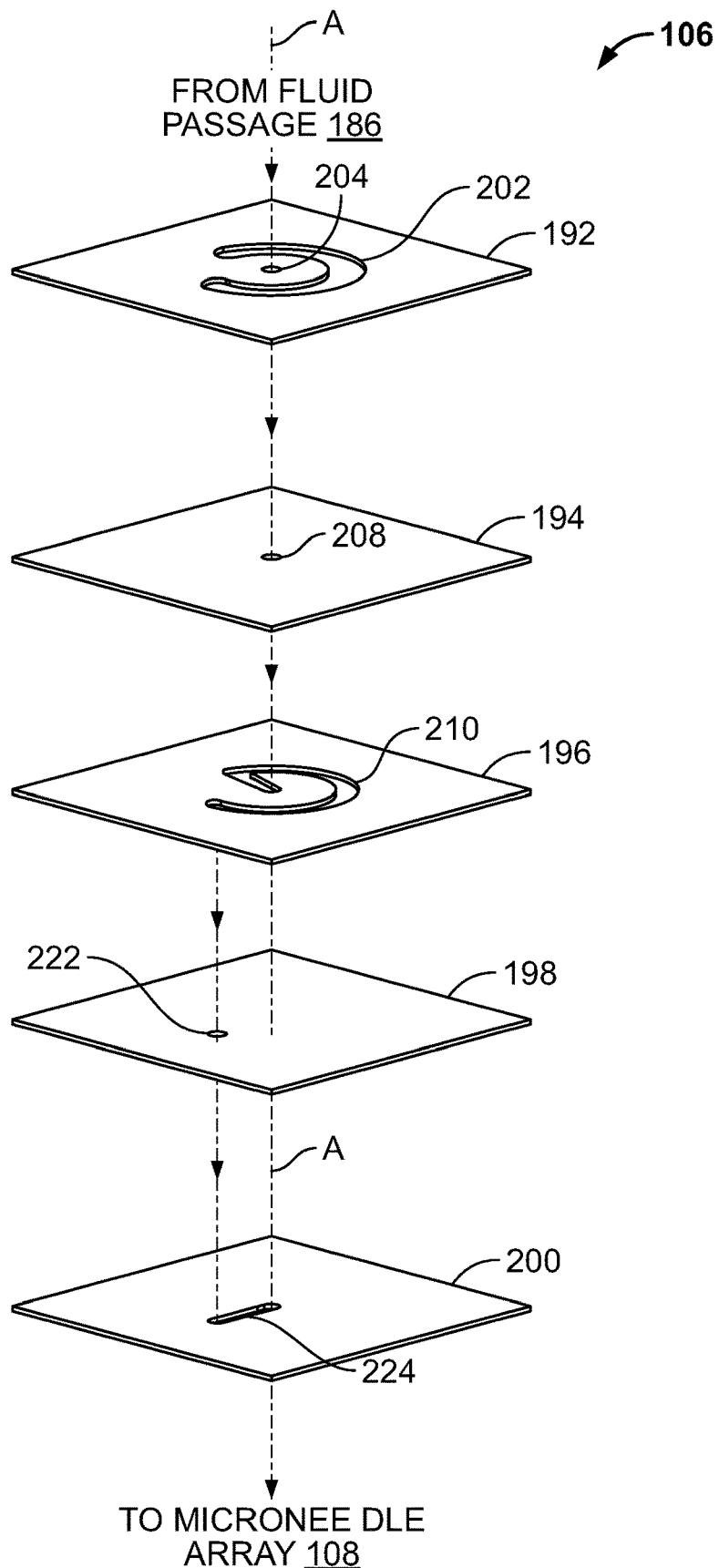
FIG. 14 is an exploded, schematic of a plenum cap assembly of the fluid delivery apparatus.
Figure 15:
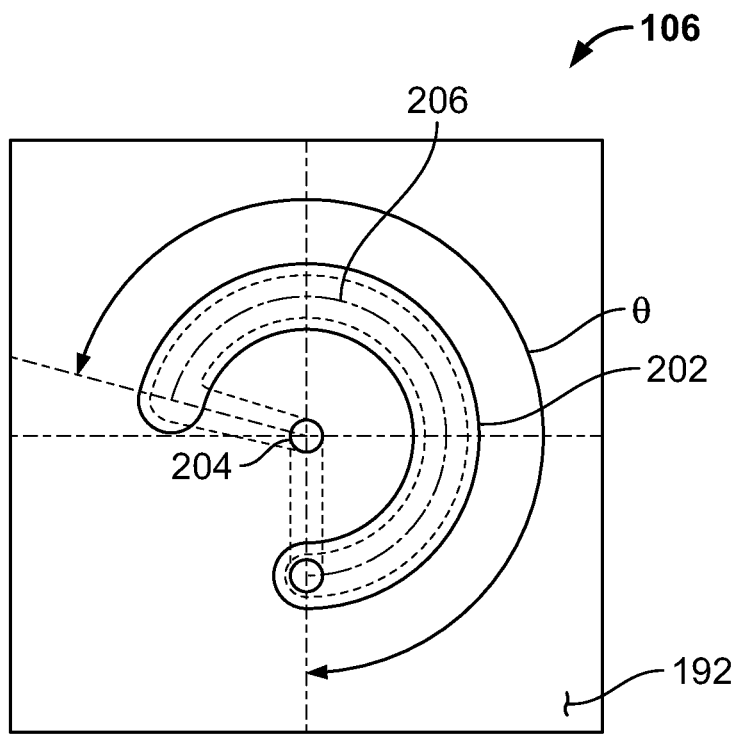
FIG. 15 is a top view of the plenum cap assembly, showing a first adhesive layer.

FIG. 14 is an exploded, schematic of the plenum cap assembly 106 of the fluid delivery apparatus 10 shown in FIG. 1A. FIG. 15 is a top view of the plenum cap assembly 106. In the exemplary embodiment, the plenum cap assembly 106 is a unitary assembly comprising a plurality of layers bonded together. The plenum cap assembly 106 is bonded to the mounting surface 174 of the plenum component 102 via a first adhesive layer 192, which is fabricated from pressure-sensitive adhesive film. The first adhesive layer 192 includes an arcuate slot 202 defined therethrough. The arcuate slot 202 is positioned substantially concentric with an aperture 204 formed coaxial with the central axis "A." The arcuate slot 202 has a predetermined width that is centered about a center radius 206. The center radius 206 is concentric with the central axis "A." In the exemplary embodiment, the arcuate slot 202 extends circumferentially at an angle θ. In other embodiments, the arcuate slot 202 can extend any circumferential angle θ that enables the plenum cap assembly 106 to function as described herein. In the exemplary embodiment, the arcuate slot 202 is configured to at least partially correspond to the arcuate channel 176 of the plenum component 102 and the aperture 204 is positioned to correspond to the fluid passage 186.

The plenum cap assembly 106 includes a vent membrane 194 coupled to the first adhesive layer 192 opposite the plenum component 102. In the exemplary embodiment, the vent membrane 194 includes a fluid inlet aperture 208 formed coaxial with the central axis "A." In the exemplary embodiment, the aperture 208 is substantially the same size as the aperture 204 of the first adhesive layer 192. In one suitable embodiment, the vent membrane 194 is fabricated from a gas permeable oleophobic/hydrophobic material. It is understood that other types of suitable materials can be used in other embodiments. For example, and without limitation, in one embodiment, the vent membrane 194 is fabricated from an acrylic copolymer membrane formed on a nylon support material, such as Versapor® R Membrane available from Pall Corporation in Port Washington, N.Y. In the exemplary embodiment, the pore size of vent membrane 194 is about 0.2 microns. The vent membrane 194 has a flow rate for air in the range between about 200 milliliters/minute/centimeter$^2$ (mL/min/cm$^2$) and about 2000 mL/min/cm$^2$), as measured at about 150 kilopascal (kPa). In addition, the vent membrane 194 has a minimum fluid bubble pressure in the range between about 35 kilopascal (kPa) and about 300 kPa. In one suitable embodiment, the vent membrane 194 has a flow rate for air of at least 250 mL/min/cm$^2$, as measured at about 150 kPa, and a minimum fluid bubble pressure of at least 150 kPa. Alternatively, the vent membrane 194 can be fabricated from any gas permeable material that enables the plenum cap assembly 106 to function as described herein.

Figure 16:
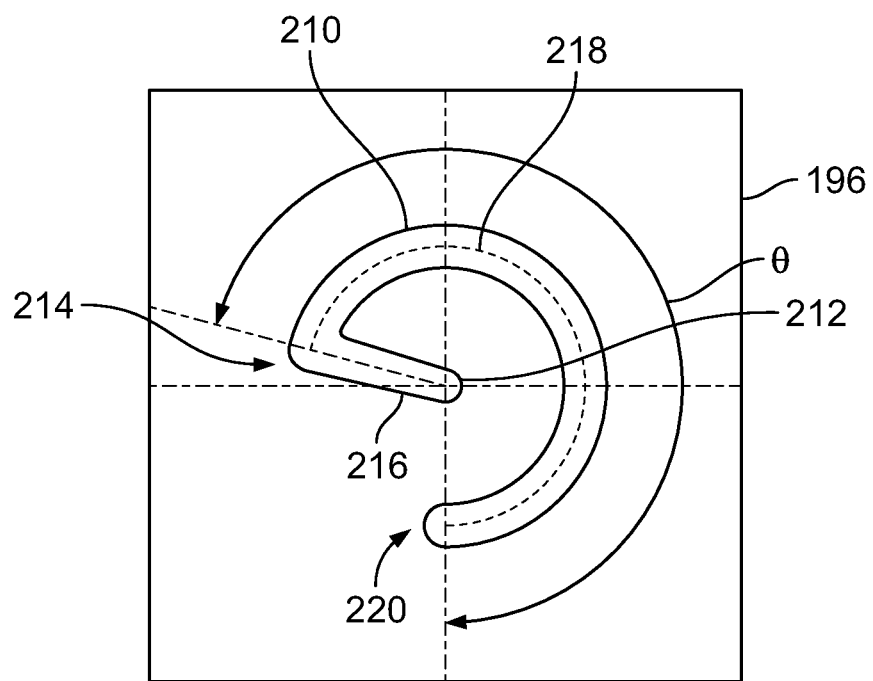
FIG. 16 is a top view of a second adhesive layer of the plenum cap assembly.

FIG. 16 is a top view of a second adhesive layer 196 of the plenum cap assembly 106. In the exemplary embodiment, the second adhesive layer 196 is formed from a pressure-sensitive adhesive film and is coupled to the vent membrane 194 opposite the first adhesive layer 192. The second adhesive layer 196 is formed similarly to the first adhesive layer 192 and includes an arcuate slot 210 defined therethrough. The arcuate slot 210 is configured to form a tortuous flow path that extends generally perpendicular to the central axis "A" to facilitate removing gas from the fluid. The arcuate slot 210 is sized and positioned to substantially correspond to the slot 202 of the first adhesive layer 192. The slot 210 is positioned concentric with a central aperture portion 212, which is formed coaxial with the central axis "A." A first end 214 of the arcuate slot 210 is connected to the central aperture portion 212 with a linear slot portion 216. The arcuate slot 210 has a predetermined width that is centered about a center radius 218, which corresponds to the center radius 206 of the first adhesive layer 192. In the exemplary embodiment, the arcuate slot 210 extends circumferentially at the same angle θ as the arcuate slot 202. In other embodiments, the arcuate slot 210 can extend any circumferential angle that enables the plenum cap assembly 106 to function as described herein.

Figure 17:
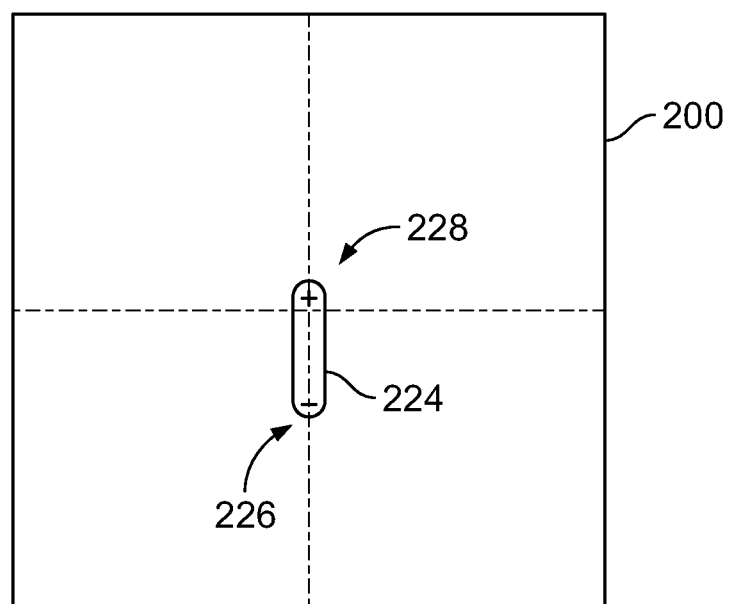
FIG. 17 is a top view of a third adhesive layer of the plenum cap assembly.

The plenum cap assembly 106 includes an impermeable membrane 198 coupled to the second adhesive layer 196 opposite the vent membrane 194. In the exemplary embodiment, the impermeable membrane 198 includes a fluid aperture 222 formed coaxial with a second end 220 of the arcuate slot 210. In the exemplary embodiment, the aperture 222 is substantially the same size as the apertures 204, 208 of the first adhesive layer 192 and the vent membrane 194, respectively. The impermeable membrane 198 is fabricated from a gas and liquid impermeable material. For example, and without limitation, in one embodiment, the impermeable membrane 198 is fabricated from a polyethylene terephthalate (PET) film. Alternatively, the impermeable membrane 198 can be fabricated from any gas and liquid impermeable material that enables the plenum cap assembly 106 to function as described herein FIG. 17 is a top view of a third adhesive layer 200 of the plenum cap assembly 106. In the exemplary embodiment, the third adhesive layer 200 is formed from a pressure-sensitive adhesive film and is coupled to the impermeable membrane 198 opposite the second adhesive layer 196. The third adhesive layer 200 includes a slot 224 defined therethrough. The slot 224 includes a first end 226 that is sized and positioned to substantially correspond to the aperture 222 of the impermeable membrane 198. In addition the slot extends from the first end 226 to a second end 228, which includes a full radius end sized substantially similar to the apertures 204, 208 of the first adhesive layer 192 and the vent membrane 194, respectively. Moreover, the second end 228 is positioned substantially coaxial with the central axis "A."

Figure 18:
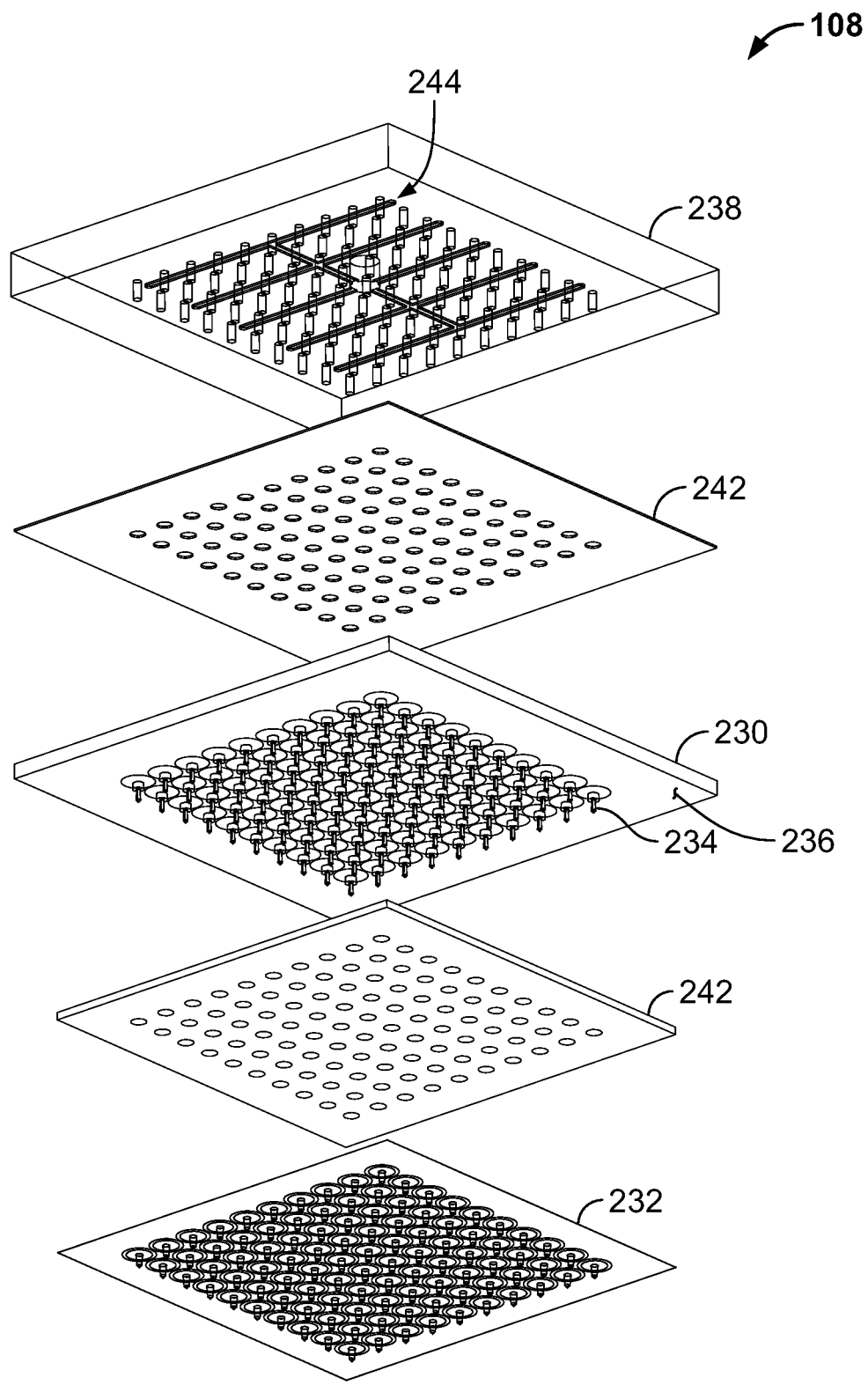
FIG. 18 is an exploded, schematic of a microneedle array assembly of the fluid delivery apparatus.
Figure 19A:
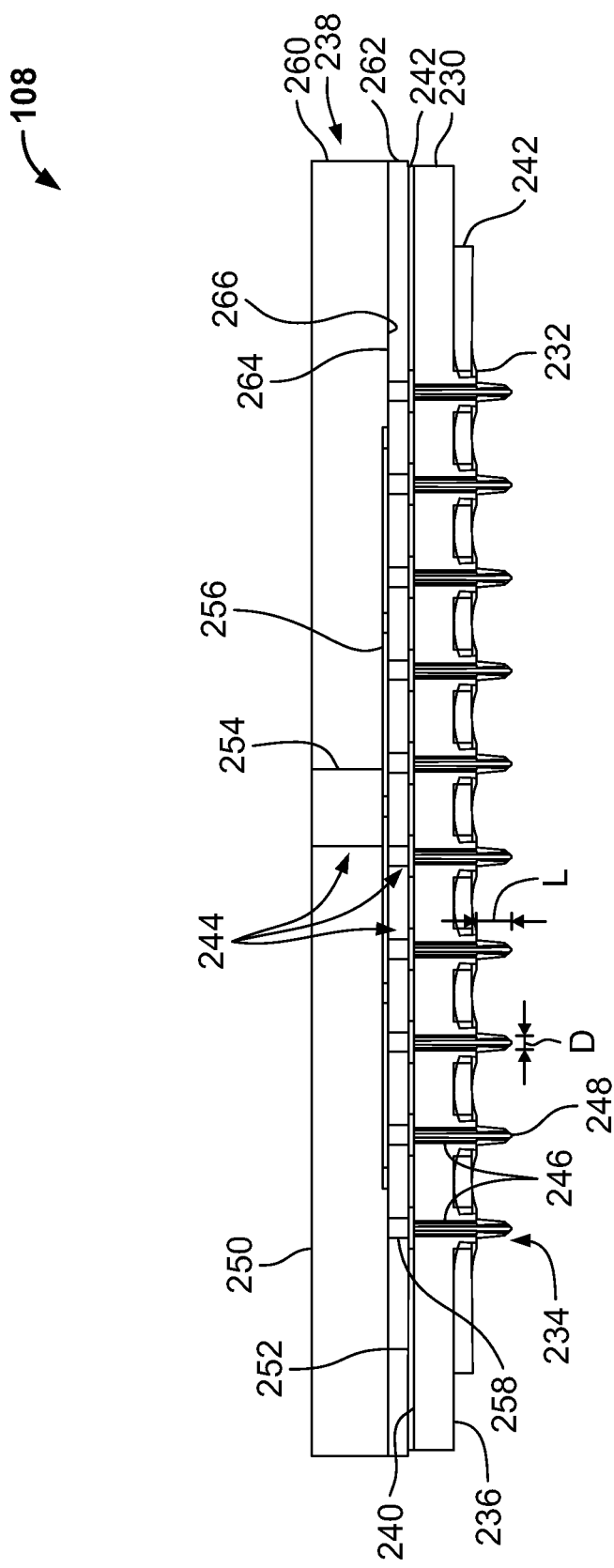
FIG. 19A is a schematic cross-sectional view of the microneedle array assembly.

As described herein with respect to FIGS. 5 and 6, the plenum assembly 16 includes the microneedle array assembly 108 coupled to the plenum cap assembly 106, which is mounted to the mounting surface 174 of the plenum component 102. FIG. 18 is an exploded, schematic of the microneedle array assembly 108 of the fluid delivery apparatus 10 shown in FIG. 1A. FIG. 19A is a schematic cross-sectional view of the microneedle array assembly 108. In the exemplary embodiment, the microneedle array assembly 108 is bonded to the plenum cap assembly 106 via the third adhesive layer 200 of the plenum cap assembly 106. The microneedle array assembly 108 includes a microneedle array 230 and a membrane 232 draped at least partially across a plurality of microneedles 234 and a base surface 236 of the microneedle array 230. The microneedle array assembly 108 also includes a distribution manifold 238 that extends across a back surface 240 of the microneedle array 230 and is bonded thereto by an adhesive layer 242. The distribution manifold 238 includes a fluid distribution network 244 for providing a fluid to the microneedle array 230. The fluid supplied from the distribution manifold 238 may be in the form of a liquid drug formulation. The membrane-draped microneedles 234 are configured to penetrate a user's skin, such as for providing the liquid drug formulation into the user's skin by way of one or more passageways or apertures 246 formed in each microneedle 234.

In the exemplary embodiment, the draped membrane 232 may be fabricated from a polymeric (e.g., plastic) film, or the like, and coupled to the microneedle array 230 using an additional adhesive layer 242. In other embodiments, the draped membrane 232 may include an embossed or nano-imprinted, polymeric (e.g., plastic) film, or be fabricated from a polyether ether ketone (PEEK) film, or the draped membrane 232 may be any other suitable material, such as a polypropylene film. It is contemplated that the microneedle array assembly 108 may not include the draped membrane 232 in some embodiments.

In the exemplary embodiment, the microneedle array 230 may be fabricated from a rigid, semi-rigid, or flexible sheet of material, for example, without limitation, a metal material, a ceramic material, a polymer (e.g., plastic) material, or any other suitable material that enables the microneedle array 230 to function as described herein. For example, in one suitable embodiment, the microneedle array 230 may be formed from silicon by way of reactive-ion etching, or in any other suitable fabrication technique.

As illustrated in FIG. 19A, the microneedle array 230 includes the plurality of microneedles 234 that extend outwardly from the back surface 240 of the microneedle array 230. The microneedle array 230 includes a plurality of passageways 246 extending between the back surface 240 for permitting the fluid to flow therethrough. For example, in the exemplary embodiment, each passageway 246 extends through the microneedle array 230 as well as through the microneedle 234.

Each microneedle 234 includes a base that extends downwardly from the back surface 240 and transitions to a piercing or needle-like shape (e.g., a conical or pyramidal shape or a cylindrical shape transitioning to a conical or pyramidal shape) having a tip 248 that is distal from the back surface 240. The tip 248 of each microneedle 234 is disposed furthest away from the microneedle array 230 and defines the smallest dimension (e.g., diameter or cross-sectional width) of each microneedle 234. Additionally, each microneedle 234 may generally define any suitable length "L" between the base surface 236 of the microneedle array 230 to its tip 248 that is sufficient to allow the microneedles 234 to penetrate the user's skin, i.e., penetrate the stratum corneum and pass into the epidermis of a user. It may be desirable to limit the length L of the microneedles 234 such that the microneedles 234 do not penetrate through the inner surface of the epidermis and into the dermis, which may advantageously facilitate minimizing pain for the user. In the exemplary embodiment, each microneedle 234 has a length L of less than about 1000 micrometers (um), such as less than about 800 um, or less than about 750 um, or less than about 500 um (e.g., an overall length L ranging from about 200 um to about 400 um), or any other subranges therebetween. The overall length L of the microneedles 234 may vary depending on the location at which the fluid delivery apparatus 10 is being used on the user. For example, and without limitation, the overall length L of the microneedles 234 for a fluid delivery apparatus to be used on a user's leg may differ substantially from the overall length L of the microneedles 234 for a fluid delivery apparatus to be used on a user's arm. Each microneedle 234 may generally have any suitable aspect ratio (i.e., the length L over a cross-sectional width dimension D of each microneedle 234). The aspect ratio may be greater than 2, such as greater than 3 or greater than 4. In instances in which the cross-sectional width dimension (e.g., diameter) varies over the length of each microneedle 234, the aspect ratio may be determined based on the average cross-sectional width dimension.

The channels or passageways 246 of each microneedle 234 may be defined through the interior of the microneedles 234 such that each microneedle forms a hollow shaft, or may extend along an outer surface of the microneedles to form a downstream pathway that enables the fluid to flow from the back surface 240 of the microneedle array 230 and through the passageways 246, at which point the fluid may be delivered onto, into, and/or through the user's skin. The passageways 246 may be configured to define any suitable cross-sectional shape, for example, without limitation, a semi-circular or circular shape. Alternatively, each passageway 246 may define a non-circular shape, such as a "v" shape or any other suitable cross-sectional shape that enables the microneedles 234 to function as described herein.

The microneedle array 230 may generally include any suitable number of microneedles 234 extending from back surface 240. For example, in some suitable embodiments, the quantity of microneedles 234 included within the microneedle array 230 is in the range between about 10 microneedles per square centimeter ($cm^2$) to about 1,500 microneedles per $cm^2$, such as from about 50 microneedles per $cm^2$ to about 1250 microneedles per $cm^2$, or from about 100 microneedles per $cm^2$ to about 500 microneedles per $cm^2$, or any other subranges therebetween.

The microneedles 234 may generally be arranged in a variety of different patterns. For example, in some suitable embodiments, the microneedles 234 are spaced apart in a uniform manner, such as in a rectangular or square grid or in concentric circles. In such embodiments, the spacing of the microneedles 234 may generally depend on numerous factors, including, but not limited to, the length and width of the microneedles 234, as well as the amount and type of liquid formulation that is intended to be delivered through or along the microneedles 234.

Furthermore, in the exemplary embodiment, the fluid distribution network 244 includes, for example, a plurality of channels and/or apertures extending between a top surface 250 and a bottom surface 252 of the distribution manifold 238. The channels and/or apertures include a centrally-located inlet channel 254 coupled in flow communication with a plurality of supply channels 256 and the slot 224 formed in the third adhesive layer 200 of the plenum cap assembly 106 (shown in FIG. 14). In the exemplary embodiment, the supply channels 256 facilitate distributing a fluid supplied by the inlet channel 254 across an area of the distribution manifold 238. Each of the supply channels 256 is coupled in flow communication to a plurality of resistance channels (not shown). The resistance channels extend away from the supply channels 256 and are formed to facilitate an increase in the resistance of the fluid distribution network 244 to the flow of the fluid. Each resistance channel is coupled in flow communication to an outlet channel 258. As illustrated in FIG. 19A, each outlet channel 258 is aligned with a respective microneedle 234 for distributing the fluid through the microneedle passageways 246. In other embodiments, the resistance channel and channels 254, 256, and 258 may be formed in any configuration that enables the distribution manifold 238 to function as described herein.

In the exemplary embodiment, the distribution manifold 238 is formed by bonding a base substrate 260 including the inlet channel 254 formed through the substrate, and the supply channels 256 and the resistance channels formed in a bottom surface 264, to a cover substrate 262 including the outlet channels 258 formed therethrough. The inlet channel 254 may be formed in the substrate 260 by drilling, cutting, etching, and or any other manufacturing technique for forming a channel or aperture through substrate 260. In the exemplary embodiment, the supply channels 256 and the resistance channels are formed in the bottom surface 264 of the substrate 260 using an etching technique. For example, in one suitable embodiment, wet etching, or hydrofluoric acid etching, is used to form the supply channels 256 and the resistance channels. In another suitable embodiment, Deep Reactive Ion Etching (DRIE or plasma etching) may be used to create deep, high density, and high aspect ratio structures in substrate 260. Alternatively, the supply channels 256 and resistance channels can be formed in bottom surface 264 using any fabrication process that enables the distribution manifold 238 to function as described herein. In the exemplary embodiment, the outlet channels 258 are formed through the cover substrate 262 by drilling, cutting, etching, and or any other manufacturing technique for forming a channel or aperture through substrate 262.

In the exemplary embodiment, the base substrate 260 and the cover substrate 262 are bonded together in face-to-face contact to seal the edges of the supply channels 256 and the resistance channels of the distribution manifold 238. In one suitable embodiment, direct bonding, or direct aligned bonding, is used by creating a prebond between the two substrates 260, 262. The prebond can include applying a bonding agent to the bottom surface 264 of the substrate 260 and a top surface 266 of the cover substrate 262 before bringing the two substrates into direct contact. The two substrates 260, 262 are aligned and brought into face-to-face contact and annealed at an elevated temperature. In another suitable embodiment, anodic bonding is used to form the distribution manifold 238. For example, an electrical field is applied across the bond interface at surfaces 264 and 266, while the substrates 260, 262 are heated. In an alternative embodiment, the two substrates 260, 262 may be bonded together by using a laser-assisted bonding process, including applying localized heating to the substrates 260, 262 to bond them together.

In the exemplary embodiment, the base substrate 260 and the cover substrate 262 are fabricated from a glass material. Alternatively, the base substrate 260 and the cover substrate 262 may be fabricated from silicon. It is contemplated that the base substrate 260 and the cover substrate 262 may be fabricated from different materials, for example, substrate 260 may be fabricated from a glass and the substrate 262 may fabricated from silicon. In other embodiments, the base substrate 260 and the cover substrate 262 may be fabricated from any material and material combination that enables the distribution manifold 238 to function as described herein.

Figure 19B:
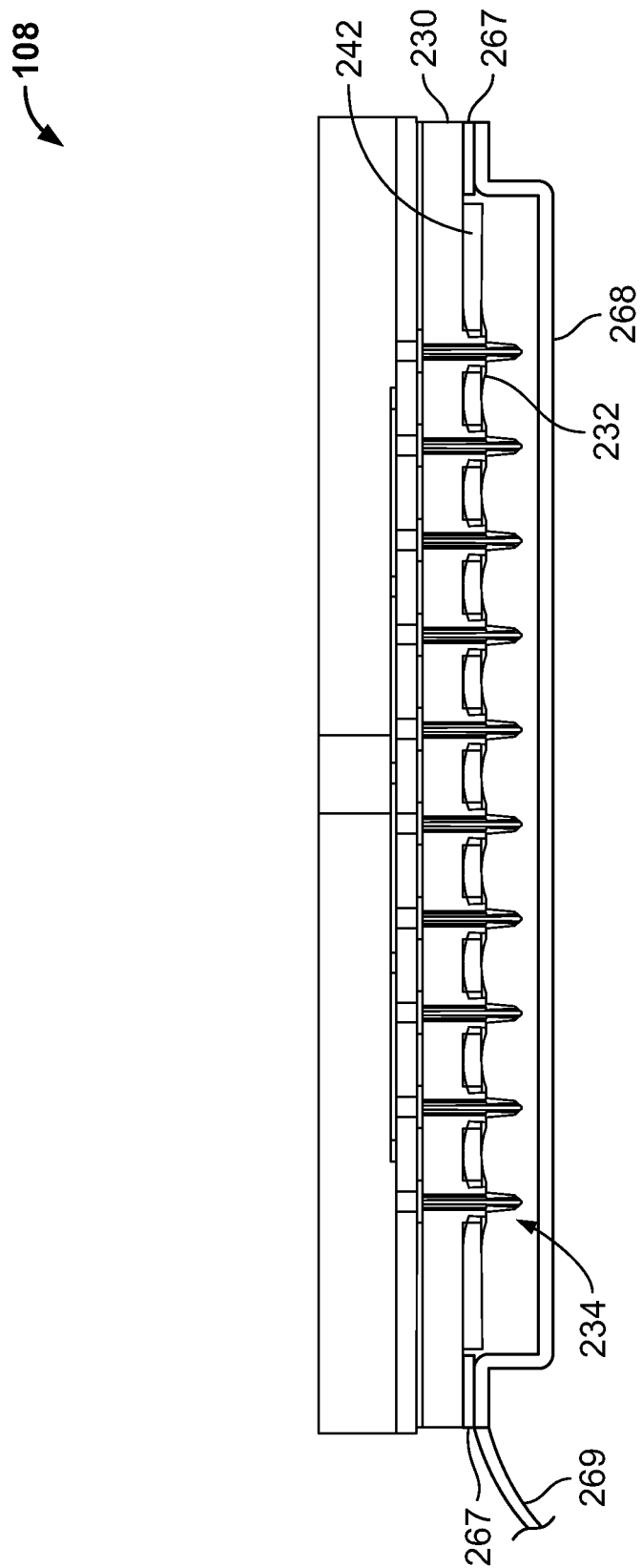
FIG. 19B is a schematic cross-sectional view of the microneedle array assembly of FIG. 19A but showing a protective cover covering the microneedle array assembly.

FIG. 19B is a schematic cross-sectional view of an alternative embodiment of the microneedle array assembly 108. In the exemplary embodiment, the microneedle array assembly 108 includes a protective cover 268 coupled to the microneedle array assembly 108 via an adhesive 267. The adhesive 267 may be attached to a periphery of the protective cover 268 to facilitate securing the protective cover 268 to the microneedle array assembly 108, and in particular, to the microneedle array 230. Alternatively, the adhesive layer 242 used to couple the draped membrane 232 to the microneedle array 230 may extend outward toward a periphery of the microneedle array 230 and may be used to attach the protective cover 268 to the microneedle array assembly 108. In the exemplary embodiment, the protective cover 268 may be fabricated from a material that is substantially impermeable to fluids, such as, for example, polymers, metal foils, and the like. The adhesive 267 may be a pressure-sensitive adhesive that includes, for example, solvent-based acrylic adhesives, solvent-based rubber adhesives, silicone adhesives, and the like as is known in the art. While the protective cover 268 is illustrated as a planar cover having a flanged peripheral sidewall, it is understood that it the protective cover 268 may be a flexible sheet material, such as a laminate. The protective cover 268 also includes at least one tab 269 that extends from an edge of the protective cover 268 beyond the adhesive 267 to facilitate removing (e.g., peeling) the protective cover away from the microneedle array assembly 108.

Figure 20:
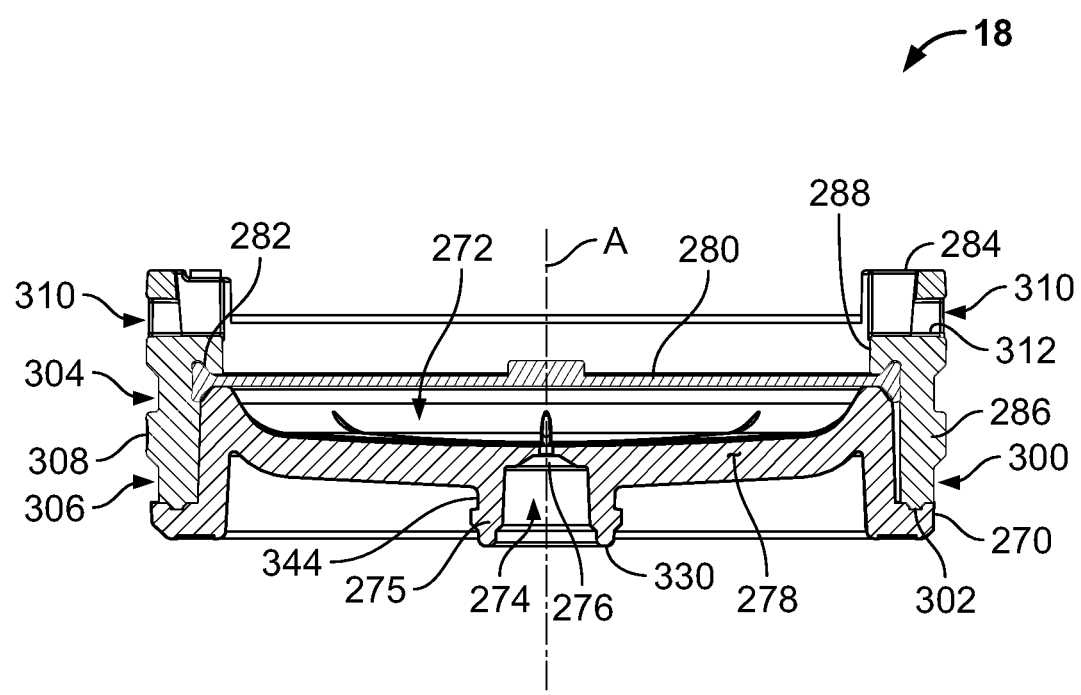
FIG. 20 is a sectional view of a cartridge assembly of the fluid delivery apparatus.
Figure 21:
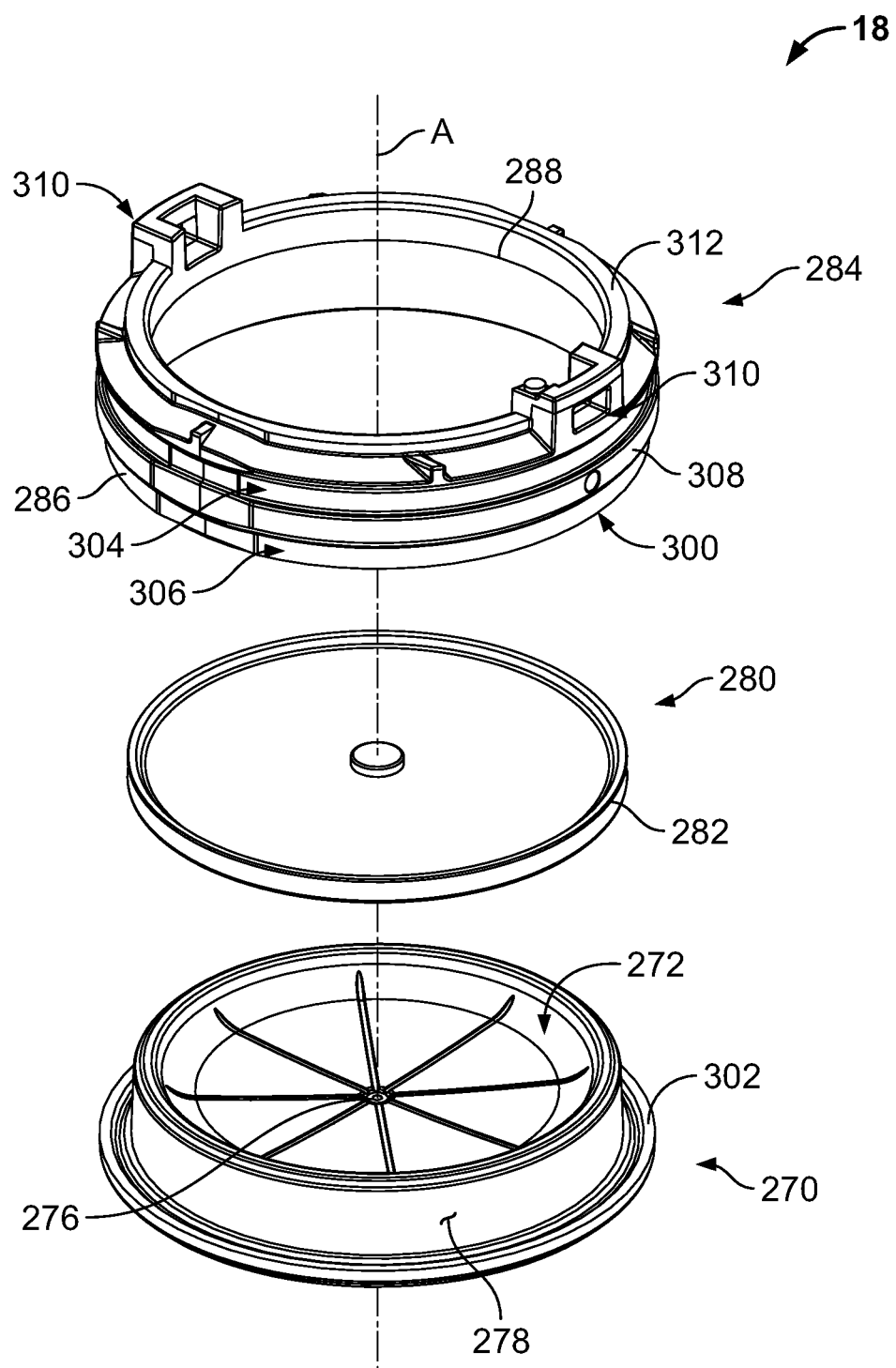
FIG. 21 is an exploded, schematic of the cartridge assembly.

FIG. 20 is a sectional view of the cartridge assembly 18 of the fluid delivery apparatus 10 shown in FIG. 1A. FIG. 21 is an exploded, schematic of the cartridge assembly 18. In the exemplary embodiment, the cartridge assembly 18 includes a reservoir component 270 formed generally concentric about the central axis "A." The reservoir component 270 includes an upper cavity 272 and an opposing lower cavity 274 coupled together in flow communication via a fluid passage 276. In the exemplary embodiment, the upper cavity 272 has a generally concave cross-sectional shape, defined by a generally concave body portion 278 of the reservoir component 270. The lower cavity 274 has a generally rectangular cross-sectional shape, defined by a lower wall 275 that extends generally vertically downward from a central portion of the concave body portion 278. An upper portion of the end of the fluid passage 276 is open at the lowest point of the upper cavity 272, and an opposite lower portion of the fluid passage 276 is open at a central portion of the lower cavity 274. The lower portion of the fluid passage 276 expands outward at the lower cavity 274, forming a generally inverse funnel cross-sectional shape. In other embodiments, the cross-sectional shapes of the upper cavity 272, the lower cavity 274, and the fluid passage 276 may be formed in any configuration that enables the reservoir component 270 to function as describe herein.

The cartridge assembly 18 also includes an upper sealing member 280 (or membrane) configured to couple to the reservoir component 270 and close the upper cavity 272. The upper sealing member 280 is formed as an annular sealing membrane and includes a peripheral ridge member 282 to facilitate sealingly securing the upper sealing member 280 to the cartridge assembly 18. A cartridge housing 284 extends over the upper sealing member 280 and is configured to fixedly engage the reservoir component 270. This facilitates securing the upper sealing member 280 in sealing contact with the reservoir component 270, thereby closing the upper cavity 272.

In the exemplary embodiment, the cartridge housing 284 includes a annular, vertically-extending wall 286 that has an inward extending flange member 288 configured to couple to the peripheral ridge member 282 of the upper sealing member 280. In particular, the flange member 288 cooperates with the concave body portion 278 of the reservoir component 270 to compress and sealingly secure the upper sealing member 280 therebetween. In the exemplary embodiment, a lower end 300 of the vertically-extending wall 286 is coupled to a flange 302 of the reservoir component 270 via welding, for example, and without limitation, ultrasonic welding, spin welding, laser welding, and/or heat staking. In other embodiments, the vertically-extending wall 286 may be coupled to a flange 302 using any connection technique that enables the cartridge housing 284 to fixedly engage the reservoir component 270, for example, and without limitation, via an adhesive bond and the like.

The cartridge housing 284 also includes an upper groove 304 and a lower groove 306 formed circumferentially in an outer surface 308 of the vertically-extending wall 286. The upper and lower grooves 304, 306 are sized and shaped to engage the plurality of flexible tabs 116 of the sleeve component 100, and, in particular, the radially inward extending protrusions 122 formed at the free second end 120 of the plurality of flexible tabs 116, as is described herein. In addition, the cartridge housing 284 also includes a plurality of latch receiving openings 310 formed on an upper edge portion 312 of the vertically-extending wall 286. The latch receiving openings 310 are configured to couple to the mechanical controller assembly 20 to secure it to the cartridge assembly 18, as described herein.

Figure 22:
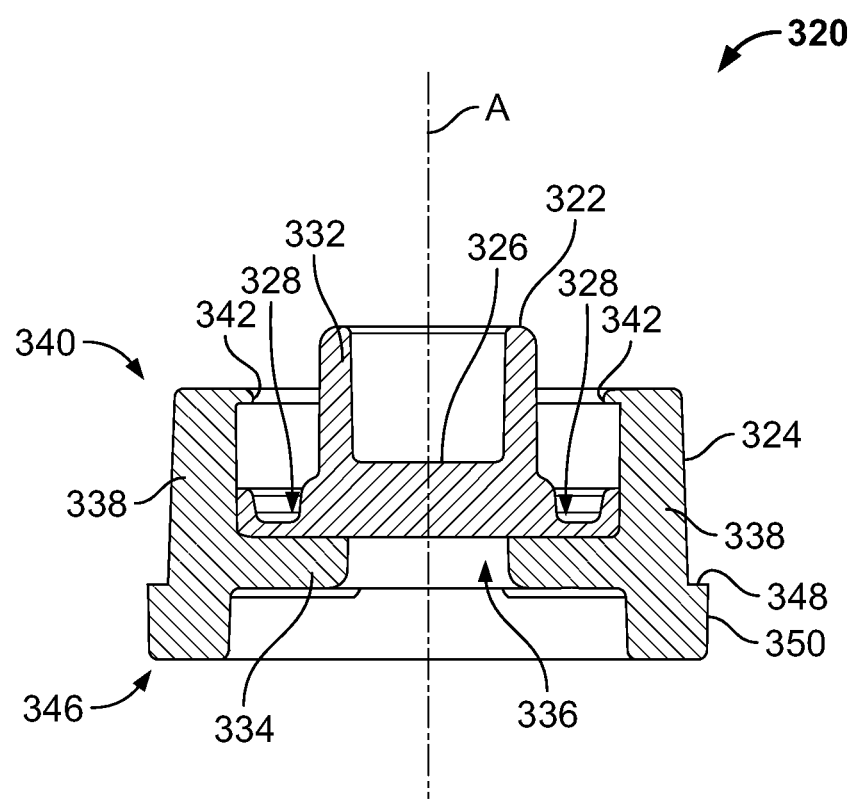
FIG. 22 is a sectional view of a cap assembly of the fluid delivery apparatus.

FIG. 22 is a sectional view of the cap assembly 320 of the fluid delivery apparatus 10 shown in FIG. 1A. In the exemplary embodiment, the cap assembly 320 includes a septum component 322 and a snap cap component 324 coupled together. The septum component 322 is configured to couple to the reservoir component 270 and close the lower cavity 274. The septum component 322 has a lower wall 326 that extends substantially perpendicular to the central axis "A." The lower wall 326 includes a peripheral channel 328 that is configured to sealingly engage a rim 330 of the lower wall 275 of the reservoir component 270. The septum component 322 also includes an annular upper seal wall 332, transverse to the lower wall 326, and that extends axially into the lower cavity 274 when coupled to the reservoir component 270. The snap cap component 324 extends over the septum component 322 and is configured to fixedly engage the lower wall 275 of the reservoir component 270. This facilitates securing the septum component 322 in sealing contact with the reservoir component 270, thereby sealingly closing the lower cavity 274.

The snap cap component 324 includes a lower wall 334 that has a central opening 336 to facilitate access to the lower wall 326 of the septum component 322 during use of the fluid delivery apparatus 10. The snap cap component 324 includes an annular vertically-extending wall 338 that extends upwardly and downwardly from a periphery of the lower wall 334. In the exemplary embodiment, an upper portion 340 of the vertically-extending wall 338 engages the lower wall 275 of the reservoir component 270 via a latching component 342. The latching component 342 includes an inwardly projecting flange for connecting with an opposing groove 344 formed in the lower wall 275 of the reservoir component 270. It is contemplated that the latching component 342 can be a continuous annular flange or may include a plurality of inwardly projecting flange components. In other embodiments, the vertically-extending wall 338 may engage the lower wall 275 of the reservoir component 270 using any connection technique that enables the snap cap component 324 to fixedly engage the lower wall 275, for example, and without limitation, via an interference fit, an adhesive bond, a weld joint (e.g., spin welding, ultrasonic welding, laser welding, or heat staking), and the like. In the exemplary embodiment, a lower portion 346 of the vertically-extending wall 275 includes an outwardly extending flange portion 348 that defines a peripheral sealing surface 350 configured to engage an additional seal member (not shown) that extends between the snap cap component 324 and the upper rim 168 of the annular central wall 166 of the plenum component 102.

Figure 23:
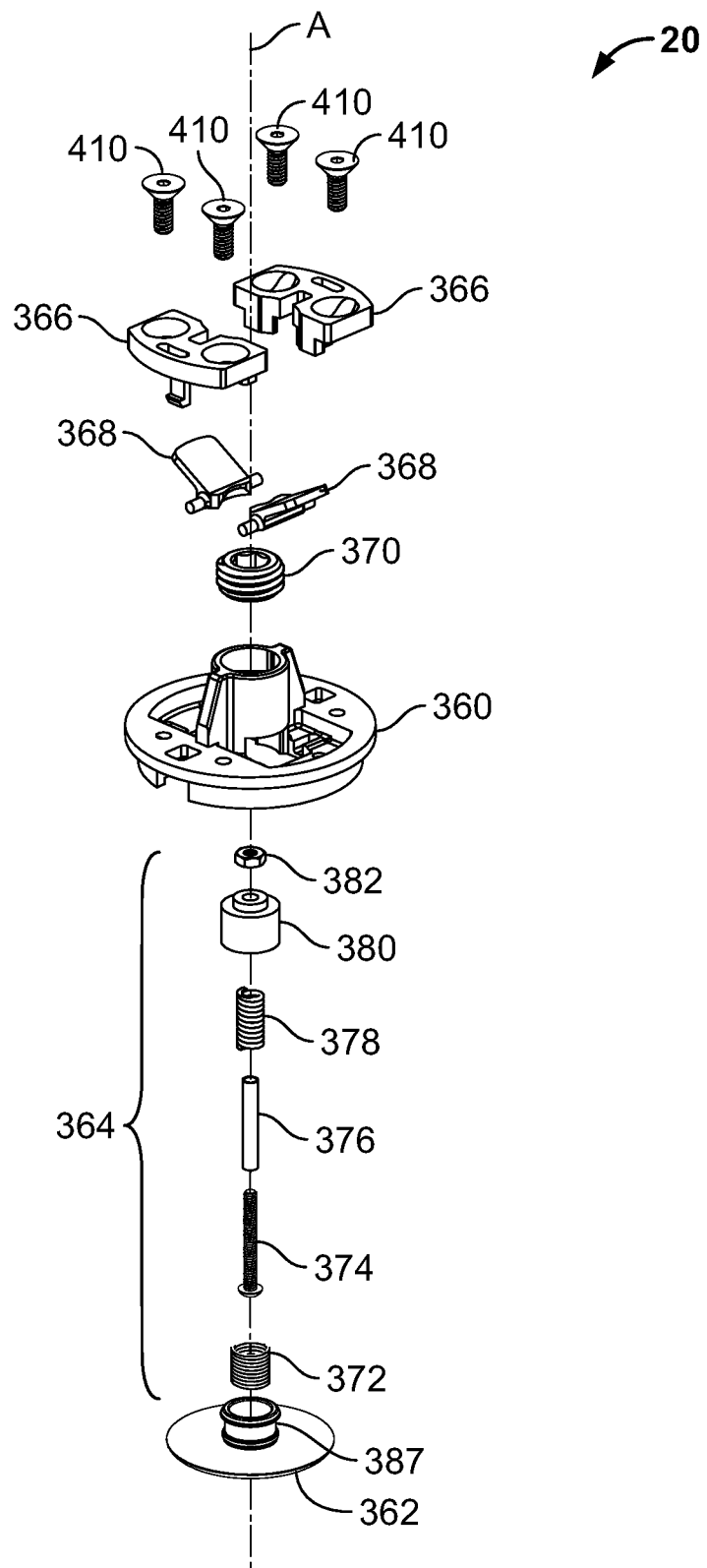
FIG. 23 is an exploded, perspective view of a mechanical controller assembly of the fluid delivery apparatus.

FIG. 23 is an exploded, perspective view of the mechanical controller assembly 20 of the fluid delivery apparatus 10 shown in FIG. 1A. In the exemplary embodiment, the mechanical controller assembly 20 includes at least a body component 360, a plunger component 362, and a biasing assembly 364 positioned between the body component 360 and the plunger component 362 for biasing the plunger component 362 in an axial direction away from the body component 360. The body component 360 includes a pair of retention plates 366 configured to couple a pair of pivoting latches 368 to the body component 360, and a threaded adjustment member 370 configured to adjust an amount of force applied by the biasing assembly 364 to the plunger component 362.

Figure 24:
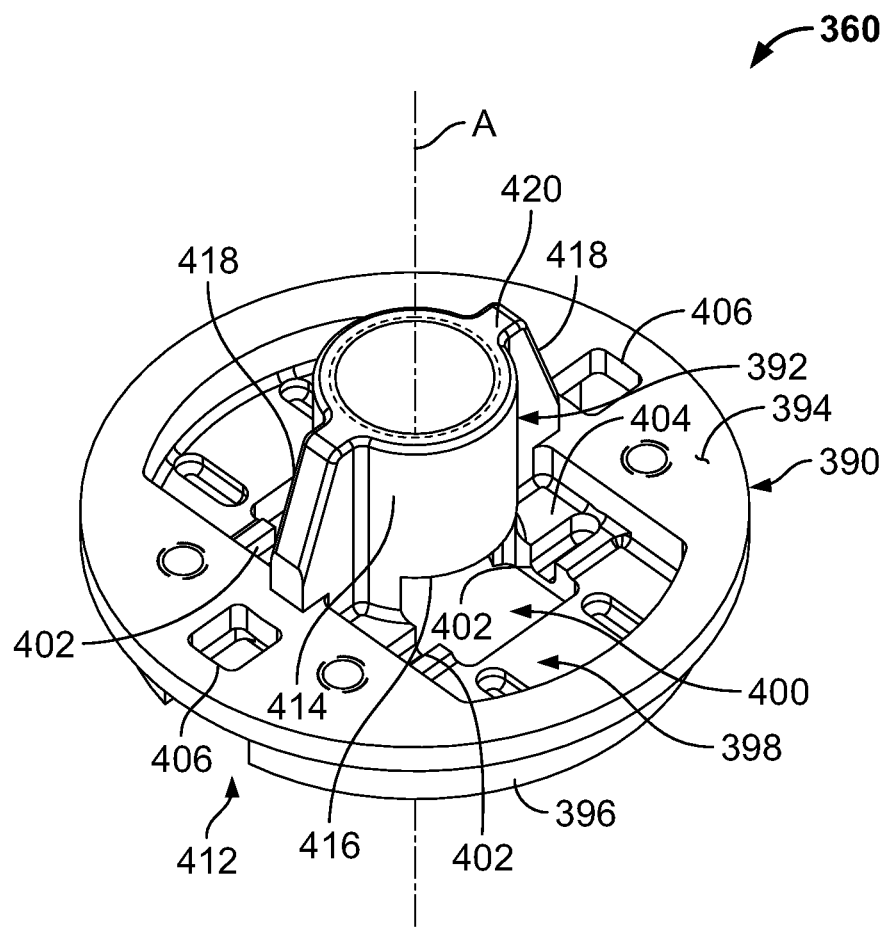
FIG. 24 is a perspective view of a body component of the mechanical controller assembly.
Figure 25:
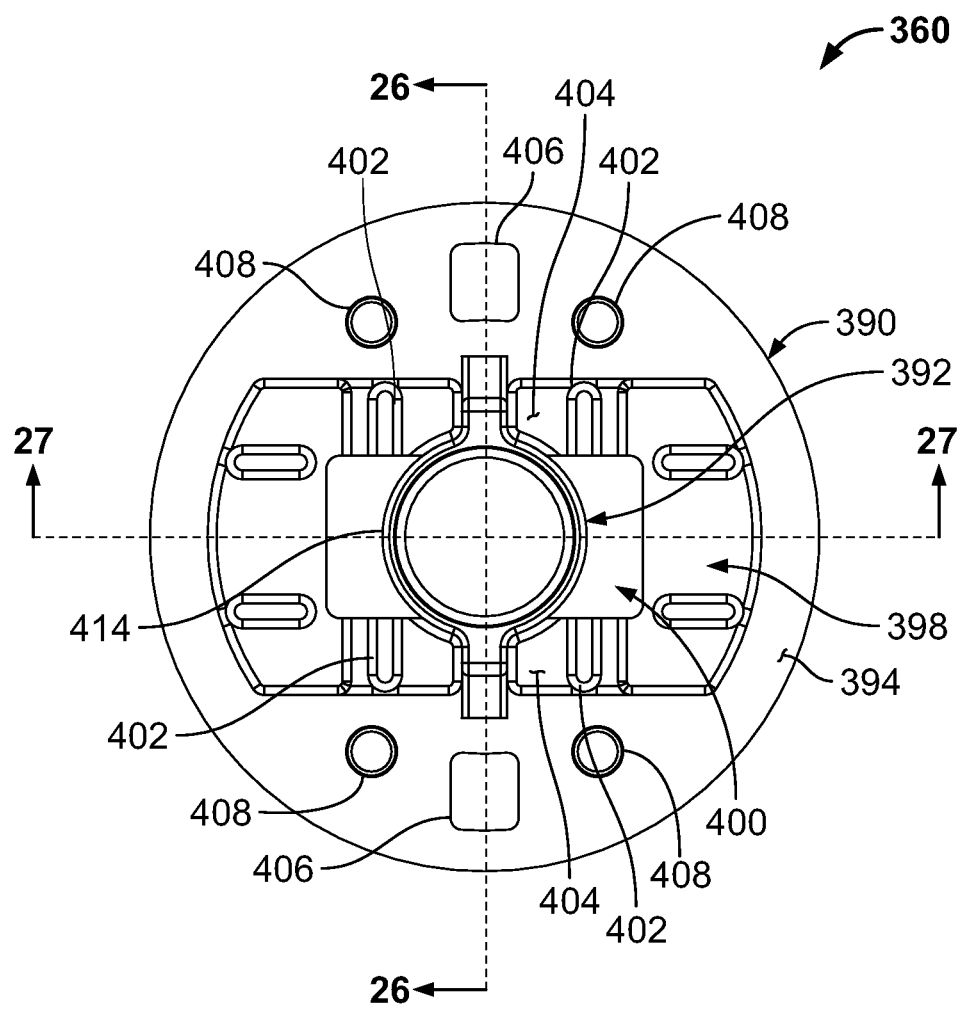
FIG. 25 is a top view of the body component.
Figure 26:
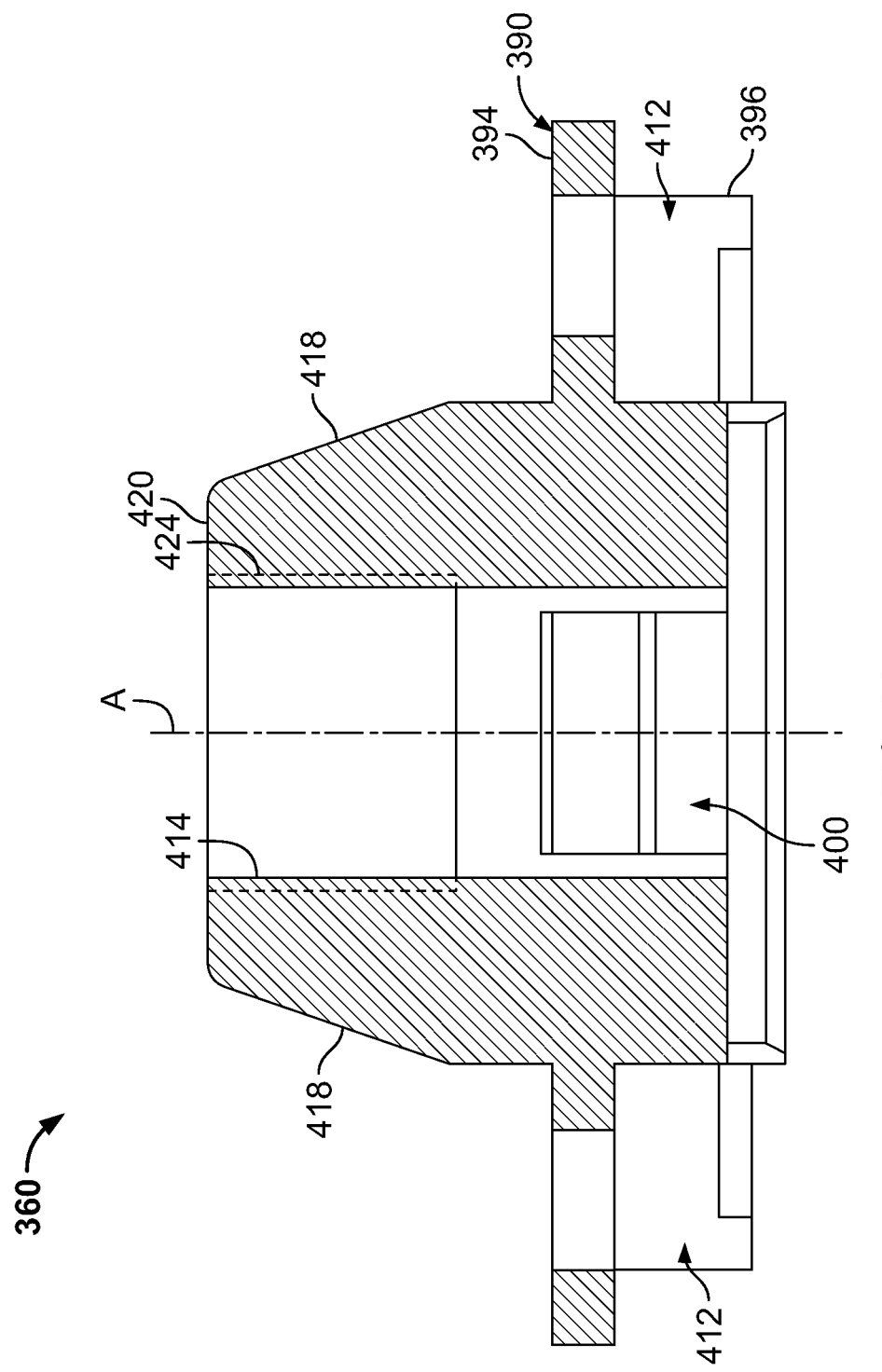
FIG. 26 is a sectional view of the body component taken about line 26-26 of FIG. 25.
Figure 27:
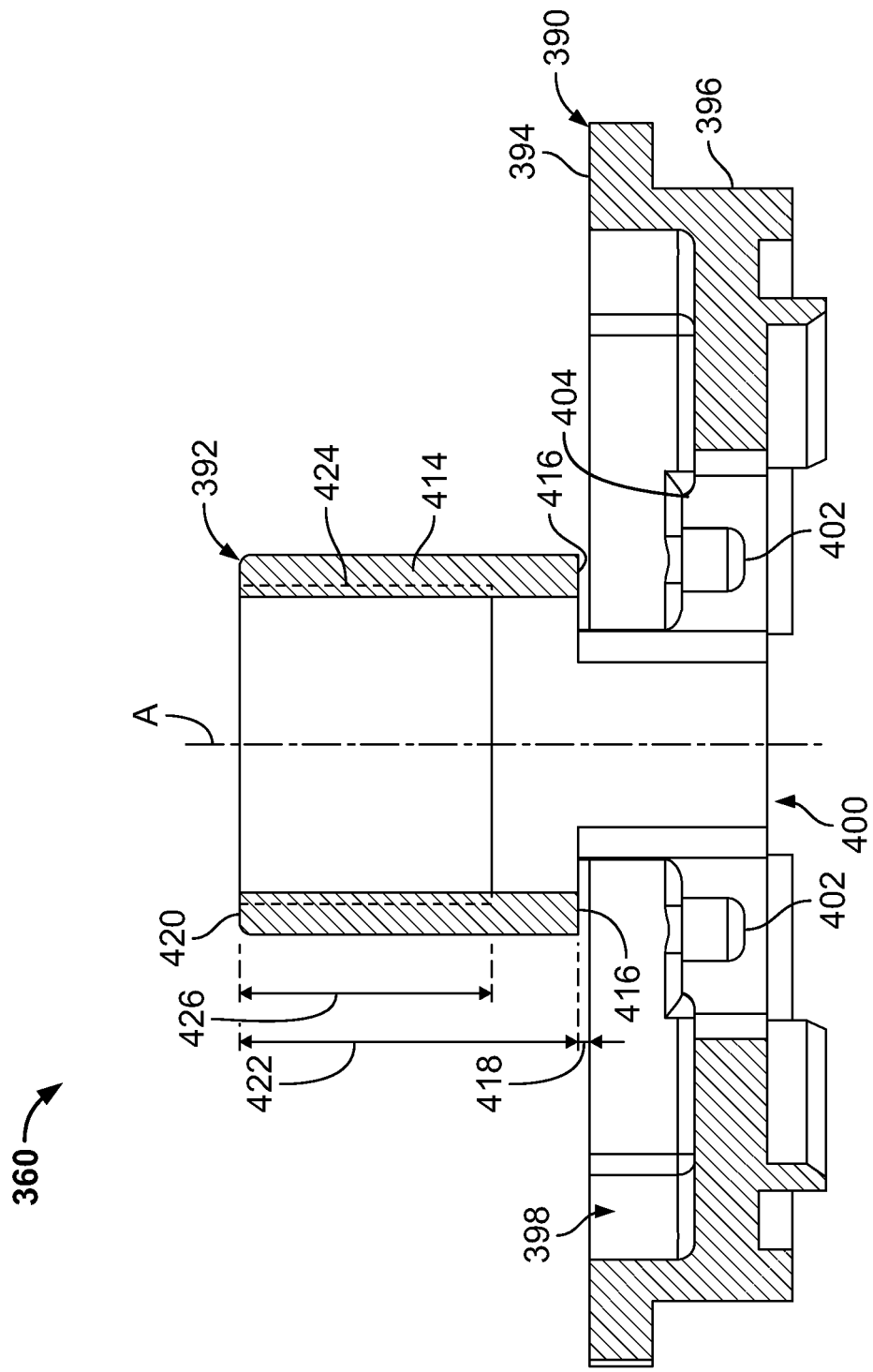
FIG. 27 is a sectional view of the body component taken about line 27-27 of FIG. 25.

FIG. 24 is a perspective view of the body component 360. FIG. 25 is a top view of the body component 360. FIG. 26 is a sectional view of the body component 360 taken about line 26-26 of FIG. 25. FIG. 27 is a sectional view of the body component 360 taken about line 27-27 of FIG. 25. In the exemplary embodiment, the body component 360 includes a generally disk-shaped outer body portion 390 and a generally cylindrical-shaped inner portion 392 extending upward from the outer body portion 390. The body component 360 is formed generally symmetrically about lines 26-26 and 27-27 as illustrated in the figures. The outer body portion 390 includes a transversely extending top wall 394 and an annular sidewall 396 depending from the top wall 394. The top wall 394 has a cavity 398 defined therein with a smaller central aperture 400 extending therethrough. In the exemplary embodiment, the cavity 398 and the aperture 400 are generally rectangular in shape. Alternatively, the cavity 398 and the aperture 400 can be any shape that enables the body component 360 to function as described herein. In the exemplary embodiment, the cavity 398 has a plurality of notches 402 defined therein for receiving the pivoting latches 368. In particular, the plurality of notches 402 includes two pairs and notches 402 generally aligned across the central aperture 400 and positioned generally symmetrically about line 26-26. As illustrated in FIGS. 24 and 27, the notches 402 extend downwardly into a bottom wall 404 of the cavity 398.

The top wall 394 includes a plurality of openings 406 defined therethrough and configured to receive a latch component of a respective retention plate 366. Positioned on either side of a respective opening 406 are threaded holes 408. The threaded holes 408 receive mechanical hardware 410 used to couple the retention plates 366 to the body component 360. As illustrated in FIGS. 24 and 26, the annular sidewall 396 includes cutouts 412 proximate each opening 406 to enable the latch components of the retention plates 366 to extend thereby, as described further herein.

In the exemplary embodiment, the cylindrical-shaped inner portion 392 includes an annular wall 414 that extends upwardly from the bottom wall 404 of the cavity 398, as best illustrated in FIGS. 24 and 26. In addition, as illustrated in FIGS. 24 and 27, the annular wall 414 has a bottom edge 416 over the central aperture 400 that is located a predetermined distance 418 above the top wall 394. Accordingly, a space is defined between the bottom wall 404 of the cavity 398 and the bottom edge 416 of the annular wall 414 to enable the pivoting latches 368 to engage the plunger component 362 as is described further herein.

The cylindrical-shaped inner portion 392 further includes a plurality of gusset portions 418 that extend from top wall 394 to a top edge 420 of annular wall 414. In particular, the body component 360 includes two symmetrically oriented gusset portions 418 that extend radially outward from annular wall 414 through the cavity 398 and into the top wall 394. In addition, the gusset portions 418 extend upwardly and taper radially inwardly from the top wall 394 to the top edge 420 of the annular wall 414. The gusset portions 418 are configured to provide additional structural support to the cylindrical-shaped inner portion 392 of the body component 360. Furthermore, as illustrated in FIG. 27, the annular wall 414 has a predetermined length 422 from the top edge 420 to the predetermined distance 418 above the top wall 394. The annular wall 414 includes a threaded portion 424 defined therein that extends downwardly from the top edge 420 a distance 426, where the distance 426 is less than the length 422 of the annular wall 414. This enables the threaded adjustment member 370 to be coupled to the body component 360, without being able to be threaded entirely through the cylindrical-shaped inner portion 392.

Figure 28:
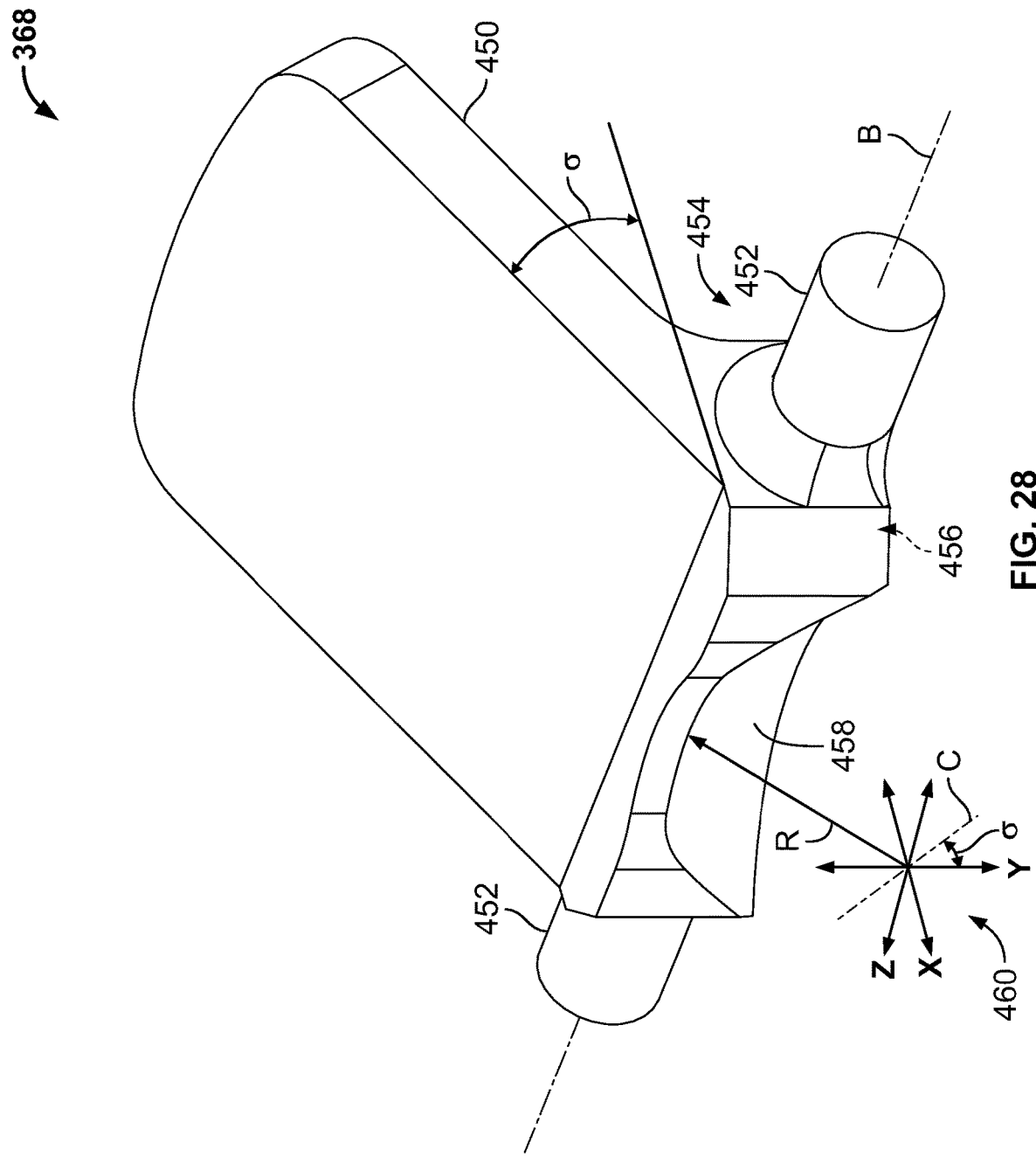
FIG. 28 is a perspective view of a pivoting latch of the mechanical controller assembly.

FIG. 28 is a perspective view of a pivoting latch 368 of the mechanical controller assembly 20. In the exemplary embodiment, the pivoting latch 368 is formed generally symmetrically about an X-Y plane defined by the axes 460. The pivoting latch 368 includes an elongated lever portion 450 that has a pair of cylindrical pins 452 coupled to an end portion 454 of the lever portion 450. A respective cylindrical pin 452 extends from each side of the lever portion 450 such that the cylindrical pins 452 are coaxial about a centerline "B." A latch portion 456 extends away from the lever portion 450 at the end portion 454. In particular, the latch portion 456 extends from the end portion 454 of the lever portion 450 at an angle σ with respect to the lever portion 450. The latch portion 456 includes a concave cutout 458 that extends through the latch portion 456. More specifically, the concave cutout 458 is defined by a radius "R" about a centerline "C." Centerline "C" is in the X-Y plane of the axes 460 and is inclined at the same angle σ as the latch portion 456 is with respect to the lever portion 450. As such, the concave cutout 458 extends through the latch portion 456 at angle σ, where the centerline "C" of the concave cutout 458 is substantially perpendicular to the lever portion 450.

Figure 29:
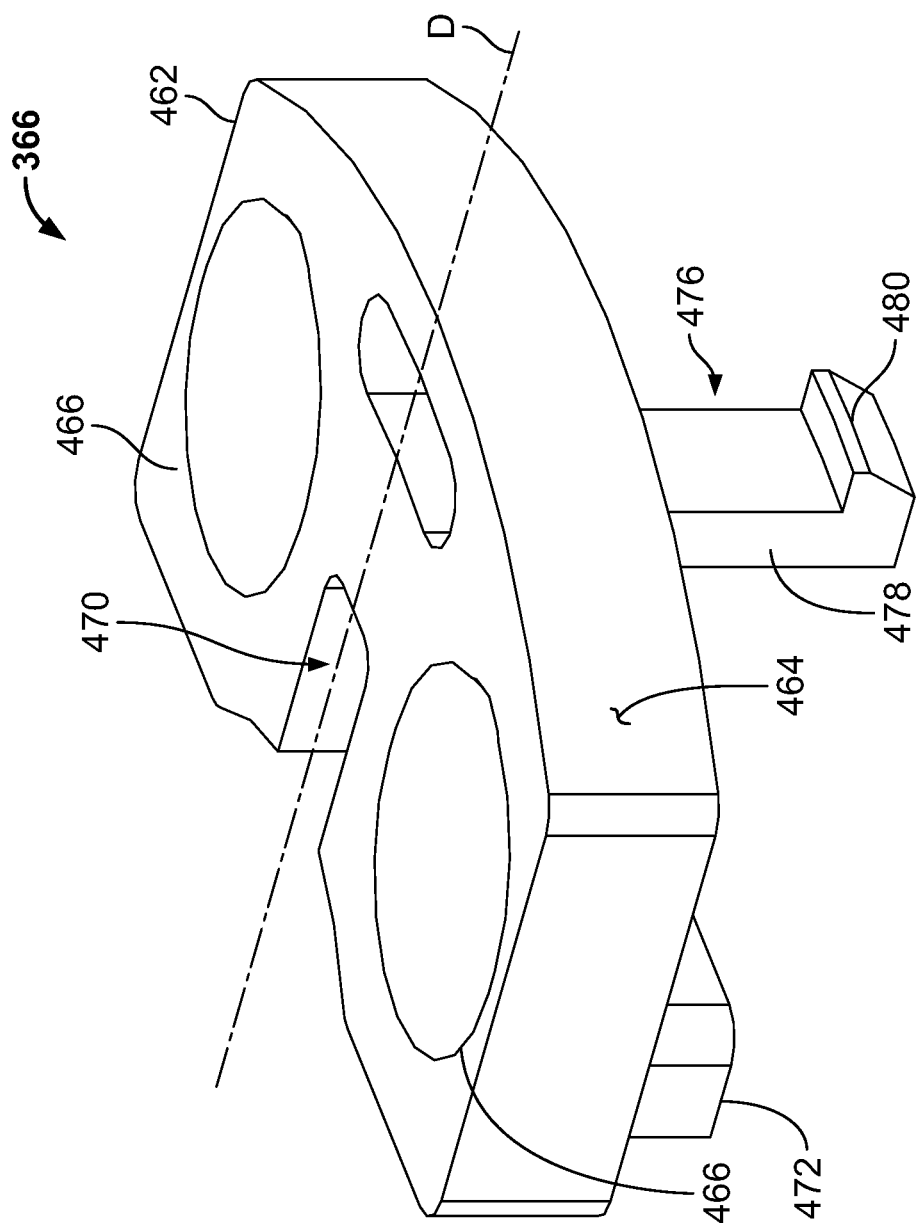
FIG. 29 is a front perspective view of a retention plate of the mechanical controller assembly.
Figure 30:
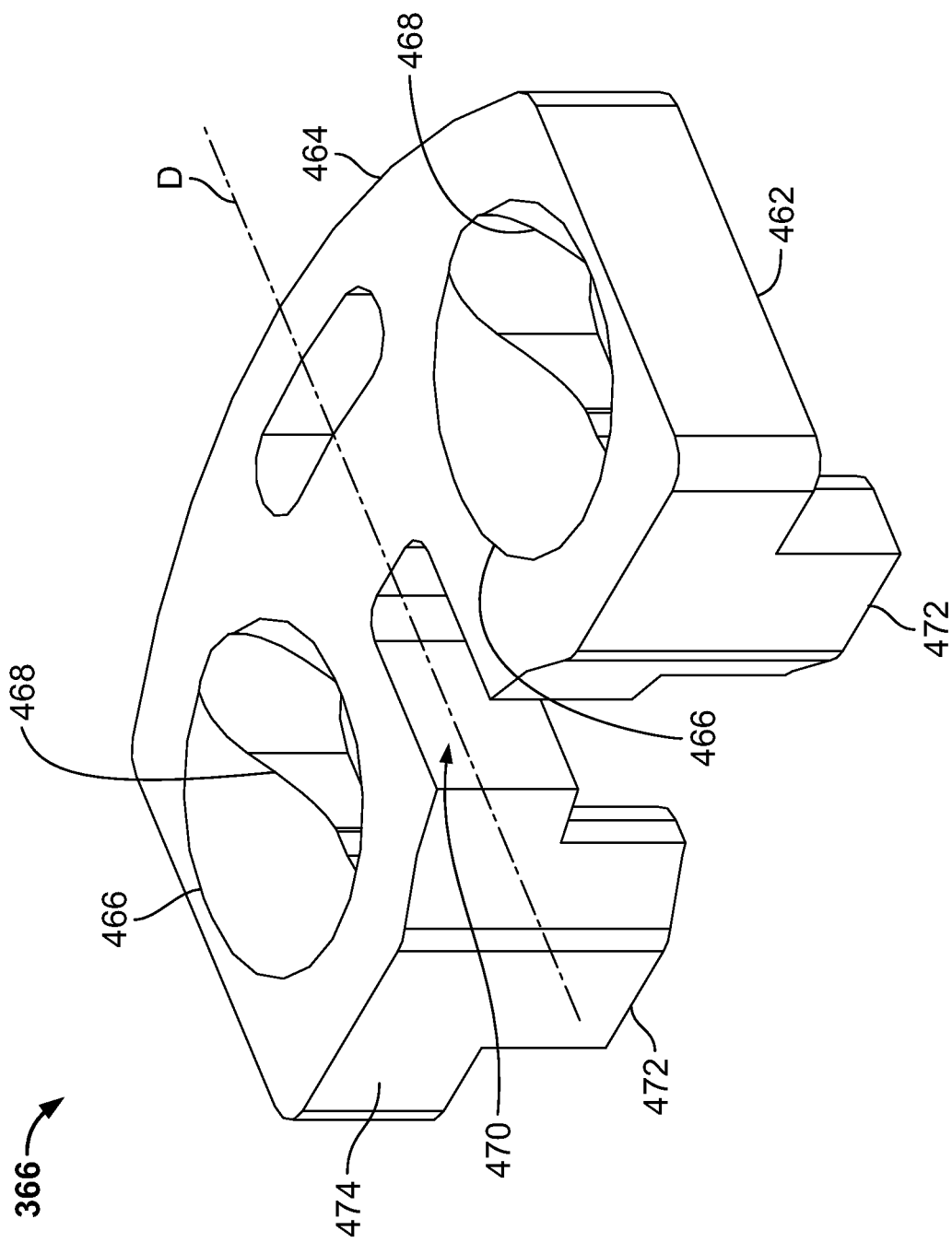
FIG. 30 is a rear perspective view of the retention plate.

FIG. 29 is a front perspective view of a retention plate 366 of the mechanical controller assembly 20. FIG. 30 is a rear perspective view of the retention plate 366. In the exemplary embodiment, the retention plate 366 is generally symmetrical about a centerline "D," and includes a generally rectangular-shaped body portion 462. A front or outer edge 464 of the body portion 462 has a radius that is substantially similar to a periphery of the body component 360. A pair of countersink holes 466 are formed through the body portion 462 and are configured to receive the mechanical hardware 410, as is described herein. Each countersink hole 466 includes an elongated slot 468 formed therethrough and generally parallel to the centerline "D." The slots 468 enable the retention plate 366 to slide radially with respect to the central axis "A" of the body component 360 when coupled thereto. The body portion 462 also includes an elongated open-ended slot 470 extending therethrough and generally centered on the centerline "D." The open-ended slot 470 is configured to receive at least a portion of a respective gusset portion 418 of the body component 360 when coupled thereto.

Extending downwardly from the bottom of the body portion 462 is a pair of bosses 472; one positioned on each side of the open-ended slot 470 and adjacent a rear edge 474 of the retention plate 366. The bosses 472 are configured to facilitate coupling the pivoting latches 368 to the body component 360. In particular, the bosses 472 are sized and shaped to extend into the cavity 398 in generally face-to-face contact with the bottom wall 404, and to extend across a width of the notches 402 formed in the cavity 398 of the body component 360, i.e., a respective boss 472 extends across a top opening of a respective notch 402. As described further herein, the cylindrical pins 452 of the pivoting latches 368 are positioned into the notches 402 when the fluid delivery apparatus 10 is assembled, and as described, are retained within the notches 402 by the bosses 472 of the retention plates 366.

Each retention plate 366 also includes a latch component 476 that extends downwardly from the bottom of the body portion 462 adjacent the outer edge 464. The latch component 476 is positioned such that it is generally centered about the centerline "D." The latch component 476 has an elongate body portion 478 formed integrally with the body portion 462 of the retention plate 366. The free end of the latch component 476 includes an outward extending protrusion 480 configured to provide a releasable latching connection with the latch receiving openings 310 of the cartridge housing 284 of the cartridge assembly 18.

Figure 31:
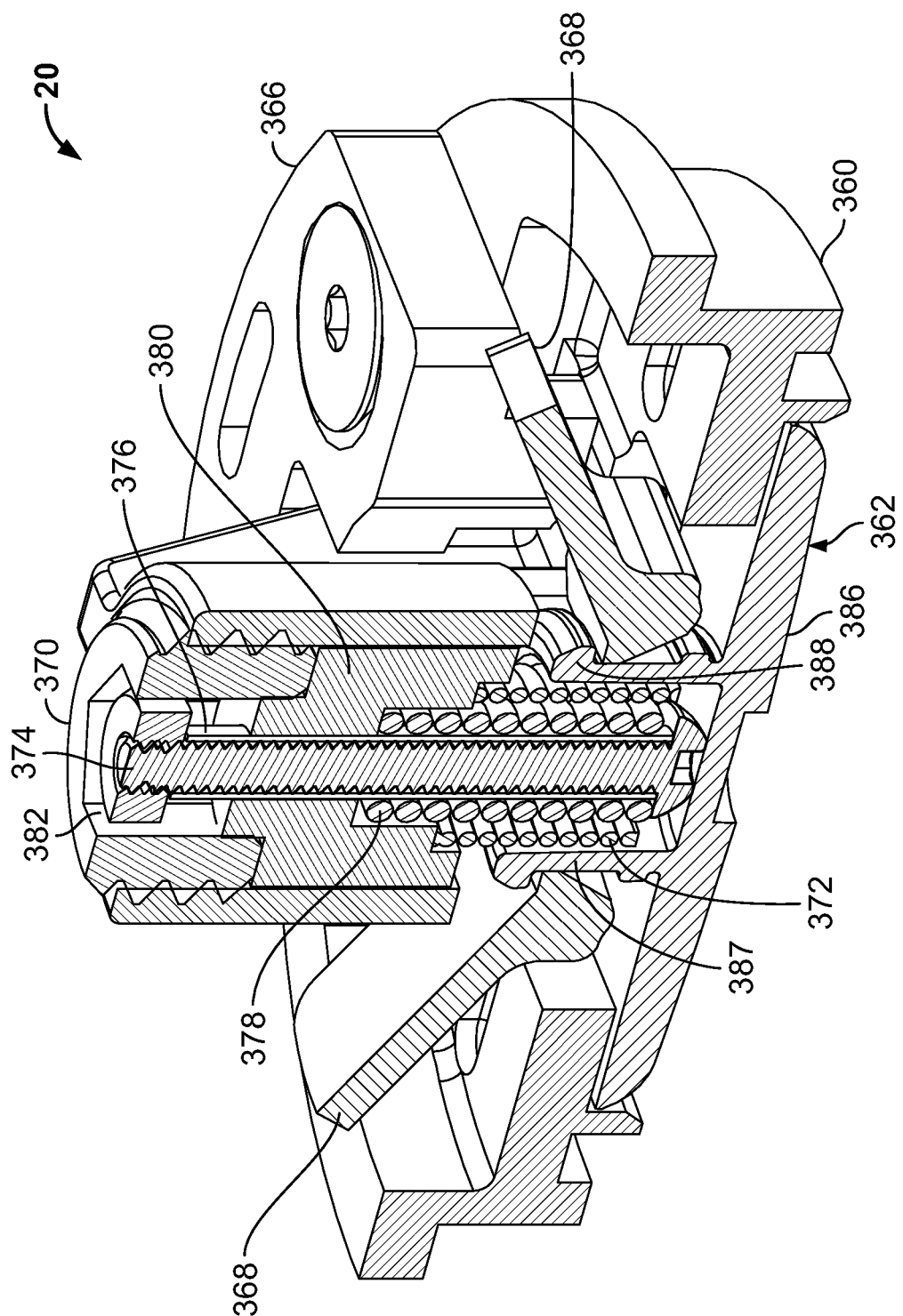
FIG. 31 is a perspective section view of the assembled mechanical controller assembly.
Figure 32:
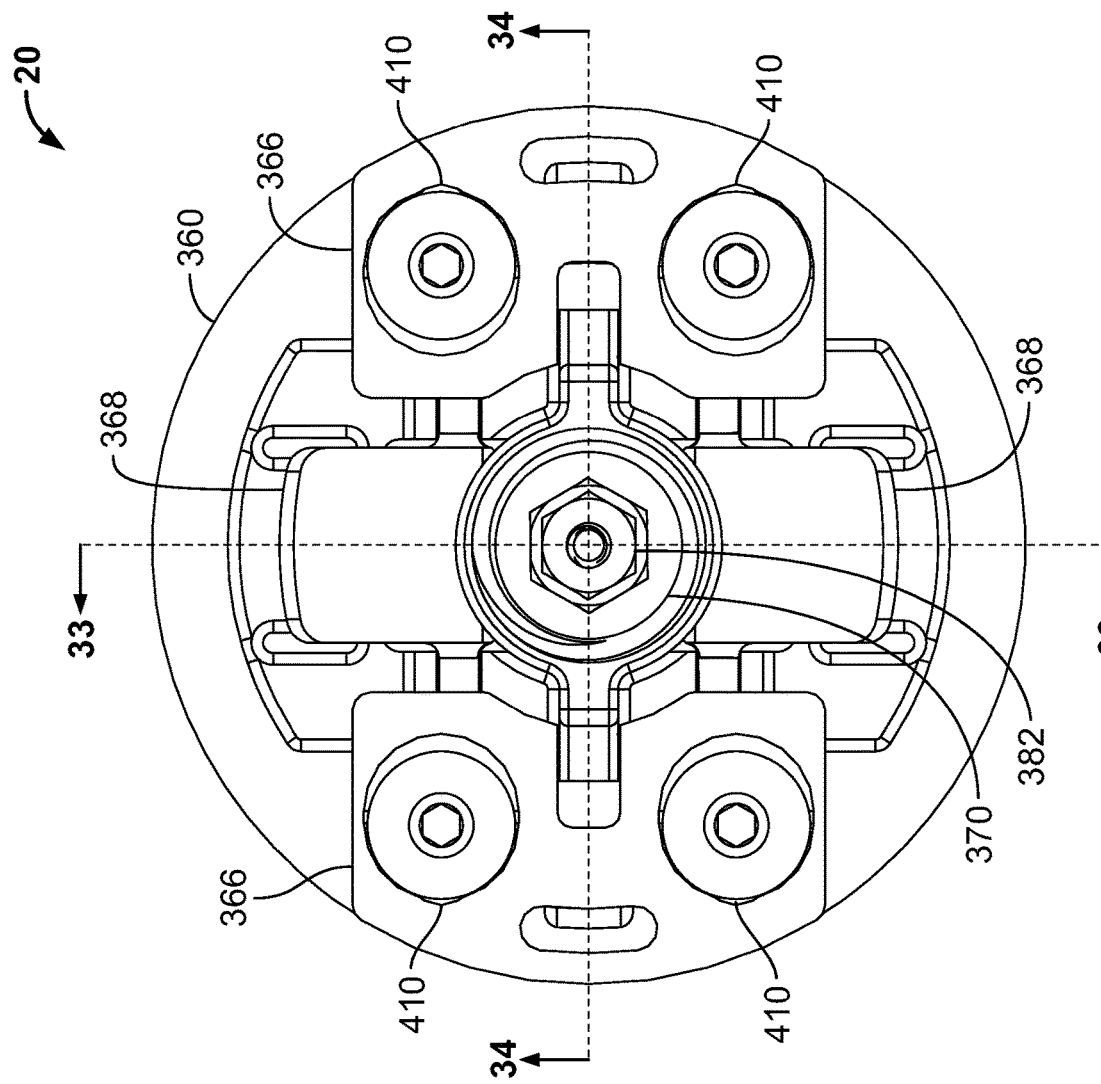
FIG. 32 is a top view of the mechanical controller assembly.
Figure 33:
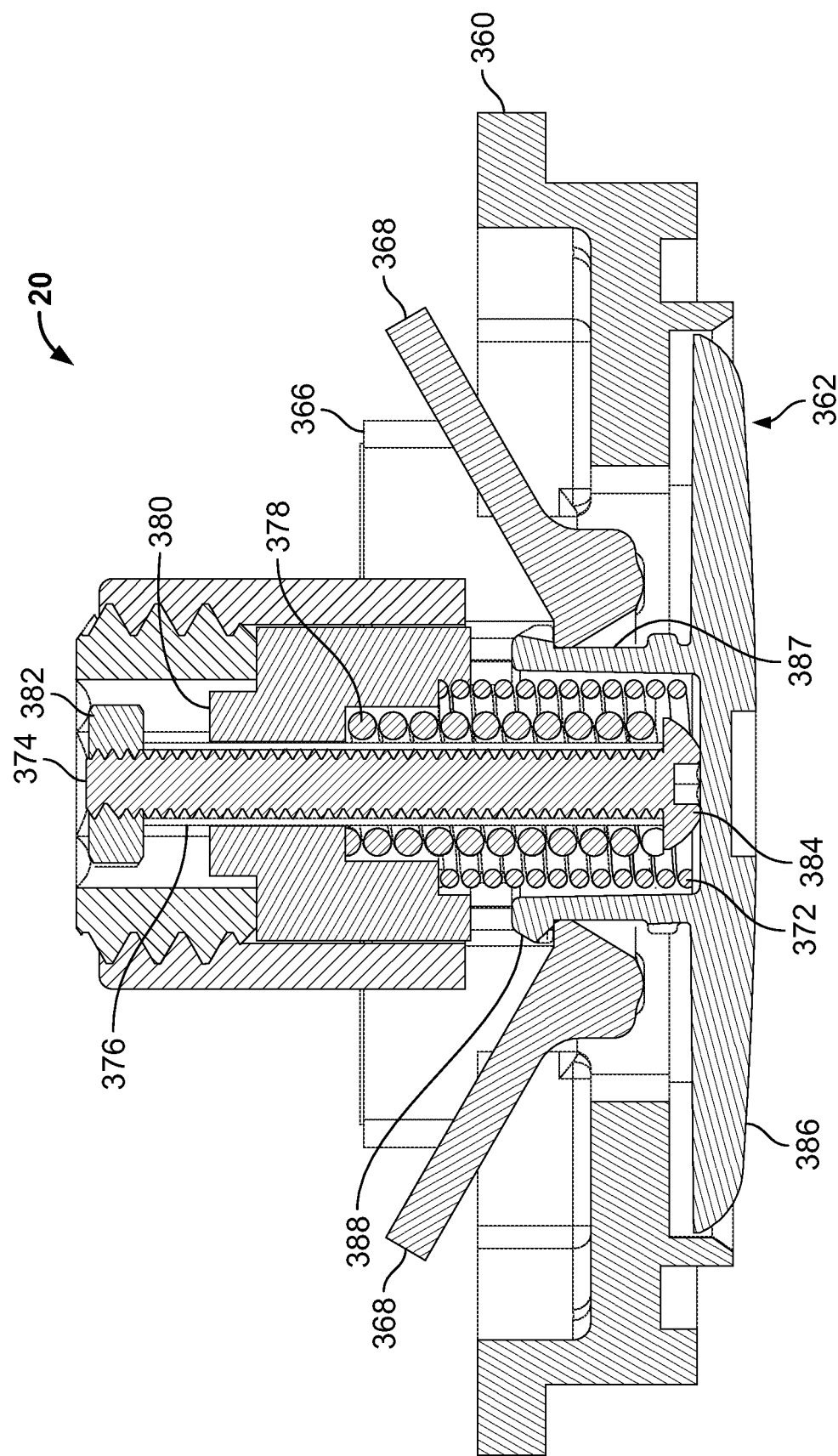
FIG. 33 is a sectional view of the mechanical controller assembly taken about line 33-33 of FIG. 32.
Figure 34:
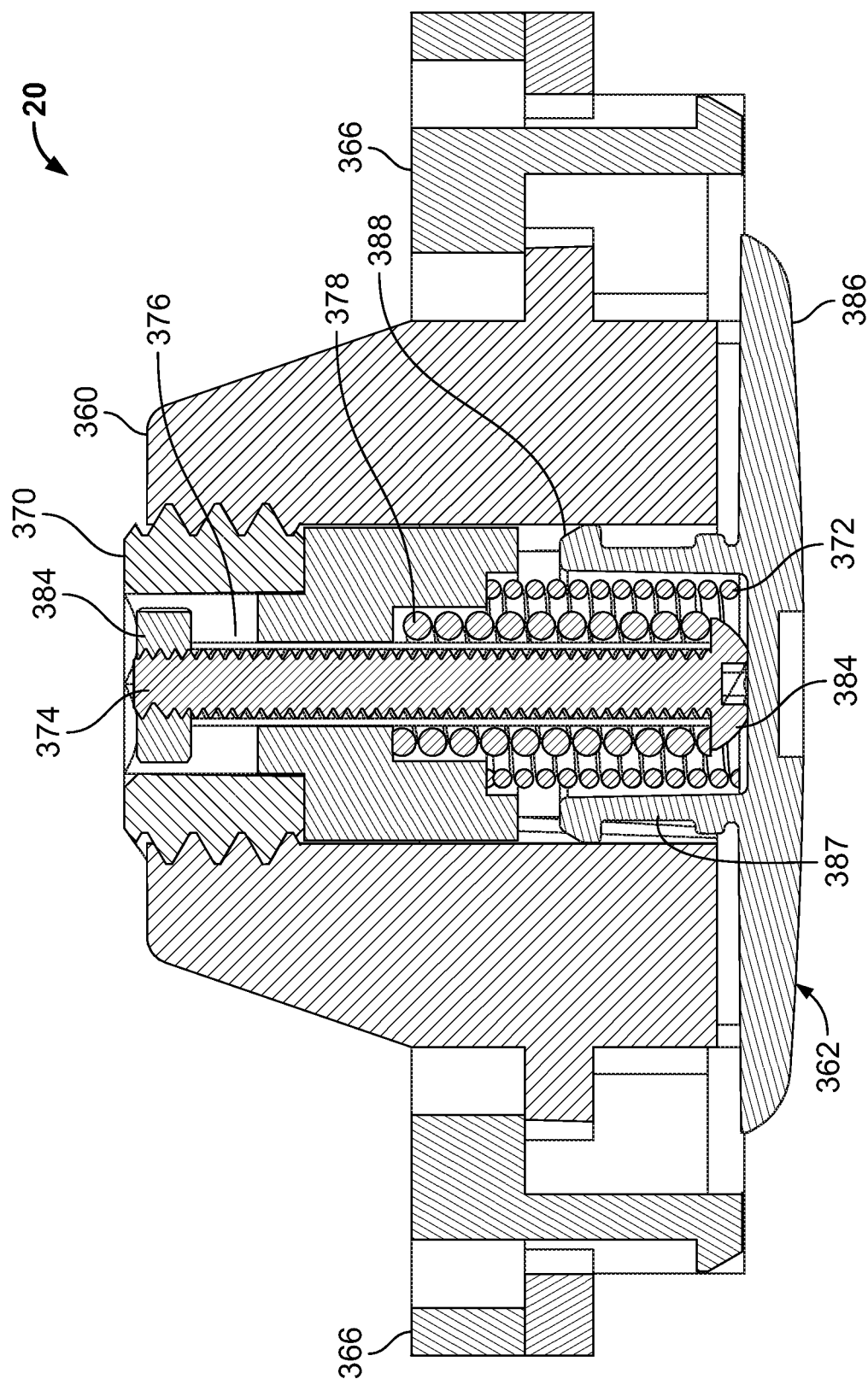
FIG. 34 is a sectional view of the mechanical controller assembly taken about line 34-34 of FIG. 32.

FIG. 31 is a perspective section view of the assembled mechanical controller assembly 20, FIG. 32 is a top view of the mechanical controller assembly 20, FIG. 33 is a sectional view of the mechanical controller assembly 20 taken about line 33-33 of FIG. 32, and FIG. 34 is a sectional view of the mechanical controller assembly 20 taken about line 34-34 of FIG. 32. With reference to the FIGS. 23 and 31-34, the biasing assembly 364 includes a first biasing member 372 and a second biasing member 378. In one embodiment, first biasing member 372 and a second biasing member 378 are springs. Alternatively, first biasing member 372 and a second biasing member 378 include any biasing component that enables biasing assembly 364 to function as described herein, including, for example, elastic, resilient materials; expandable foams; fluid (i.e., gas or liquid) compression members, and the like. In the exemplary embodiment, the first biasing member 372 and the second biasing member 378 each have a different length and a different force constant (or force profile). The biasing assembly 364 also includes a threaded fastener 374, a tube 376, an insert component 380, and a nut 382 configured to couple to the threaded fastener 374.

Figure 35:
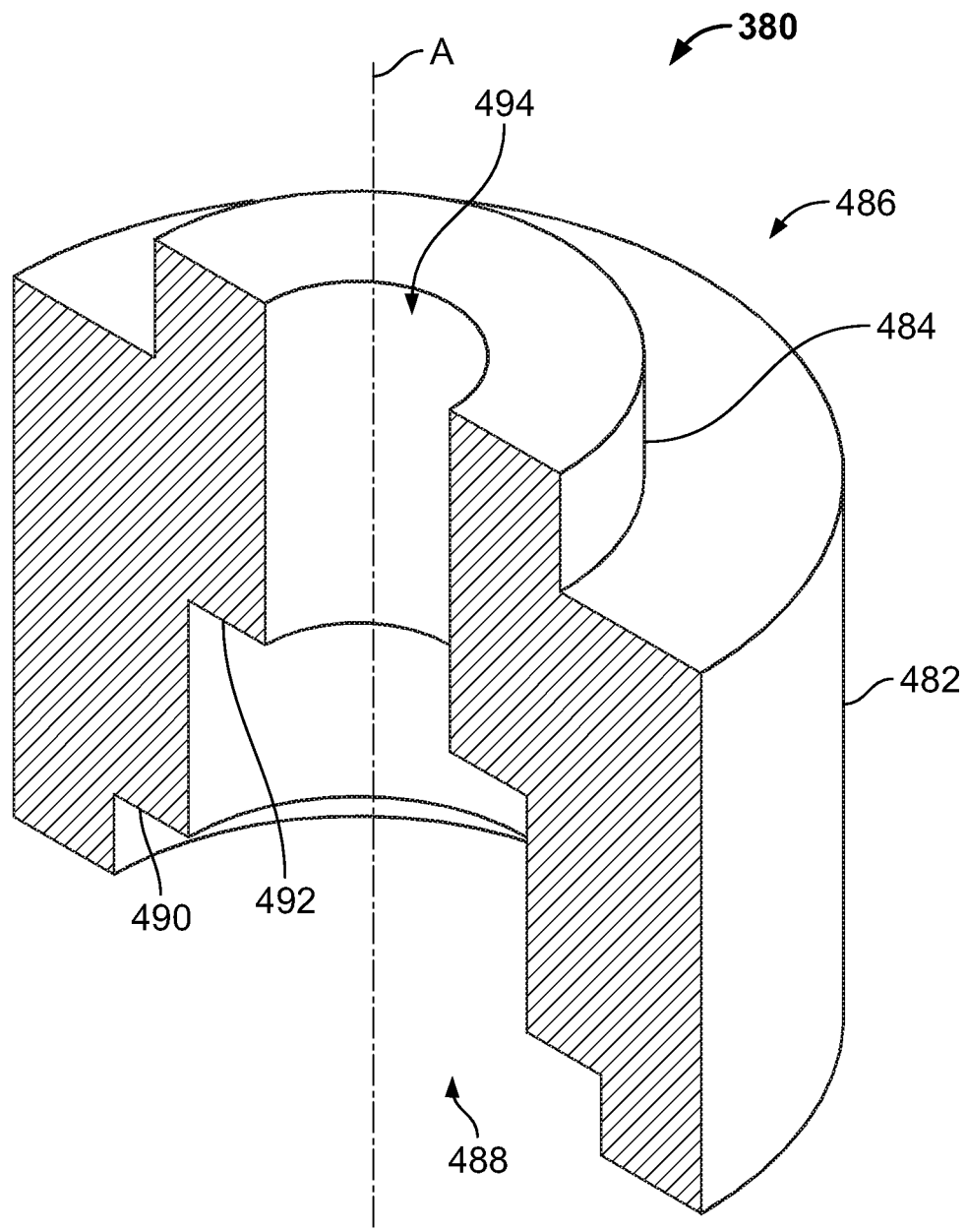
FIG. 35 is a perspective section view of an insert component of the mechanical controller assembly.

The insert component 380, as best illustrated in FIGS. 23 and 35, is generally cylindrically shaped and is symmetrical about the central axis "A." The insert component 380 includes a body 482 that has a cylindrical protrusion 484 extending from a first end 486 of the body 482. A second end 488 of the body 482 includes a first bore 490 that is sized to receive an end of the first biasing member 372 therein. The body 482 also includes a second bore 492 that is smaller than the first bore 490 and is sized to receive an end of the second biasing member 378 therein. An aperture 494 extends through the insert component 380 and is sized to receive the tube 376 therethrough.

As illustrated in the FIGS. 23 and 31-34, the threaded fastener 374 is inserted through the tube 376. The second biasing member 378 is positioned about the tube 376 such that an end of the second biasing member 378 rests on a head 384 of the threaded fastener 374. As such, the second biasing member 378 has as inner diameter that is larger than the periphery of the tube 376 and smaller than the periphery of the head 384 of the threaded fastener 374. The threaded fastener 374 and the tube 376 are inserted through the aperture 494 of the insert component 380 from the second end 488 such that the second biasing member 378 is seated in the second bore 492 of the insert component 380. The nut 382 is coupled to the threaded fastener 374 to facilitate retaining the insert component 380 on the threaded fastener 374 and the tube 376.

In the exemplary embodiment, the threaded adjustment member 370 is coupled to the threaded portion 424 of the cylindrical-shaped inner portion 392 of body component 360 to facilitate positioning the insert component 380 axially within the cylindrical-shaped inner portion 392. As described herein, this enables an amount of force applied by the biasing assembly 364 to the plunger component 362 to be adjusted. In the exemplary embodiment, the insert component 380, with the threaded fastener 374, the tube 376, the second biasing member 378, and the nut 382 coupled thereto, is inserted into the cylindrical-shaped inner portion 392 such that it is in contact with the threaded adjustment member 370.

The pivoting latches 368 are positioned in the body component 360 such that the cylindrical pins 452 are located in the notches 402 and the latch portions 456 extend radially inward. The retention plates 366 are positioned on the body component 360 with each respective latch component 476 extending downwardly through a respective opening 406. The bosses 472 of each respective retention plate extend over the notches 402, thereby retaining the cylindrical pins 452 of the pivoting latches 368 therein. This enables the pivoting latches 368 to rotate about the cylindrical pins 452, but to remain coupled to the body component 360. The retention plates are coupled to the body component 360 via the mechanical hardware 410 threadably coupled to the threaded holes 408 of the body component 360.

As illustrated in the FIGS. 31, 33, and 34, the first biasing member 372 positioned in the first bore 490 of the insert component 380. In the exemplary embodiment, the first biasing member 372 has an inner diameter that is larger than the periphery of the second biasing member 378 and the head 384 of the threaded fastener 374. The first biasing member 372 extends from the first bore 490 of the insert component 380 to the plunger component 362. The plunger component 362 includes a disk-shaped domed head 386 with an annular guide wall 387 coaxially extending vertically-upward from the domed head 386. As illustrated, the guide wall 387 is configured to receive the first biasing member 372 and the second biasing member 378 therein. The guide wall 387 includes an outwardly extending flange 388 adjacent the free end of the guide wall 387. The flange 388 is configured to engage the pivoting latches 368, and in particular, the latch portions 456, to facilitate retaining the plunger component 362 in a pre-use configuration, as shown in the FIGS. 33 and 34. In the exemplary embodiment, the domed head 386 is configured to engage the upper sealing member 280 of the cartridge assembly 18 via force applied by the biasing assembly 364 during use of the fluid delivery apparatus 10.

In the exemplary embodiment, with reference to the figures, in one suitable embodiment, the fluid distribution assembly 14 of the fluid delivery apparatus 10 is assembled by coupling the cap assembly 320 to the cartridge assembly 18. In particular, the upper seal wall 332 of the septum component 322 is inserted into the lower cavity 274 of the reservoir component 270 and the latching component 342 of the snap cap component 324 is snapped into the groove 344 of the reservoir component 270. As such, the snap cap assembly 320, and in particular, the septum component 322 seals the fluid passage 276 of the upper cavity 272 of the cartridge assembly 18. A fluid may be disposed into the upper cavity 272 for delivery to a user during use of the fluid delivery apparatus 10. The upper cavity 272 is closed by the upper sealing member 280, which is secured by the cartridge housing 284.

The mechanical controller assembly 20 is assembled in the pre-use configuration, as shown in the FIGS. 33 and 34, and is coupled to the upper portion of the cartridge assembly 18 via the retention plates 366. In particular, the annular sidewall 396 of the body component 360 is positioned on the upper edge portion 312 of the cartridge housing 284 such that the cutouts 412 in the annular sidewall 396 are aligned with the latch receiving openings 310 of the cartridge housing 284. The mechanical hardware 410 is loosened to enable the retention plates 366 to be displaced radially about the centerline "E," and enable the latch components 476 to engage the latch receiving openings 310. The mechanical hardware 410 is then tightened to secure the mechanical controller assembly 20 to the cartridge assembly 18.

In the exemplary embodiment, the cartridge assembly 18, along with the attached cap assembly 320 and the mechanical controller assembly 20, is coupled to the plenum assembly 16. As described herein, the plenum assembly 16 includes the plenum cap assembly 106 and the microneedle array assembly 108 coupled thereto. The cartridge assembly 18 is inserted into the cavity 110 of the plenum assembly 16. The flexible tabs 116 flex radially outwardly to receive the cartridge assembly 18 therebetween. The annular lower groove 306 of the cartridge housing 284 is aligned with the radially inward extending protrusions 122 of the flexible tabs 116, which enables the flexible tabs 116 to flex radially inward to secure the cartridge assembly 18 in the pre-use configuration.

In the exemplary embodiment, the fluid distribution assembly 14 of the fluid delivery apparatus 10 is coupled to the collet assembly 12 with by inserting the fluid distribution assembly 14 axially into the hollow interior space 24 of the collet assembly 12 from below. In particular, the recesses 130 of the sleeve component 100 of the plenum assembly 16 are axially aligned to the tabs 74 of the collet lock 50. The fluid distribution assembly 14 is displaced axially upwardly until top surface 142 of the lower wall portion 112 of the sleeve component 100 contacts the flexible tabs 48 of the collet assembly 12. The fluid distribution assembly 14 is rotated about the central axis "A" to axially align the flexible tabs 48 to the recesses 130. This facilitates displacing the tabs 74 of the collet lock 50 circumferentially into the recesses 132 of the sleeve component 100. The fluid distribution assembly 14 is again displaced axially upwardly, the displacement being stopped in response to the top surface 142 of the lower wall portion 112 of the sleeve component 100 contacting the inner horizontal surface 42 of the step 38 of the collet 22. As such, the fluid distribution assembly 14 is axially positioned above the tabs 74 of the collet lock 50. The fluid distribution assembly 14 is then rotated about the central axis "A" to axially align the recesses 128 of the sleeve component 100 with the tabs 74. As the fluid distribution assembly 14 is rotated, the flexible tabs 48 slide along the planar portion of the recesses 130 that overhangs the recesses 132. This causes the flexible tabs 48 to flex radially outwardly. As the fluid distribution assembly 14 is rotated, the flexible tabs 48 rotationally engage the outer surface 150 of the stops 146 and flex radially inwardly against the outer surface 150 to provide a snap-fit connection between the fluid distribution assembly 14 and the collet assembly 12. This facilitates preventing additional rotation of fluid distribution assembly 14 with respect to the collet assembly 12 and positions the recesses 128 into axial alignment with the tabs 74. The fluid delivery apparatus 10 is thereby assembled in the pre-use configuration shown in FIG. 1A.

Figure 36:
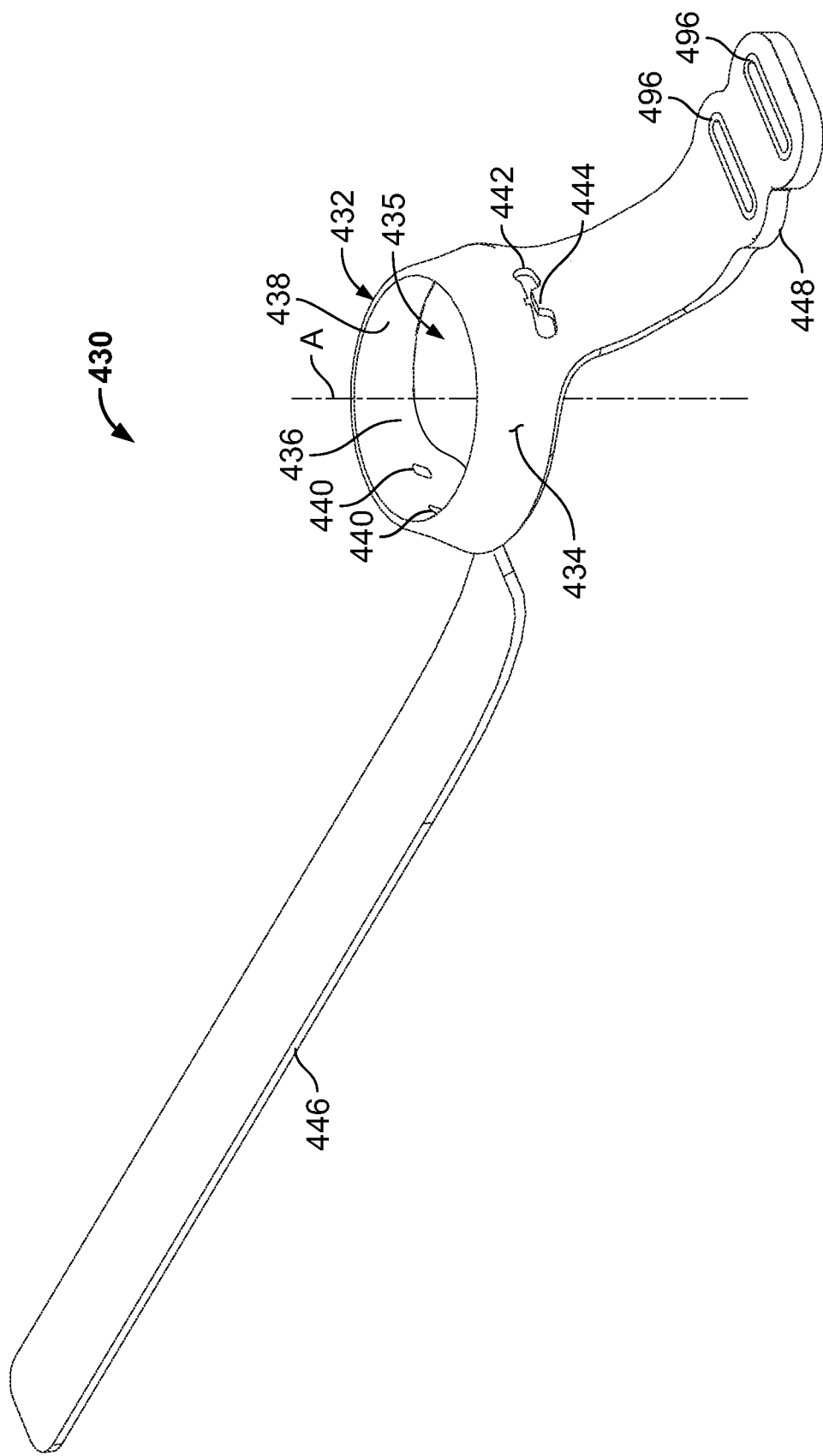
FIG. 36 is a perspective view of a band of the fluid delivery apparatus.
Figure 37:
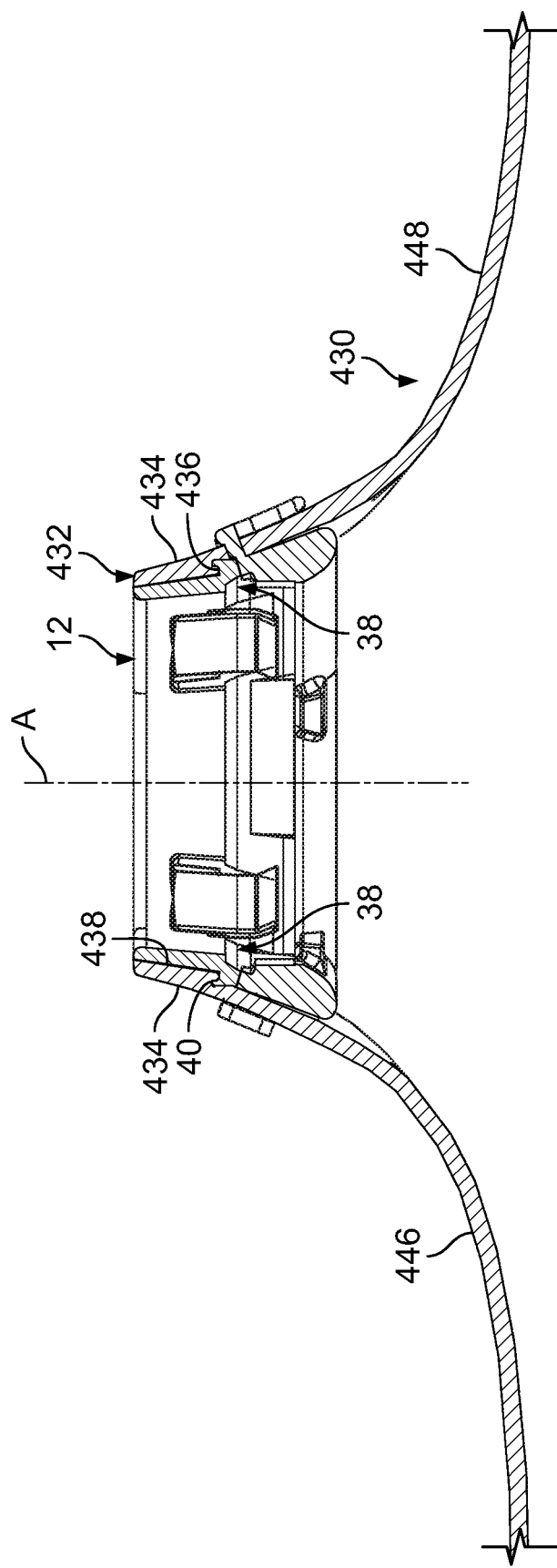
FIG. 37 is an enlarged sectional view of a portion of the band capturing the collet assembly shown in FIG. 4.

In one suitable embodiment, the fluid delivery apparatus 10 includes the attachment band 430, such as, for example, and without limitation, an arm band, a leg band, a waist band, wrist band, and the like. The attachment band 430 is configured to couple to the collet assembly 12 to facilitate attaching the fluid delivery apparatus 10 to a user during use. FIG. 36 is a perspective view of the attachment band 430 of the fluid delivery apparatus 10 of FIG. 1A, and FIG. 37 is an enlarged side sectional view of the attachment band 430 assembled to the collet assembly 12. In the exemplary embodiment, the attachment band 430 includes an annular body 432 having a wall 434 that is formed in a generally frustoconical shape, having a hollow inner space 435 defined therein. The annular body 432 is sized and shaped to correspond to the upper wall 30 and the lower wall 34 the collet 22. The inner space 435 is configured for receiving the fluid delivery apparatus 10. The attachment band 430 includes an inner step 436 that extends circumferentially around an inner surface 438 of the wall 434 of the annular body 432. In the exemplary embodiment, the inner step 436 corresponds to the step 38 and the horizontal surface 40 that extends around the upper wall 30 of the collet 22.

As illustrated in FIG. 36, the attachment band 430 includes an adjacent pair of attachment apertures 440 configured to couple to the second coupling members 68 of the collet lock 50, respectively. In particular, the apertures are sized and shaped to correspond to the neck portion 67, such that the head portion 69 retains the attachment band 430 on the collet assembly 12. In addition, the attachment band 430 includes an indicator aperture 442 opposite the attachment apertures 440. The indicator aperture 442 is generally kidney-shaped, whereas it is sized and shaped to correspond to the neck portion 63 of the first coupling member 66, such that the head portion 65 retains the attachment band 430 on the collet assembly 12. The indicator aperture 442 has an inner extension portion 444, or an indicator or an indicator portion, that extends inwardly from an edge of the indicator aperture 442. In particular, the indicator 444 is a tab that extends generally upward along wall 434 from a lower edge of indicator aperture 442. The indicator 444 is configured to extend into the window 61 of the head portion 65 and is configured to present an indication to the user of the fluid delivery apparatus 10 of a tightness of the attachment band 430.

The attachment band 430 includes a first strap 446 that extends generally radially outward from the annular body 432. In the exemplary embodiment, the first strap 446 is substantially aligned radially with the attachment apertures 440. The attachment band 430 also includes an opposite second strap 448 that extends generally radially outward from the annular body 432 and is substantially aligned radially with the indicator aperture 442. In the exemplary embodiment, the straps 446, 448 have a width that is less than a diameter of the annular body 432. Alternatively, the straps 446, 448 can have any width that enables the attachment band 430 to function as described herein. Additionally, in the exemplary embodiment, the annular body 432 and the straps 446, 448 are fabricated as an integral component. For example and without limitation, in one suitable embodiment, the annular body 432 and the straps 446, 448 may be fabricated from a resilient material, such as a thin elastomer. Alternatively, the annular body 432 and the straps 446, 448 may be fabricated separately and assembled using any fastening method that enables the attachment band 430 to function as described herein, for example, and without limitation, the straps 446, 448 can be coupled to the annular body 432 using spring pins or hinges.

As illustrated in FIG. 36, the second strap 448 includes at least one retaining aperture 496. In the exemplary embodiment, the retaining apertures 496 are fabricated from a rigid material, for example, and without limitation, a rigid plastic and/or metal. The retaining aperture 496 can be insert molded into second strap 448 or coupled thereto, for example, and without limitation, via adhesive bonding and/or mechanical coupling. In the exemplary embodiment, the first strap 446 and the second strap 448 are configured to couple to each other to secure the fluid delivery apparatus 10 to the users. For example, the second strap 448 includes two adjacent retaining apertures 496, and the first strap 446 may be wrapped around a portion of the user (e.g., a wrist, an arm, a leg, etc.) and then fed through one of the retaining apertures 496 and folded back and extended through the second retaining aperture 496. Alternatively, the attachment band 430 may include one retaining aperture 496, and the first strap 446 may have a length of hook and loop material (not shown) coupled arranged thereon. The first strap 446 may then be fed through the retaining aperture 496 and folded back upon itself so as to fasten with the loop fastening element to the hook fastening element. In other embodiments, the straps 446, 448 can have any coupling mechanism that enables the fluid delivery apparatus 10 to function as described herein.

Figure 38:
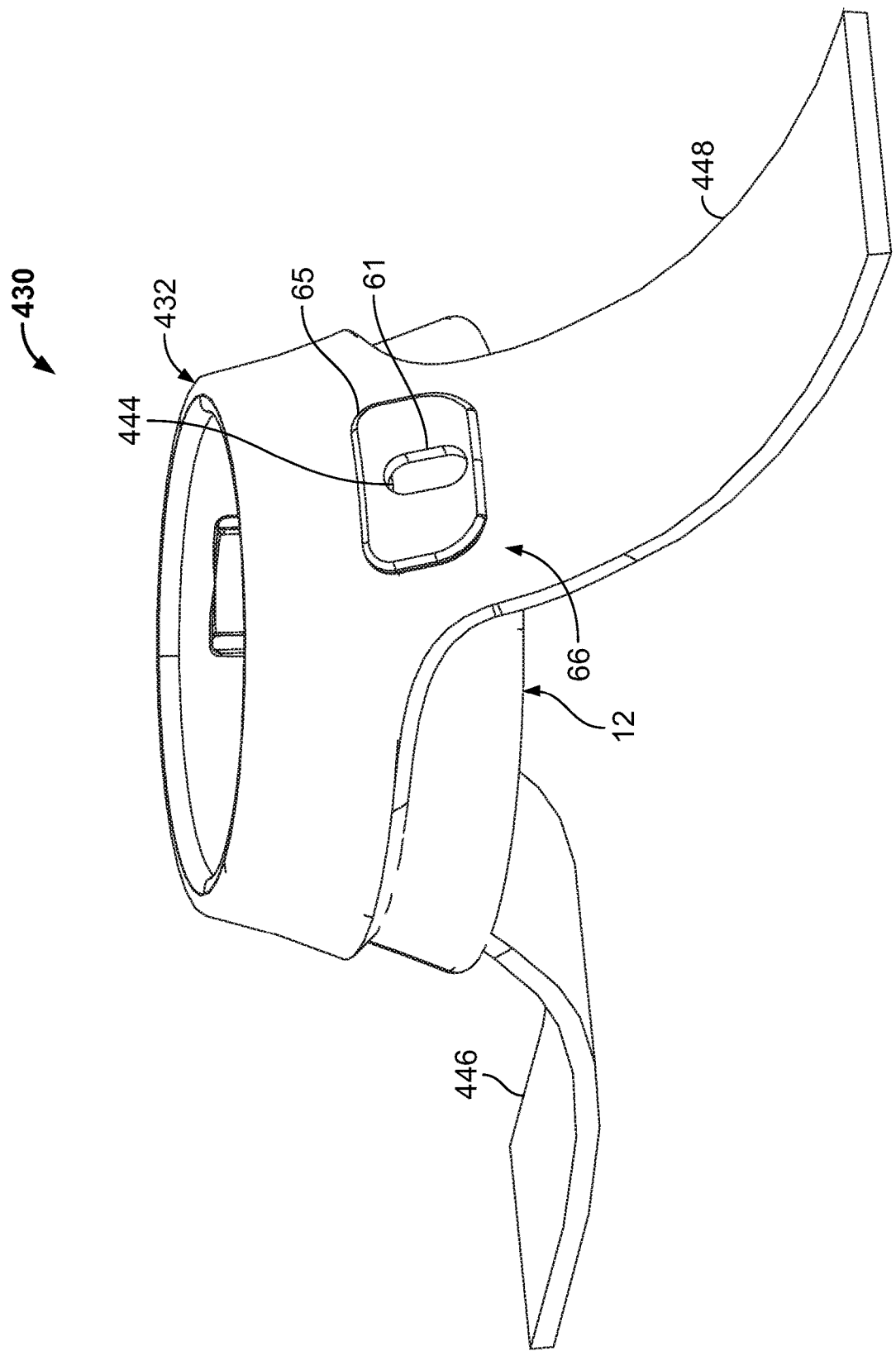
FIG. 38 is an enlarged perspective view of the band and collet assembly shown in FIG. 37, illustrating a first orientation of an indicator in a pre-use configuration.
Figure 39:
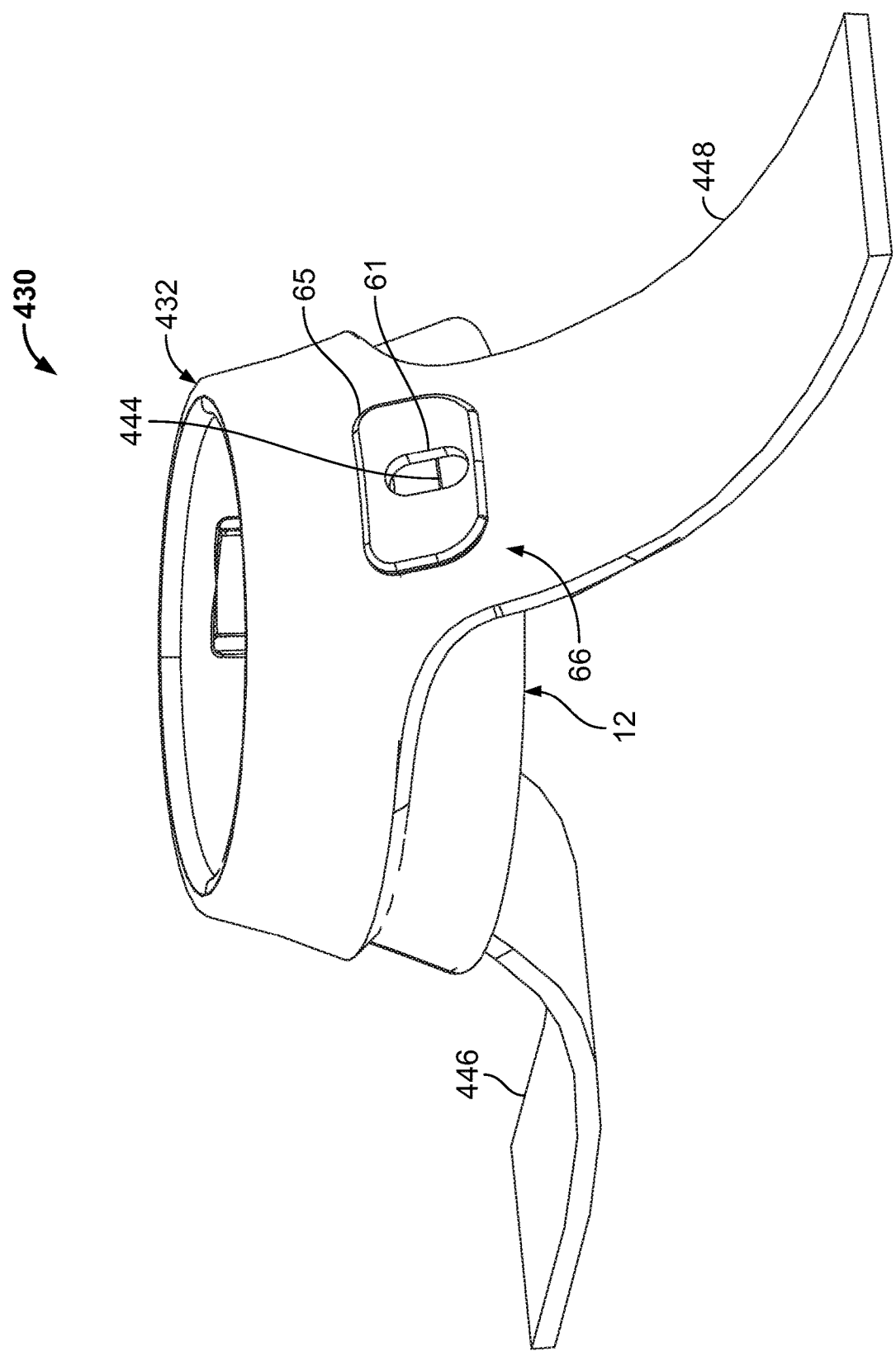
FIG. 39 is an enlarged perspective view similar to FIG. 8, but illustrating a second orientation of the indicator in a use configuration.

FIG. 38 is an enlarged perspective view of the attachment band 430 coupled to the collet assembly 12, illustrating a first orientation of the indicator 444 in a pre-use configuration. FIG. 39 is an enlarged perspective view of the attachment band 430 coupled to the collet assembly 12, illustrating a second orientation of the indicator 444 in a use configuration. The fluid distribution assembly 14 is not shown in FIGS. 38 and 39. In the exemplary embodiment, the straps 446, 448 are uncoupled or loose in the pre-use configuration of the fluid delivery apparatus 10. The indicator 444 is visible through the window 61 formed in the head portion 65 of the first coupling member 66, however, because the second strap 448 is free of tension, the edge of the indicator 444 is located at the top of the window 61. The indicator 444 thus provides a visual indication of the lack of tension in the attachment band 430 to the user via the window 61. During use, the straps 446, 448 are coupled together and tension is applied. Thus, as illustrated in FIG. 39, the edge of the indicator 444 moves downwardly in the window 61 due to the tension in the resilient material of the second strap 448. The indicator 444 thus provides a visual indication of an amount of tension in the attachment band 430 to the user via the window 61. It is contemplated that the head portion 65 of the first coupling member 66 may contain a visual reference to indicate to the user an appropriate amount of tension in the attachment band 430. For example, and without limitation, the head portion 65 can include a mark than aligns with the edge of the indicator 444 when the appropriate amount of tension is achieved in the attachment band 430.

As illustrated in FIGS. 37-39, the attachment band 430 is coupled to the collet assembly 12 via the apertures 440, 442. The fluid delivery apparatus 10 is positioned in the inner space 435. The attachment apertures 440 are expanded to receive a respective coupling member 68. The resilient material of the attachment band 430 enables each aperture 440 to expand such that the head portion 69 of the coupling member 68 can be displaced therethrough. After displacing the head portion 69 through the aperture 440, the aperture 440 returns to its original shape and size due to the resiliency of the material used to fabricate the attachment band 430. As such, the attachment apertures 440 encircle the neck portion 67 of the coupling members 68 such that the head portions 69 cannot be easily displaced back through the attachment apertures 440. Similarly, the indicator aperture 442 is expanded to receive the first coupling member 66. The indicator aperture 442 is expanded to enable the head portion 65 to be displaced through the indicator aperture 442. The indicator aperture 442 returns to its original size and shape to encircle the neck portion 63 such that the head portion 65 cannot be easily displaced back through the indicator aperture 442.

To further secure the fluid delivery apparatus 10 to the attachment band 430 and to enable the attachment band 430 to apply a generally axial force to the fluid delivery apparatus 10, the inner step 436 of the attachment band 430 to positioned against the step 38 of the collet assembly 12. In addition, the inner surface 438 of the attachment band 430 in positioned against the upper wall 30 of the collet assembly 12. The band is secured in place via the apertures 440, 442, and the coupling members 66, 68. When the attachment band 430 is tightened around the user's body, such as an arm or wrist of the user, the band provides a substantially axial force to the fluid delivery apparatus 10, generally along the central axis "A." The axial force against the user's body facilitates deforming the user's skin, for example, by pushing or crowning a portion of the user's skin encircled by the collet assembly 12. The indicator 444, which is visible through the window 61 of the first coupling member 66, presents a visual indication to the user that indicates a proper amount of force is applied to the fluid delivery apparatus 10. The skin deformation and the crowning of the portion of the user's skin encircled by the collet assembly 12 facilitate proper penetration of the microneedle array assembly 108 into the user's skin.

Figure 40:
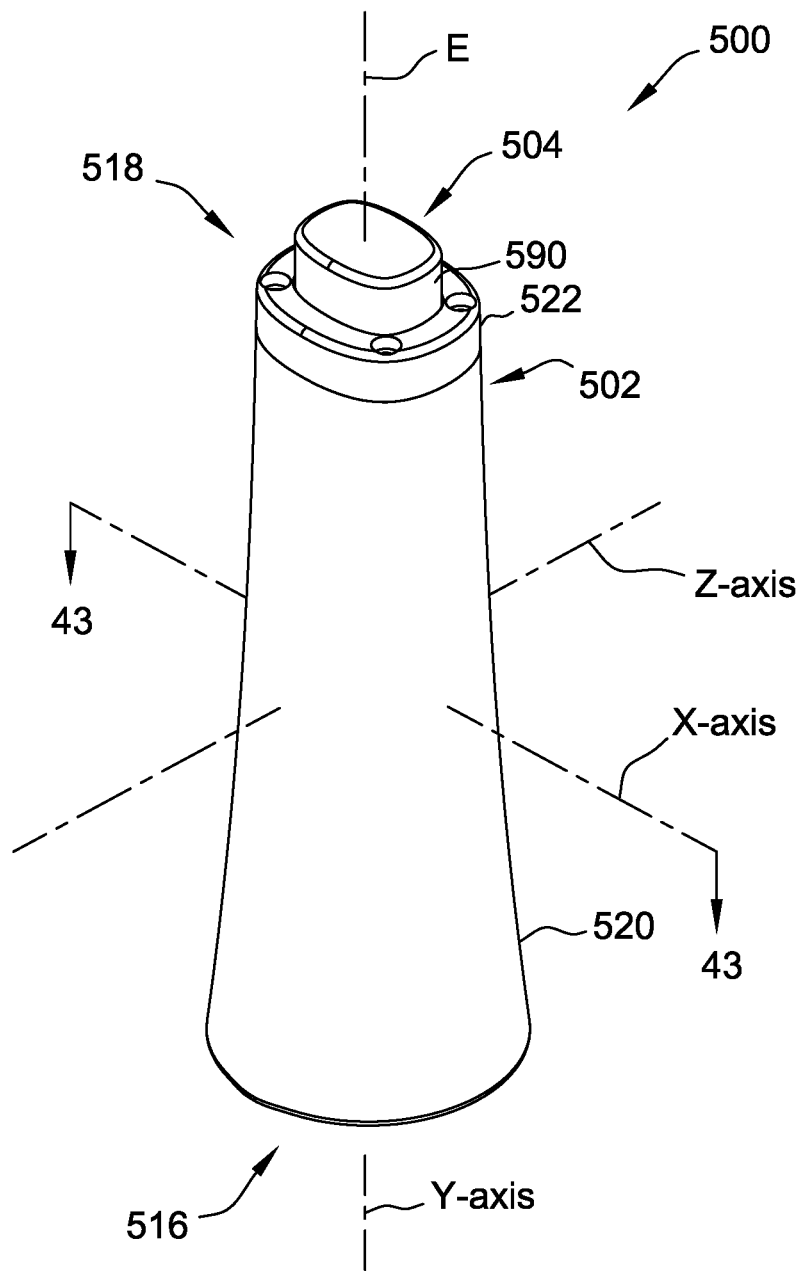
FIG. 40 is a perspective view of an applicator of the fluid delivery apparatus.
Figure 41:
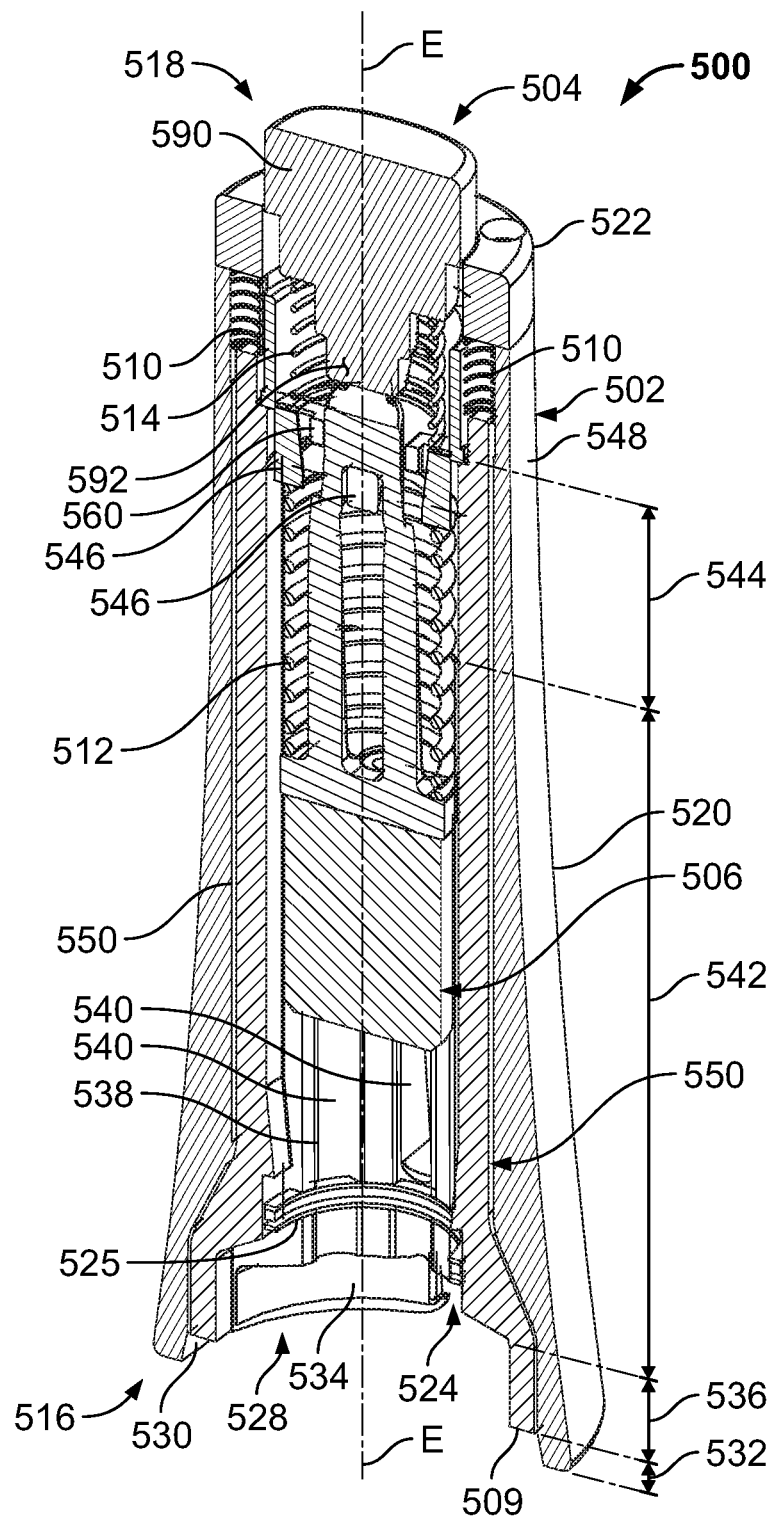
FIG. 41 is a front sectional view of the applicator shown in FIG. 40.
Figure 42:
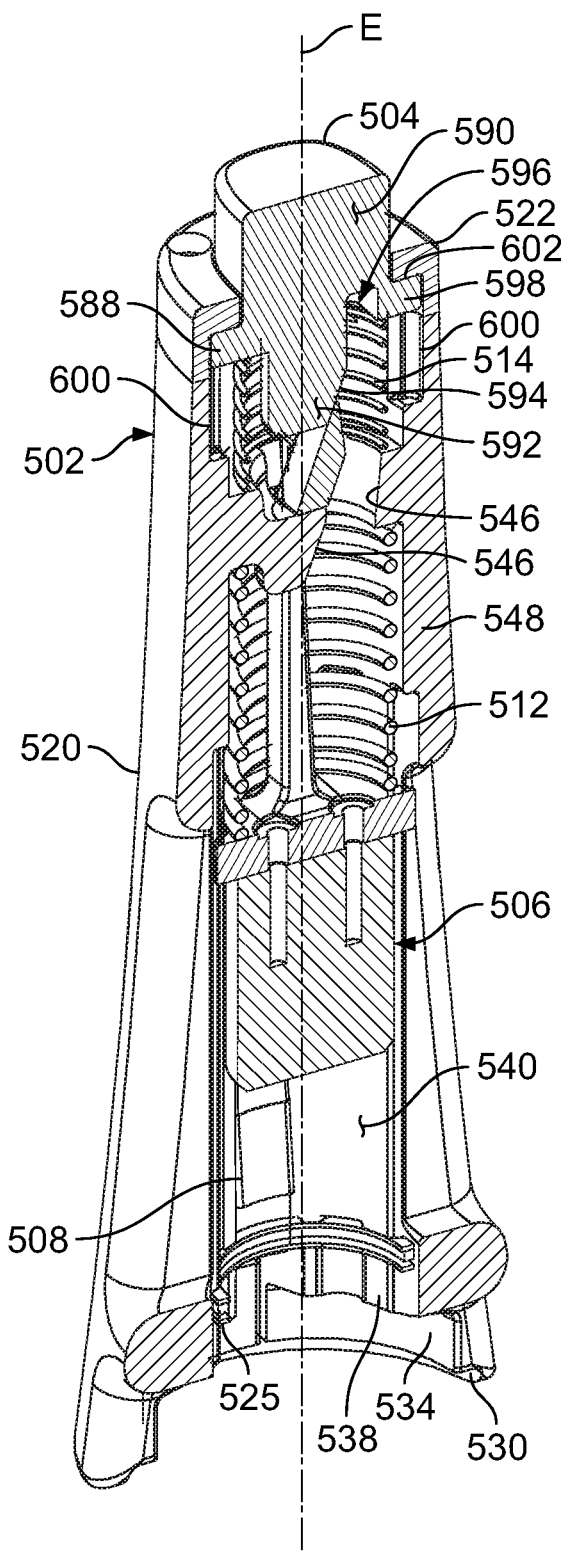
FIG. 42 is a side sectional view of the applicator shown in FIG. 40.
Figure 43:
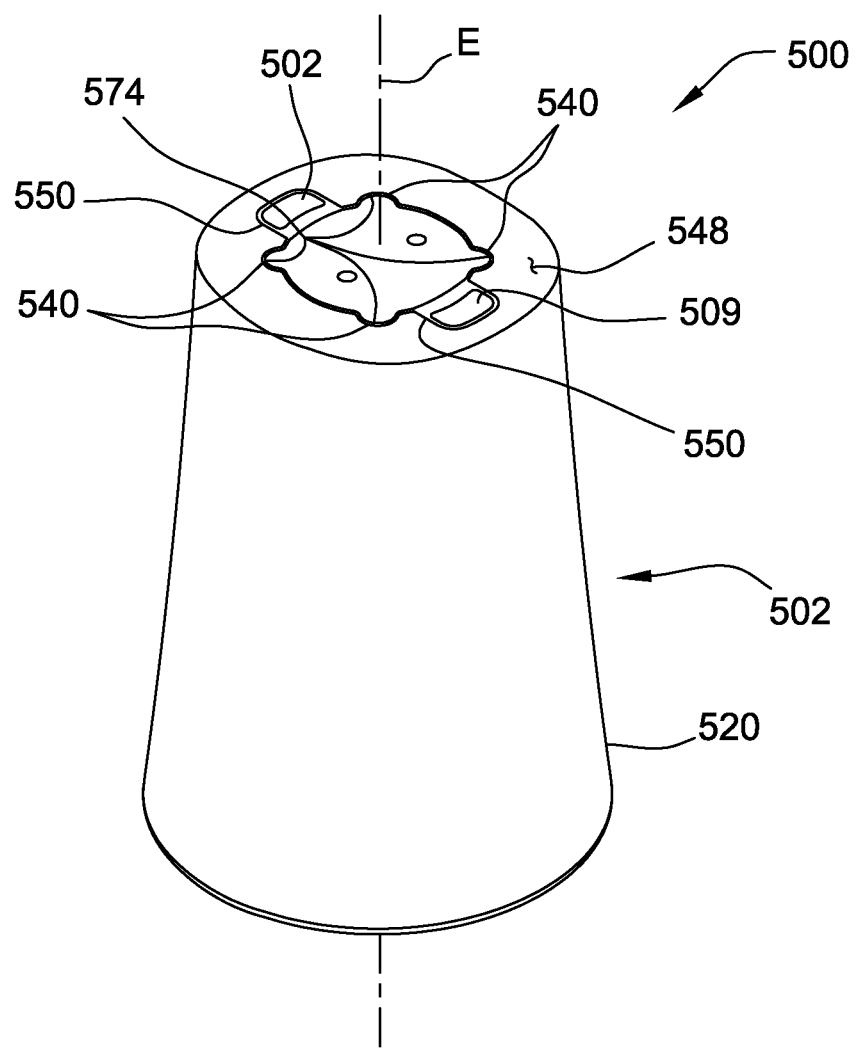
FIG. 43 is a top sectional view of the applicator taken about line 43-43 shown in FIG. 40.

An applicator 500 (or broadly an application device) is optionally provided to facilitate the transition of the fluid delivery apparatus 10 from the pre-use configuration shown in FIG. 1A to the pre-activated configuration shown in FIG. 1B. FIG. 40 is a perspective view of one suitable embodiment of the applicator 500 of the fluid delivery apparatus 10. FIG. 41 is a front sectional view of the applicator 500. FIG. 42 is a side sectional view of the applicator 500. FIG. 43 is a top sectional view of the applicator 500, taken about line 43-43 shown in FIG. 40. In the exemplary embodiment, the applicator 500 has a housing 502 with a button 504 (or release) for activating the applicator 500. The housing 502 encloses a piston 506 (or impact component) used to activate the fluid delivery apparatus 10. The piston is locked into a safety position by one or more safety arms 508, 509. In addition, the housing encloses safety arm springs 510, piston spring 512, and button spring 514.

In the exemplary embodiment, the elongate body 520 has a generally cylindrical shape tapering inwardly from a bottom 516 to a top 518 of the body 520. The housing 502 also includes a cap 522 coupled to the top 518 of the body 520. The cap 522 is configured to retain the button 504, which is configured to move axially with respect to the body 520. It is noted that the applicator 500 is formed substantially symmetrical about an X-Y plane and a Y-Z plane that includes the centerline "E," as shown in FIG. 40.

With reference to the FIGS. 41-43, the body 520 includes a stepped bore 528 that extends through the body 520. At the bottom end 516, the stepped bore 528 includes a first step portion 530 that has a periphery that is sized and shaped to receive the upper wall 30 of the collet 22 therein. As shown in FIG. 41, the first step portion 530 extends upwardly from the bottom 516 of the body 520 a predetermined distance 532. The stepped bore 528 also includes a second step portion 534 that extends upwardly from the first step portion 530 a predetermined distance 536. In the exemplary embodiment, the second step portion 534 has a periphery that is sized and shaped to receive the fluid distribution assembly 14 while the first step portion 530 is in contact with the upper wall 30 of the collet 22. In addition, the stepped bore 528 includes a third step portion 538 that extends upwardly from the second step portion 534 and continues through the body 520. Positioned inside the body 520, and in particular, the third step portion 538 is a retaining ring 525. The retaining ring 525 is configured facilitate retaining the piston 506 and the safety arms 508, 509 axially within the housing 502. In addition, the third step portion 538 includes a plurality of axially-extending grooves 540 that extend upwardly from the second step portion 534 a predetermined distance 542. The grooves 540 have a curved cross-sectional shape that is generally centered on a radially extending line from the centerline "E." That is, the grooves 540 extend axially through the second step portion 534 and are arranged radially about the centerline "E." Alternatively, the cross-sectional shape of the grooves 540 can be any shape that enables the applicator 500 to function as described herein. In the exemplary embodiment, the third step portion 538 has a periphery that is sized and shaped to receive the piston 506 therein.

In the exemplary embodiment, the third step portion 538 of the stepped bore 528 includes a piston retention member 546 that is positioned a predetermined distance 544 upwardly from the grooves 540. The piston retention member 546 is formed from a body that extends radially inwardly from an outer wall 548 of the body 520 and is configured to facilitate locking the piston 506 in place until the safety arms 508, 509 are actuated, thereby unlocking the piston 506. In addition, the piston retention member 546 functions as a spring seat for the piston spring 512 that is positioned between the piston 506 and the piston retention member 546, and the button spring 514 that is positioned between the button 504 and the piston retention member 546.

The body 520 also includes an opposing pair of longitudinal channels 550 that extend axially through the body 520. The channels 550 extend through the second and third step portions 534, 538, respectively, of the stepped bore 528. As best illustrated in FIG. 41, the channels 550 are formed in the wall 548 of the body 520 and taper outward at the bottom 516 from the third step portion 538 to the second step portion 534. As such, the safety arms 508, 509 can be inserted into the channels 550 such that they do not interfere with the fluid delivery apparatus 10 during activation and/or use of the applicator 500. Thus, the channels 550 are sized and shaped to receive a respective safety arm 508, 509 slidingly therein, i.e., the safety arms 508, 509 are free to slide axially within the body 520 during use of the applicator 500. As best illustrated in FIG. 43, the grooves 540 and the channels 550 are generally circumferentially spaced equidistant about the centerline "E."

Figure 44:
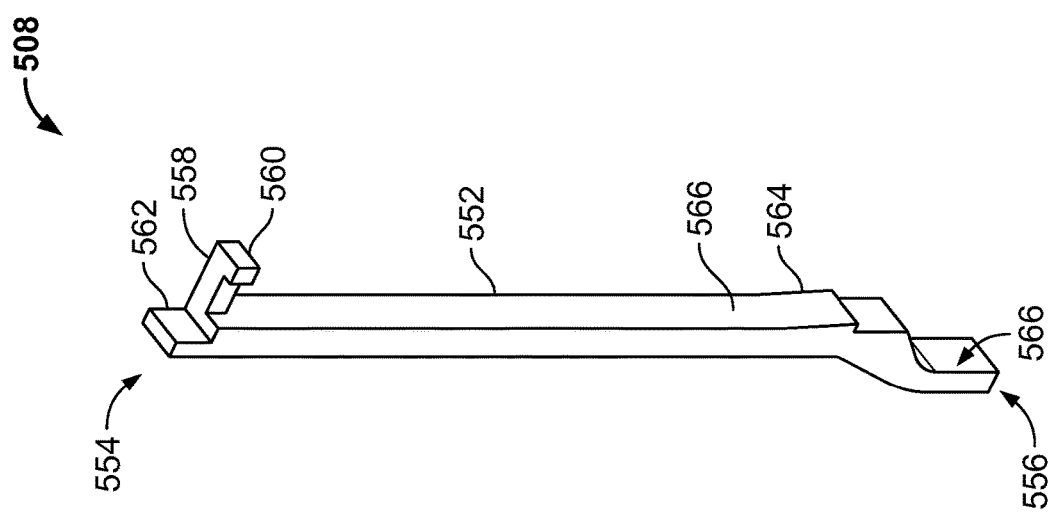
FIG. 44 is a perspective view of a safety arm of the applicator.

FIG. 44 is a perspective view of the safety arm 508. In the exemplary embodiment, the applicator includes two safety arms 508, 509. Alternatively, the applicator may include any number of safety arms that enable the applicator 500 to function as described herein. It is noted that in the exemplary embodiment, the safety arm 509 is formed substantially similar to safety arm 508, but as a symmetrical opposite. Thus, only the detailed description of safety arm 508 is provided herein. In the exemplary embodiment, the safety arm 508 includes an elongate body portion 552 that includes an upper end 554 and a lower end 556. The body portion 552 has a cross-sectional shape that is generally rectangular. Alternatively, the body portion can have any cross-sectional shape that enables the safety arm 508 to function as described herein. In the exemplary embodiment, at the upper end 554, the safety arm 508 includes a spring engagement member 562 that extend axially along the elongate body portion 552. The spring engagement member 562 is configured to engage the safety arm spring 510, which biases the safety arm 508 into the safety position within the applicator 500.

Furthermore, the safety arm 508 includes a piston locking arm 558 that extends generally perpendicular to the elongate body portion 552. The piston locking arm 558 includes a protrusion 560 extending therefrom. As illustrated in FIG. 41, the locking arm 558 extends radially inward past a portion of the piston retention member 546 to a positioned adjacent the piston 506. The protrusion 560 extends forward from the locking arm 558 and is configured to facilitate preventing the piston 506 from releasing from the piston retention member 546, as is described further herein.

At the lower end 556, the safety arm 508 includes a retention member 564 that extends outwardly from an inner surface 566 of the elongate body portion 552. As illustrated in FIG. 41, the retention member 564 extends radially inwardly with respect the applicator 500 and is configured to contact the retaining ring 525 when the safety arm 508 is biased axially in the safety position. Thus, the retention member 564 facilitates retaining the safety arm 508 within the applicator 500. The lower end 556 of the elongate body portion 552 tapers generally outwardly opposite the retention member 564, forming a notch 567. As illustrated in FIG. 41, the notch 567 is configured to correspond to the second step portion 534 of the stepped bore 528. As such, the safety arm 508 may be positioned in the channel 550 of the housing 502 and retained for axial movement therein.

Figure 45:
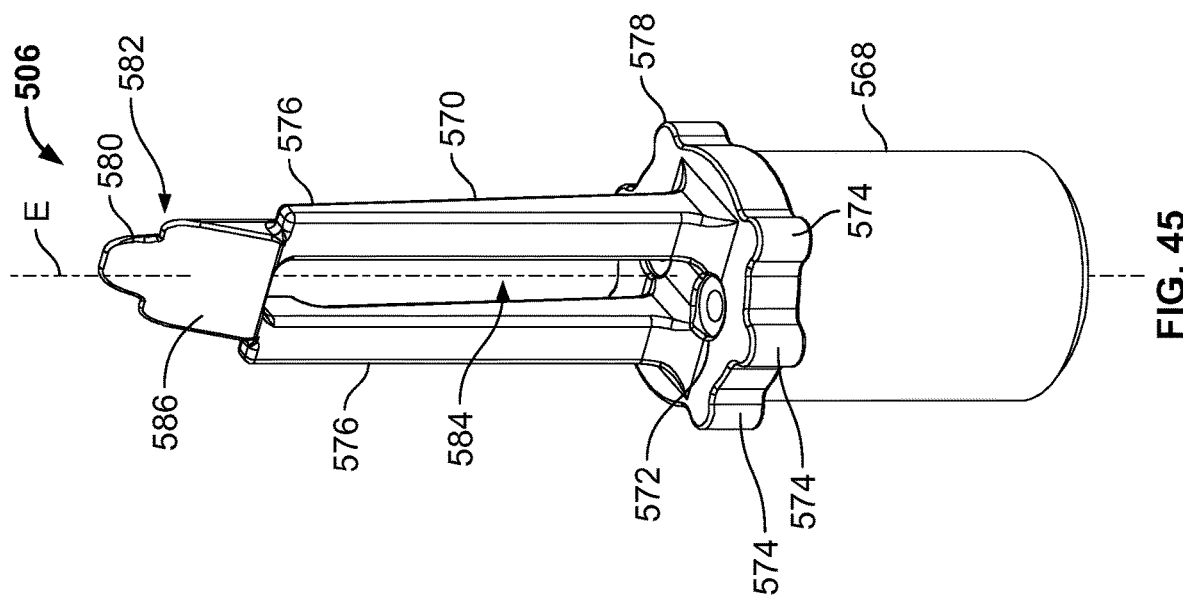
FIG. 45 is a front perspective view of a piston of the applicator.

FIG. 45 is a front perspective view of the piston 506 of the applicator 500 shown in FIG. 40. In the exemplary embodiment, the piston 506 includes a piston head 568 coupled to a piston hanger 570 via mechanical hardware (not shown). The piston head 568 is a generally cylindrical solid body that includes threaded holes (not shown) that correspond to mounting holes 578 formed in the piston hanger 570. The mounting holes 578 and the threaded holes in the piston head 568 facilitate releasably coupling the piston head 568 to the piston hanger 570. In the exemplary embodiment, the piston head 568 is fabricated as a generally solid component having a predetermined mass that enables the piston 506 to achieve a desirable velocity and impulse rate during use of the applicator 500 to properly activate the fluid delivery apparatus 10 for use.

The piston hanger 570 includes a generally annular bottom wall 572 that includes a plurality of axially extending protrusions 574. Each of the protrusions 574 generally correspond to a respective groove 540 formed in the body 520 of the housing 502. The protrusions 574 have a generally curved shape that is generally aligned with a radially extending line from the centerline "E." That is, the protrusions 574 extend axially along the bottom wall 572 and are arranged radially about the centerline "E." Alternatively, the shape of the protrusions 574 can be any shape that enables the piston hanger 570 to slidably engage the housing 502 as described herein.

Figure 47:
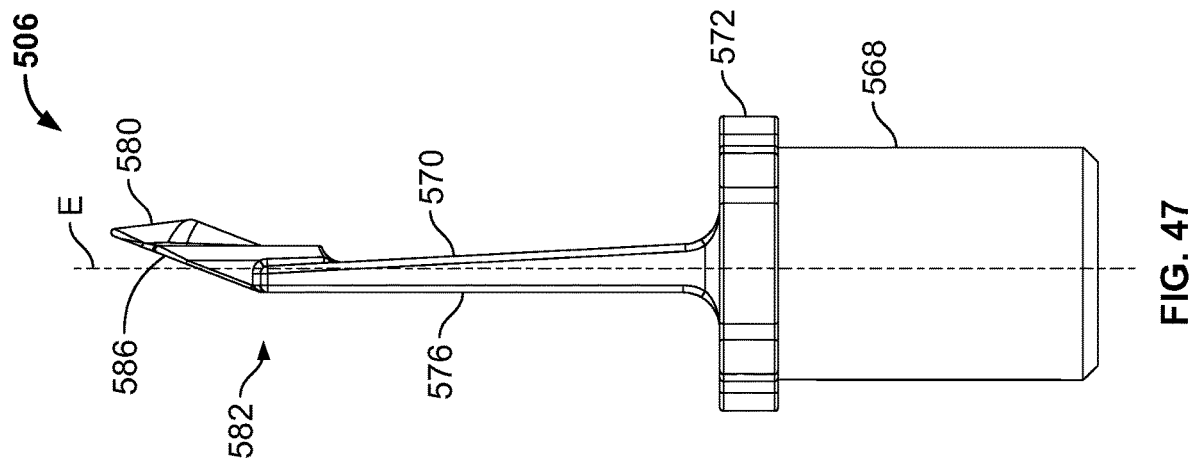
FIG. 47 is a side view of the piston.
Figure 46:
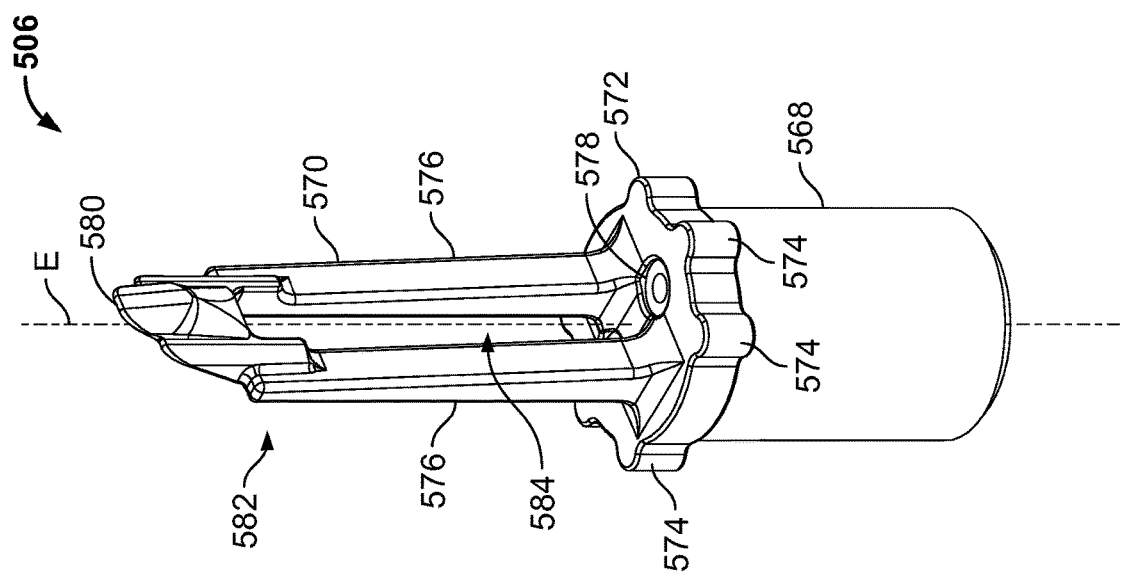
FIG. 46 is a rear perspective view of the piston.

The piston hanger 570 also includes a pair of tapered arms 576 arranged substantially symmetrically about the centerline "E." The tapered arms 576 extend upwardly from the bottom wall 572. As illustrated in the FIGS., the mounting holes 578 are positioned between the tapered arms 576 and extend axially through the bottom wall 572. As illustrated in the FIGS. 45-47, the piston hanger 570 includes a bridge portion 580 that extends between upper ends 582 of the tapered arms 576. As such, a closed longitudinal gap 584 is defined between the tapered arms 576, the bottom wall 572, and the bridge portion 580. The gap is sized to receive the piston retention member 546 of the housing 502 slidingly therein. The bridge portion 580 includes an upper inclined face 586 that is configured to engage the button 504 of the applicator 500 to facilitate release of the piston 506 from the piston retention member 546, as is further described herein.

With reference the FIGS. 40-42, the button 504 includes a body portion 590 that has a release member 592 extending generally axially downwardly therefrom. The release member 592 includes an inclined face 594 that is configured to slidingly engage the upper inclined face 586 of the piston hanger 570. The button also includes a cavity 596 that is configured to receive at least a portion of the bridge portion 580 therein when the button 504 is actuated. A pair of opposite retention members 598 extends generally radially outwardly from the bottom of the body portion 590. As illustrated in FIG. 42, each retention member 598 is positioned in a channel defined in the housing 502. In particular, the body 520 includes a pair of channels 600 that correspond to a pair of channels 602 formed in the cap 522 to define a channel that retains the button 504 and facilitates axial displacement of the button 502.

In the exemplary embodiment, the safety arms 508, 509 are inserted into the housing 502 and positioned in the channels 550 such that the lower end 556 is positioned at the second step portion 534 of the stepped bore 528. In addition, the piston spring 512 is inserted into the stepped bore 528 and positioned against the bottom of the piston retention member 546. The piston 506 is positioned in the third step portion 538 of the stepped bore 528. In particular, the protrusions 574 of the piston 502 are each aligned with a respective groove 540 of the housing 502. Further, the piston hanger 570 is inserted axially through the piston spring 512 and oriented to engage the piston retention member 546. The retaining ring 525 is coupled to the housing 502 to axially retain the piston 502 and the safety arms 508, 509 within the housing 502. The safety arm springs 510 and the button spring 514 are inserted into the stepped bore 528 from the top 518 of the body 520. The button spring 514 rests against the top of the piston retention member 546 and the safety arm springs 510 rest against the top of the safety arms 508, 509. The button 504 is positioned against the top 518 of the body 520 with the retention members 598 aligned with the channels 600 defined in the body 520. The cap 522 is coupled to the top 518 of the housing 502 with one or more fasteners (not shown) to retain the button 504 and the safety arm springs 510.

In operation, the piston 506 is displaced axially upwardly in the stepped bore 528. Clearance between the protrusions 574 of the piston 502 and the grooves 540 of the housing 502 enable the bridge portion 580 of the piston 506 to be displaced an amount off axis to slide axially past the piston retention member 546. The piston spring 512 functions to bias the piston 506 downwardly with respect to the piston retention member 546. This also facilitates generally aligning the axis of the piston 506 with the axis of the housing 502 to enable the bridge portion 580 to engage the piston retention member 546. As such, the piston retention member 546 extends into the gap 584 of the piston 506 to secure the piston 506 in place on the piston retention member 546.

The safety arm springs 510 bias the safety arms 508, 509 axially downwardly such that the lower ends 556 of the safety arms 508, 509 extend downwardly from the second step portion 534 into the first step portion 530 of the stepped bore 528. This enables the piston locking arms 558, and in particular, the protrusions 560 extending therefrom, to be positioned adjacent the upper ends 582 of the tapered arms 576. In such an orientation, the piston 506 is prevented from being displaced from the piston retention member 546 by the piston locking arms 558.

To use the applicator 500 with the fluid delivery apparatus 10, as is described herein, the user attaches the attachment band 430 and the fluid delivery apparatus 10 to the user's body. In particular, the attachment band 430 is stretched and tightened around the user's body, such as an arm or wrist of the user. The band provides a generally axial force to the fluid delivery apparatus 10, generally along the central axis "A." The force of the fluid delivery apparatus 10 against the user's body facilitates causes the portion of the user's skin beneath the fluid delivery apparatus 10 to form a crown within the collet assembly 12. The collet assembly 12 also facilitates maintaining an appropriate amount of deformation (strain) of the user's skin during use of the fluid delivery apparatus 10. The indicator 444, which is visible through the window 61 of the first coupling member 66, presents a visual indication to the user that indicates when the attachment band 430 is stretched enough to impart the proper amount of force to the fluid delivery apparatus 10. The skin deformation and the crowning of the portion of the user's skin encircled by the collet assembly 12 facilitate proper penetration of the microneedle array assembly 108 into the user's skin.

Figure 48:
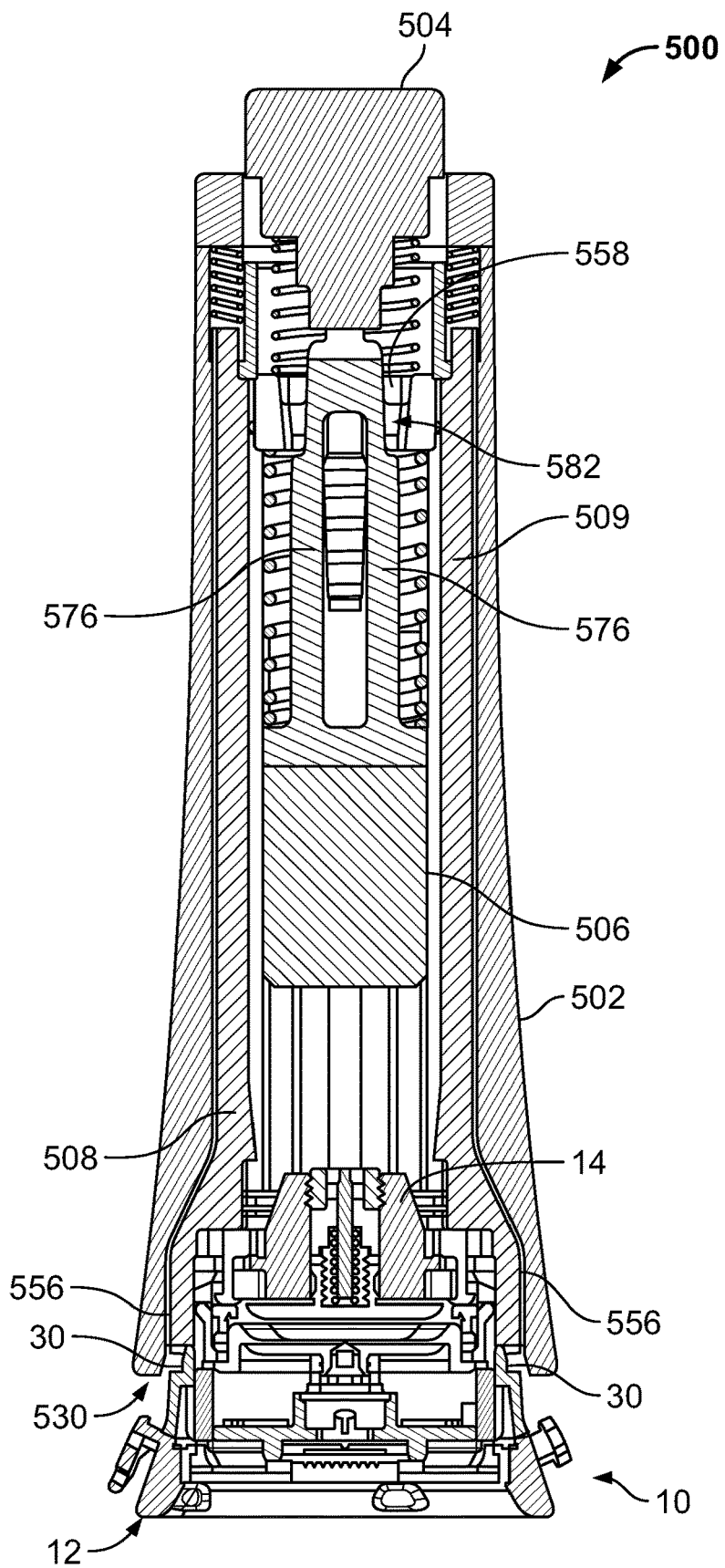
FIG. 48 is a sectional view of the applicator attached to the fluid delivery apparatus.

The applicator 500 is positioned onto the fluid delivery apparatus 10 as shown in FIG. 48. The upper wall 30 of the collet assembly 12 is disposed into the first step portion 530 of the stepped bore 528. The upper wall 30 contacts the lower ends 556 of the safety arms 508, 509. As the user applies downward pressure to the applicator 500, the safety arms 508, 509 are displaced axially upwardly in the channels 550 such that the piston locking arms 558 are displaced away from the upper ends 582 of the tapered arms 576. The user presses the button 504 to release the piston 506. In particular, as the button 504 is pressed, the inclined face 594 of the button release member 592 slidingly engages the upper inclined face 586 of the piston hanger 570. As the button is pressed further down, the upper inclined face 586 of the piston hanger 570 is displaced transversely to the central axis "E" of the applicator 500. When the bridge portion 580 disengages from the piston retention member 546, the piston spring 512 forces the piston 506 axially downwardly within the housing 502. The piston 506 contacts the threaded adjustment member 370 of the mechanical controller assembly 20 to displace the fluid delivery apparatus 10 from the pre-use configuration shown in FIG. 1A to the pre-activated configuration shown in FIG. 1B.

As described herein, the piston has a predetermined mass that enables the piston 506 to achieve a desirable velocity and impulse rate during use of the applicator 500 to properly activate the fluid delivery apparatus 10 for use. In the exemplary embodiment, the mass of the piston 506 and the spring force of the piston spring 512 combine to provide a momentum or impulse of the piston 506 greater than about 0.05 newton seconds (Ns), and a kinetic energy of the piston 506 greater than about 0.1 kilogram meters$^2$/second$^2$ (kg·m$^2$/s$^2$) or joules (J) at impact with the threaded member 370 of the mechanical controller assembly. The piston contacts the mechanical controller assembly 20 with a predetermined velocity and impulse rate to overcome the mechanical properties of the fluid delivery apparatus 10 such that the plurality of microneedles 234 of the microneedle array assembly 108 are accelerated toward and properly inserted into the user's skin. In one suitable embodiment, the microneedle array assembly 108 is configured to impact the user's skin at a velocity of at least about 4 meters/second (m/s). Alternatively, the microneedle array assembly 108 is configured to impact the user's skin at any velocity that enables the microneedle array assembly 108 to be properly inserted into the user's skin.

After the fluid delivery apparatus 10 is properly attached to the user and configured in the pre-activated configuration shown in FIG. 1B, the user can activate the fluid delivery apparatus 10 by pressing the pivoting latches 368 to release the plunger component 362. In one embodiment, the user may use a tool (not shown) configured to simultaneously press the pivoting latches 368. When the pivoting latches 368 are pressed, the pivot about the cylindrical pins 452 such that the concave cutouts 458 of the latch portions 456 pivot into axial alignment with the central axis "A." This enables the plunger component 362 to disengage from the pivoting latches 368 and contact the upper sealing member 280 of the cartridge assembly 18.

In the exemplary embodiment, the biasing assembly 364 functions to apply an axial two stage force profile to the plunger component 362 during use of the fluid delivery apparatus 10. In particular, when the plunger component 362 is released, the second biasing member 378 and the first biasing member 372 apply force to the plunger component 362, i.e., a first force profile. As illustrated in FIG. 1B, the axial location of the upper ends of the second biasing member 378 and the first biasing member 372 are axially displaced with respect to each other. Further, as described herein, the second biasing member 378 and the first biasing member 372 have different lengths and force constants, thus the axial force applied to the plunger component 362 changes with respect to the displacement of the plunger component 362.

Initially, as the plunger component 362 is displaced axially by the biasing assembly 364, the second biasing member 378 and the first biasing member 372 are applying force to the plunger component 362. As the plunger component 362 is displaced, the second biasing member 378 and the first biasing member 372 extend such that the force exerted on the plunger component 362 decreases. At a predetermined axial displacement of the plunger component 362, the second biasing member 378 becomes fully extended or is prevented from being extended further by the threaded fastener 374 and the nut 382. At this position, the first biasing member 372 continues to apply a force to the plunger component 362, i.e., a second force profile.

In particular, as illustrated in FIG. 1B, the second biasing member 378 and the first biasing member 372 are configured to extend axially downwardly when the plunger component 362 is released. The first biasing member 372 and the second biasing member 378 press against the insert component 380, which is positioned against the threaded adjustment member 370. As the second biasing member 378 extends downward, the threaded fastener 374, the tube 376, and the nut 382 move axially within the insert component 380. When the nut 382 contacts a top of the insert component 380, the second biasing member 378 is prevented from expanding, and therefore, from exerting any force on the plunger component 362. The first biasing member 372, however, continues to exert force until the plunger component 362 is displaced fully against the reservoir component 270 of the cartridge assembly 18.

The pressure applied to the plunger component 362 by the biasing assembly 364 is transmitted to the cartridge assembly 18. The pressure facilitates displacing the fluid contained in the upper cavity 272 through the cannula 104 and into the fluid passage 276. The fluid exits the fluid passage 276 by flowing into the plenum cap assembly 106. In particular, with reference to FIG. 14, the fluid flows downwardly through the aperture 204 of the first adhesive layer 192, the aperture 208 of the vent membrane 194, and into the arcuate slot 210 of the second adhesive layer 196. The impermeable membrane 198 is coupled to the bottom of the second adhesive layer 196, thereby preventing the fluid from passing directly therethrough. As such, the pressure applied by the biasing assembly 364 forces the fluid to fill the arcuate slot 210, where it is channeled to the aperture 222 in the impermeable membrane 198. The fluid passes through the aperture 222 where it enters the slot 224 formed in the third adhesive layer 200. The fluid is channeled by the slot 224 to the inlet channel 254 of the microneedle array assembly 108.

During use of the fluid delivery apparatus 10, gas and/or air may be mixed or become mixed with the fluid. As such, the plenum cap assembly 106 is configured to facilitate removing such gas and/or air from the fluid. As the fluid is force through the arcuate slot 210, the pressure facilitates removing the gas from the fluid. In particular, the fluid fills the arcuate slot 210 such that it contacts the vent membrane 194 positioned above the second adhesive layer 196. The gas and/or air dispersed through the fluid is forced upward toward the vent membrane 194, where it passes therethrough. As described herein, the vent membrane 194 is fabricated from a gas permeable oleophobic/hydrophobic material, such that the gas and/or air passes through, but the fluid cannot. The gas and/or air then passes through the slot 202 of the first adhesive layer 192. The arcuate slot 202 is configured to at least partially correspond to the arcuate channel 176 of the plenum component 102, such that the gas and/or air may be vented out of the fluid flow and into the internal chamber 167 of the plenum component 102. As described herein, the plenum component 102 is configured to attach to the cartridge assembly 18, thereby facilitating creating a sterile internal chamber 167 for receiving the vented gas.

The fluid is channeled to the inlet channel 254 of the microneedle array assembly 108, substantially free of gas and/or air bubbles. The fluid enters the distribution manifold 238, and then the fluid flows through the supply channels 256, the resistance channels (not shown), and the outlet channels 258 to the passageways 246 of the microneedles 234 and into the user's skin. In the exemplary embodiment, the biasing assembly 364 functions in connection with the plunger component 362 to provide substantially complete emptying of the fluid from the cartridge assembly 18 through the cannula 104 and into the fluid passage 276. The plunger component 362 and the biasing assembly 364 may provide an initial force in a range of about 32 kilopascals (kPa) (4.6 pounds per square inch (psi)) to about 150 kPa (21.8 psi).

In the exemplary, embodiment, the mathematical representation of the force provided to the plunger component 362 by the biasing assembly 364 is the sum of the force from the first biasing member 372 and the second biasing member 378:

$$F(x)=FM(x)+FT(x) \hspace{2cm} \text{Equation 1}$$

Where FM(x) equals the force from the first biasing member 372 in newtons as a function of position in millimeters, and where FT(x) equals the force from second biasing member 378 in newtons as a function of position in millimeters.

The force from the first biasing member 372 can be represented by two expressions, depending on where the plunger component 362 is located with respect to the length of the first biasing member 372:

$$FM(x) = \begin{cases} K_m(L_m - (B_m - x)) & x < L_M - B_M \\ 0 & x \geq L_M - B_M \end{cases} \hspace{1cm} \text{Equation 2}$$

Where $K_m$ equals the force constant of the first biasing member 372, $L_m$ equals the length of the first biasing member 372, $B_m$ equals the base length of the first biasing member 372, and x equals the displacement of the plunger component 362 with respect to the length of the first biasing member 372.

Similarly the force from second biasing member 378 is:

$$FT(x) = \begin{array}{ll} K_T(L_T - (B_T - x)) & x < L_T - B_T \\ 0 & x \geq L_T - B_T \end{array} \quad \text{Equation 3}$$

Where $K_T$ equals the force constant of the second biasing member 378, $L_T$ equals the length of the second biasing member 378, $B_T$ equals the base length of the second biasing member 378, and x equals the displacement of the plunger component 362 with respect to the length of the second biasing member 378.

In the exemplary embodiment, the first biasing member 372 length extends beyond the maximum travel of the plunger component 362 such that the condition described in Equation 2 cannot be met. As such, the first biasing member 372 always applies a force to plunger component 362. In addition, a length of the second biasing member 378 is predetermined such that the second biasing member 378 discontinues providing force to the plunger component 362 before the plunger component 362 has reached its maximum travel. In the exemplary embodiment, the conditions described in Equation 3 are valid for at least some portion of the travel of the plunger component 362.

The apparatus, system, and methods described in detail herein enable a fluid delivery apparatus to remove gas and/or air from a medicine and to distribute a substantially equal quantity of the medicine through each microneedle of the microneedle assembly. A plenum cap assembly of the fluid delivery apparatus includes a fluid supply channel disposed between an impermeable material and a gas permeable oleophobic/hydrophobic material. This facilitates removing the gas and/or air from the medicine while delivering substantially all of the medicine to the user of the fluid delivery apparatus 10. In addition, a biasing assembly enables a pressure profile to be determined to facilitate optimizing the flow rate and distribution of the medicine through a microneedle array assembly over an extended period of time, thereby facilitating a steady state concentration of the fluid that is delivered to the user. Moreover, the fluid delivery apparatus includes a band or strap that enables the fluid delivery apparatus to be appropriately attached to the user's skin to facilitate optimal insertion of the microneedles into the user's skin.

Exemplary embodiments of an apparatus, system, and methods for a fluid delivery apparatus are described above in detail. The apparatus, system, and methods described herein are not limited to the specific embodiments described, but rather, components of apparatus, systems, and/or steps of the methods may be utilized independently and separately from other components and/or steps described herein. For example, the methods may also be used in combination with other fluid delivery apparatus, systems, and methods, and are not limited to practice with only the apparatuses, systems, and methods described herein. Rather, the exemplary embodiments can be implemented and utilized in connection with many fluid delivery applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

As various changes could be made in the above embodiments without departing from the scope of the disclosure, it is intended that all matter contained in the above description and shown in the accompanying drawings shall be interpreted as illustrative and not in a limiting sense.

What is claimed is:

1. A gas extraction device for a fluid delivery apparatus, the gas extraction device comprising:
   a first layer having a first slot spaced from the first aperture;
   a vent membrane coupled to the first layer and configured to allow gas to pass therethrough and inhibit liquid from passing therethrough;
   a second layer coupled to the vent membrane opposite the first layer, the second layer comprising a second slot being at least partially being aligned with the first slot in the first layer such that the vent membrane is disposed between the first slot and the second slot to inhibit liquid communication between the first slot and second slot and allow gas communication between the first slot and the second slot; and
   an impermeable membrane coupled to the second layer opposite the vent membrane.

2. The gas extraction device in accordance with claim 1, wherein the first slot and the second slot are at least partially arcuate.

3. The gas extraction device in accordance with claim 2, wherein the first slot in the first layer is generally U-shaped.

4. The gas extraction device in accordance with claim 3, wherein the second slot in the second layer is generally G-shaped.

5. The gas extraction device in accordance with claim 1, wherein the first slot comprises a first width and the second slot comprises a second width, the second with being different than the first width.

6. The gas extraction device in accordance with claim 5, wherein the first width is less than the second width.

7. A gas extraction device for a fluid delivery apparatus, the gas extraction device comprising:
   a first layer having a first inlet aperture and a first slot spaced from the first aperture;
   a vent membrane coupled to the first layer and configured to allow gas to pass therethrough and inhibit liquid from passing therethrough, the vent membrane having an inlet aperture aligned with the first inlet aperture of the first layer;
   a second layer coupled to the vent membrane opposite the first layer, the second layer comprising a second slot, the second slot being in fluid communication with the first inlet aperture in the first layer and the inlet aperture in the vent membrane, the second slot at least partially being aligned with the first slot in the first layer such that the vent membrane is disposed between the first slot and the second slot to inhibit liquid communication between the first slot and second slot and allow gas communication between the first slot and the second slot; and an impermeable membrane coupled to the second layer opposite the vent membrane, the impermeable membrane having aperture in fluid communication with the second slot of the second layer, the aperture in the impermeable membrane being out of alignment with the first aperture in the first layer and the inlet aperture in the vent membrane.

8. A gas extraction device in accordance with claim 7, wherein the first slot and the second slot are at least partially arcuate.

9. A gas extraction device in accordance with claim 8, wherein the first slot extends circumferentially about a center point on the first layer to a first angle, and the second slot extends circumferentially about a center point on the second layer to a second angle that is substantially similar to the first angle.

10. A gas extraction device in accordance with claim 7, further comprising a third layer coupled to the impermeable membrane opposite the second layer, the third layer comprising a third slot having a third slot first end and a third slot second end.

11. A gas extraction device in accordance with claim 10, wherein the third slot first end is aligned with the aperture in the impermeable member.

12. A gas extraction device in accordance with claim 11, wherein the third slot second end is aligned with the first inlet aperture in the first layer and the inlet aperture in the vent membrane.

13. A gas extraction device in accordance with claim 12, wherein the third slot in the third layer is generally linear.

14. A gas extraction device in accordance with claim 13, wherein the second slot in the second layer comprises a generally linear portion and an arcuate portion extending from an end of the linear portion.

15. A fluid delivery apparatus comprising:
a cartridge assembly containing a fluid;
a plenum assembly coupled to the cartridge assembly, the plenum assembly comprising a cannula and a mounting surface; and a gas extraction device coupled to the mounting surface, the gas extraction device comprising:

a first layer having a first arcuate slot;

a vent membrane coupled to the first layer and configured to allow gas to pass therethrough and inhibit liquid from passing therethrough;

a second layer coupled to the vent membrane opposite the first layer, the second layer comprising a second arcuate slot; the second arcuate slot at least partially being aligned with the first arcuate slot in the first layer such that the vent membrane is disposed between the first arcuate slot and the second arcuate slot to inhibit liquid communication between the first slot and second slot and allow gas communication between the first slot and the second slot.

16. A fluid delivery apparatus in accordance with claim 15 further comprising an impermeable membrane coupled to the second layer opposite the vent membrane.

17. A fluid delivery apparatus in accordance with claim 15, wherein the first slot comprises a first width centered at a first radius from a center point on the first layer, and wherein the second slot comprises a second width centered at a second radius from a center point on the second layer.

18. A fluid delivery apparatus in accordance with claim 17, wherein the first radius is substantially similar to the second radius, and wherein the first width is less than the second width.

19. A fluid delivery apparatus in accordance with claim 16 further comprising a third layer coupled to the impermeable membrane opposite the second layer, the third layer having a third slot formed with a third slot first end and a third slot second end.

20. A fluid delivery apparatus in accordance with claim 19, wherein the first layer comprises a first fluid aperture, wherein the vent membrane comprises a second fluid aperture aligned with the first fluid aperture, and wherein the third slot first end is aligned with the first fluid aperture and second fluid aperture.

* * * * *